US009913898B2

(12) United States Patent
Schlegl et al.

(10) Patent No.: US 9,913,898 B2
(45) Date of Patent: Mar. 13, 2018

(54) ALUMINUM COMPOUNDS FOR USE IN THERAPEUTICS AND VACCINES

(71) Applicant: Valneva Austria GmbH, Vienna (AT)

(72) Inventors: Robert Schlegl, Siegenfeld (AT); Michael Möhlen, Vienna (AT); Jürgen Wruss, Vienna (AT); Michael Weber, Vienna (AT)

(73) Assignee: Valneva Austria GmbH, Vienna (AT)

( * ) Notice: Subject to any disclaimer, the term of this patent is extended or adjusted under 35 U.S.C. 154(b) by 2 days.

(21) Appl. No.: 15/223,027

(22) Filed: Jul. 29, 2016

(65) Prior Publication Data

US 2016/0324959 A1 Nov. 10, 2016

Related U.S. Application Data

(60) Continuation of application No. 14/873,344, filed on Oct. 2, 2015, which is a division of application No. 13/449,596, filed on Apr. 18, 2012.

(51) Int. Cl.

| | |
|---|---|
| ***A61K 39/00*** | (2006.01) |
| ***A61K 39/39*** | (2006.01) |
| ***C07D 487/04*** | (2006.01) |
| ***C09K 13/00*** | (2006.01) |
| ***A61K 38/43*** | (2006.01) |
| ***A61K 38/16*** | (2006.01) |
| ***A61K 39/12*** | (2006.01) |
| ***C12N 7/00*** | (2006.01) |
| ***A61K 39/104*** | (2006.01) |

(52) U.S. Cl.

CPC ............ *A61K 39/39* (2013.01); *A61K 38/162* (2013.01); *A61K 38/164* (2013.01); *A61K 39/104* (2013.01); *A61K 39/12* (2013.01); *C12N 7/00* (2013.01); *A61K 2039/525* (2013.01); *A61K 2039/5252* (2013.01); *A61K 2039/55505* (2013.01); *A61K 2039/70* (2013.01); *C12N 2770/24134* (2013.01)

(58) Field of Classification Search

CPC ...... A61K 2300/00; A61K 2039/55505; A61K 39/12; A01N 2300/00; C12N 2770/24134

See application file for complete search history.

(56) References Cited

U.S. PATENT DOCUMENTS

| | | | |
|---|---|---|---|
| 2,375,977 A | 5/1945 | Davies et al. | |
| 5,545,403 A | 8/1996 | Page et al. | |
| 5,545,405 A | 8/1996 | Page et al. | |
| 5,654,403 A | 8/1997 | Smith et al. | |
| 5,792,838 A * | 8/1998 | Smith | A61K 39/39591 530/387.1 |
| 2004/0054146 A1 | 3/2004 | Hellman et al. | |
| 2005/0158334 A1 | 7/2005 | Contorni et al. | |
| 2010/0215580 A1 | 8/2010 | Hanes et al. | |
| 2011/0268805 A1 | 11/2011 | Alexis et al. | |
| 2012/0027720 A1 | 2/2012 | Tamiz et al. | |
| 2013/0280295 A1 | 10/2013 | Schlegl et al. | |
| 2016/0114033 A1 | 4/2016 | Schlegl et al. | |

FOREIGN PATENT DOCUMENTS

| | | |
|---|---|---|
| CN | 101734698 | 6/2010 |
| GB | 120550 | 3/1919 |
| GB | 1121833.6 | 2/2012 |
| GB | 1204360.0 | 5/2012 |
| WO | WO 1998/014401 A1 | 4/1998 |
| WO | WO 2009/137436 A2 | 11/2009 |
| WO | WO 2009/158284 A2 | 12/2009 |
| WO | WO 2011/075822 A1 | 6/2011 |
| WO | WO2011075822 * | 6/2011 |
| WO | PCT/EP2012/054387 | 10/2012 |
| WO | PCT/EP2012/074701 | 2/2013 |

OTHER PUBLICATIONS

IXIARO®, Annex 1 Summary of Product Characteristics, European Medicines Agency, IXIARO® pdf, authorized Mar. 31, 2009.*

Schlegl et al., Vaccine, 2015, 33:5989-5996.*

[No Author Listed] European Medicines Agency (Market Authorisation): Ixiaro® authorised Mar. 31, 2009. Available at http://www.ema.europa.eu/docs/en_GB/document_library/EPAR-Product_Information/human/000963/WC500037287.pdf. Last updated Mar. 23, 2010.

[No Author Listed] General Chemical, Rehydragel Adjuvants Product Profile. 2009. 1-2; Available at http://www.generalchemical.com/assets/pdf/Rehydragel_Adjuvants_Product_Profile.pdf.

[No Author Listed] IXIARO®, Annex 1 Summary of Product Characteristics, European Medicines Agency, IXIARO® pdf, authorized Mar. 31, 2009.

[No Author Listed] World Health Organization "WHO", Annex 1 Guidelines for the production and quality control of synthetic peptide vaccines.1999. WHO Technical Report Series, No. 889.

[No Author Listed] World Health Organization, Temperature Sensitivity of Vaccines, WHO Press, Department of Immunization, Vaccines and Biologicals. Aug. 2006. 1-62.

[No Author Listed], 2.4.8. Heavy Metals. European Pharmacopoeia, 7th Edition. Jan. 1, 2011; 114-117. Originally published on Jul. 15, 2010.

[No Author Listed], Aluminium Hydroxide Wet Gel, USP. Type: VISCO 9. SPI Pharma. Nov. 2010.

[No Author Listed], Aluminium hydroxide, hydrated, for adsorption. European Pharmacopoeia 6.1. 2008:3395-3396.

[No Author Listed], Aluminium in adsorbed vaccines. European Pharmacopoeia 7.0. 2010:141.

[No Author Listed], Aluminum Hydroxide Wet Gel. Type: VAC 20. SPI Pharma. Feb. 2008.

[No Author Listed], Aluminum hydroxide, hydrated, for adsorption. European Pharmacopoeia 7.0 2010:1357-1358.

[No Author Listed], Arsenic. European Pharma. 2010. 7.0; 2.4.2.:113.

(Continued)

*Primary Examiner* — Barry A Chestnut

(74) *Attorney, Agent, or Firm* — Wolf, Greenfield & Sacks, P.C.

(57) ABSTRACT

The invention relates to means and methods for preparing aqueous composition comprising aluminum and a protein said composition comprising less than 700 ppm heavy metal on the basis of weight with respect to the aluminum content. The invention further relates to aqueous compositions comprising a protein and an aluminum-salt, said composition comprising less than 350 ppb heavy metal based on the weight of the aqueous composition.

18 Claims, 16 Drawing Sheets

(56) References Cited

OTHER PUBLICATIONS

[No Author Listed], Assessment report for IXIARO. European Medicines Agency. May 25, 2012; 8 pages.
[No Author Listed], Diphtheria and pertussis vaccination. WHO technical report series. May 1953;61 :5-88.
[No Author Listed], Iron. European Pharma. 2010. 7.0; 2.4.9.:117.
[No Author Listed], Limit tests—206 aluminum. USP 34. 2011;124-125.
[No Author Listed], Product Specification. Alhydrogel 2%. Statens Serum Institut.
[No Author Listed], Raw material specification: ammonia alum. Issue No. 7. 2011. 1 page.
[No Author Listed], Rehydragel Adjuvants, Product Profile. General Chemical. 2008; pp. 1-2. http://www.generalchemical.com/assets/pdf/Rehydragel_Adjuvants_Product_Profile.pdf [last accessed Oct. 8, 2012].
[No Author Listed], Tentative method of test for nitrite ion in industrial water. ASTM D 1254-53T, 1953;308-309.
[No Author Listed], Vaccines for Human Use. European Pharmacopoeia 7.6. 2012:4820-4823.
[No Author Listed], Vaccines for Human Use. European Pharmacopoeia 7.0. 2010:695-698.
Abadie, Letter re: “Possible effect of high metal ion content in aluminium hydroxide used for the manufacturing of vaccines” sent Dec. 15, 2011. European Medicines Agency.
Abadie, Letter to Executive Director of European Vaccines Manufacturers re: “Use of aluminium hydroxide in the manufacturing process of vaccines—concerns on the possible effect of high metal ion content” sent Dec. 15, 2011. European Medicines Agency.
Abadie, Letter to Peter Bachmann re: “Use of aluminium hydroxide in the manufacturing process of vaccines—concerns on the possible effect of high metal ion content” sent Dec. 15, 2011. European Medicines Agency.
Abadie, Letter to regulatory contact person of GlaxoSmithKline Biologicals S.A. re: “Use of aluminium hydroxide in the manufacturing process of vaccines—concerns on the possible effect of high metal ion content” sent Dec. 15, 2011. European Medicines Agency.
Alipazaga et al., Synergistic effect of Ni(II) and Co(II) ions on the sulfite induced autoxidation of Cu(II)/tetraglycine complex. Dalton Trans. Jul. 7, 2004;(13):2036-40. Epub May 6, 2004.
Baylor et al., Aluminum salts in vaccines—US perspective. Vaccine. May 31, 2002;20 Suppl 3:S18-23. Review. Erratum in: Vaccine. Sep. 10, 2002;20(27-28):3428.
Berglund et al., Kinetics and mechanism for manganese-catalyzed oxidation of sulfur (IV) by oxygen in aqueous solution. Inorg Chem. 1993;32:4527-38.
Brandt et al., Role of chromium and vanadium in the atmospheric oxidation of sulfur (IV). Atmos Environ. 1998;32(4):797-800.
Burnouf et al., A highly purified factor VIII:c concentrate prepared from cryoprecipitate by ion-exchange chromatography. Vox Sang. 1991;60(1):8-15.
Casdorph, EDTA Chelation Therapy: Efficacy in Arteriosclerotic Heart Disease. J Advanc Med. 1989;2:121-129.
Dash et al., Sample treatment approaches for trace level determination of cesium in hepatitis B vaccine by suppressed ion chromatography. Chromatographia. 2012;75(1-2):17-23. Epub Nov. 8, 2011.
Estey et al., Evaluation of chemical degradation of a trivalent recombinant protein vaccine against botulinum neurotoxin by LysC peptide mapping and MALDI-TOF mass spectrometry. J Pharm Sci. Sep. 2009;98(9):2994-3012. Epub Sep. 9, 2008.
Exley et al., The immunobiology of aluminium adjuvants: how do they really work? Trends Immunol. Mar. 2010;31(3):103-9. Epub Feb. 10, 2010.
Gupta, Aluminum compounds as vaccine adjuvants. Adv Drug Deliv Rev. Jul. 6, 1998;32(3):155-172.
Huie et al., One-electron redox reaction in aqueous solutions of sulphite with hydroquinone and other hydroxyphenols. J Phys Chem. 1985;89(18):3918-3921.
Ito et al., Site-specific fragmentation and modification of albumin by sulfite in the presence of metal ions or peroxidase/H2O2: role of sulfate radical. Biochem Biophys Res Commun. May 15, 1991;176(3):1306-12.
Janosova et al., Determination of selected elements by x-ray fluorescence spectrometry in liquid drug samples after the preconcentration with thioacetamide. ЖУРНАЛ АНАЛИТИЧЕСКОЙ ХИМИИ (Journal of Analytical Chemistry). 2010;65(1):59-65.
Lambeth et al., The kinetics and mechanism of reduction of electron transfer proteins and other compounds of biological interest by dithionite. J Biol Chem. Sep. 10, 1973;248(17):6095-103.
Li et al., Chemical instability of protein pharmaceuticals: Mechanisms of oxidation and strategies for stabilization. Biotechnol Bioeng. Dec. 5, 1995;48(5):490-500.
Lima et al., Ruthenium(II) tris(bipyridyl) ion as a luminescent probe for oxygen uptake on the catalyzed oxidation of HSO(3)(−). Talanta. Mar. 4, 2002;56(3):547-56.
Lindblad, Aluminium compounds for use in vaccines. Immunol Cell Biol. Oct. 2004;82(5):497-505.
Mayo et al., Protection against oxidative protein damage induced by metal-catalyzed reaction or alkylperoxyl radicals: comparative effects of melatonin and other antioxidants. Biochim Biophys Acta. Mar. 17, 2003;1620(1-3):139-50.
Mukherjee, Preparation of adsorbed normal plasma. Haematology. Medical laboratory technology. 2008; 1:386.
Neta et al., Free-radical chemistry of sulfite. Environ Health Perspect. Dec. 1985;64:209-17.
Poland, The role of sodium bisulfite in the 1996-1997 USA influenza vaccine recall. Vaccine. Nov. 1998;16(19):1865-8.
Qian et al., Addition of CpG ODN to recombinant Pseudomonas aeruginosa ExoProtein A conjugates of AMA1 and Pfs25 greatly increases the number of responders. Vaccine. May 12, 2008;26(20):2521-7. Epub Mar. 27, 2008.
Qian et al., Conjugating recombinant proteins to Pseudomonas aeruginosa ExoProtein A: a strategy for enhancing immunogenicity of malaria vaccine candidates. Vaccine. May 16, 2007;25(20):3923-33. Epub Mar. 13, 2007.
Ranguelova et al., (Bi)sulfite oxidation by copper, zinc-superoxide dismutase: Sulfite-derived, radical-initiated protein radical formation. Environ Health Perspect. Jul. 2010;118(7):970-5. Epub Mar. 26, 2010.
Richardson, Letter to Grant Castle re: “Access to documents held by the European Medicines Agency” sent Jan. 24, 2013. European Medicines Agency.
Romero, Specification for Rehydragel® CG Aluminum Hydroxide Compressed Gel. General Chemical Standard Operating Procedure. Jul. 14, 2011; 2 pages.
Schlegl et al., Influence of elemental impurities in aluminum hydroxide adjuvant on the stability of inactivated Japanese Encephalitis vaccine, IXIARO(®). Vaccine. Nov. 4, 2015;33(44):5989-96. doi: 10.1016/j.vaccine.2015.05.103. Epub Jun. 19, 2015.
Shi, Generation of SO3.- and OH radicals in SO3(2−) reactions with inorganic environmental pollutants and its implications to SO3(2−) toxicity. J Inorg Biochem. Nov. 15, 1994;56(3):155-65.
Srivastava et al., A purified inactivated Japanese encephalitis virus vaccine made in Vero cells. Vaccine. Aug. 14, 2001;19(31):4557-65.
Stadtman, Metal ion-catalyzed oxidation of proteins: biochemical mechanism and biological consequences. Free Radic Biol Med. 1990;9(4):315-25.
Stewart-Tull, Harmful and Beneficial Activities of Immunological Adjuvants. In: Vaccine Adjuvants. Preparation methods and research protocols. O'Hagan, Ed. 2000;42:29-63.
Trouvin, Letter to EDOM—Council of Europe re: “Use of aluminium hydroxide in the manufacturing process of vaccines—concerns on the possible effect of high metal ion content” sent Mar. 7, 2012. European Medicines Agency.
Trouvin, Letter to EDOM—Council of Europe re: “Use of aluminium hydroxide in the manufacturing process of vaccines—concerns on the possible effect of high metal ion content” sent Jul. 11, 2012. European Medicines Agency.

(56) References Cited

OTHER PUBLICATIONS

Wittayanukulluk et al., Effect of microenvironment pH of aluminum hydroxide adjuvant on the chemical stability of adsorbed antigen. Vaccine. Mar. 12, 2004;22(9-10):1172-6.
Wolthers, Letter to C. Vielle, Secretariat of the European Pharmacopoeia Commission re: Request for revision of monograph. Aluminum hydroxide, hydrated, for adsorption. 7th Ed., sent on Mar. 14, 2013.

* cited by examiner

| | |
|---|---|
| 1 | Fe(II) |
| 2 | Fe(III) |
| 3 | Ni(II) |
| 4 | Co(II) |
| 5 | Cu(II) |
| 6 | Zn(II) |
| 7 | Cr(III) |
| 8 | Mix |
| 9 | Control |

Figure 14

AHHHHHHAPAPEPVADVCSDSDNDGVCDNVDKCPDTPANVTVDANGCPAVAEVVRVQ
LDVKFDFDKSKVKENSYADIKNLADFMKQYPSTSTTVEGHTDSVGTDAYNQKLSERRAN
AVRDVLVNEYGVEGGRVNAVGYGESRPVADNATAEGRAINRRVESSHSKETEARLTAT
EDAAARAQARADEAYRKADEALGAAQKAQQTADEANERALRMLEKASRK

```
SEQUENCE LISTING


<160> NUMBER OF SEQ ID NOS: 1

<210> SEQ ID NO 1
<211> LENGTH: 223
<212> TYPE: PRT
<213> ORGANISM: Artificial Sequence
<220> FEATURE:
<223> OTHER INFORMATION: OprF-OprI fusion protein from pseudomonas ae.

<400> SEQUENCE: 1

Ala His His His His His His Ala Pro Ala Pro Glu Pro Val Ala Asp
1               5                   10                  15

Val Cys Ser Asp Ser Asp Asn Asp Gly Val Cys Asp Asn Val Asp Lys
            20                  25                  30

Cys Pro Asp Thr Pro Ala Asn Val Thr Val Asp Ala Asn Gly Cys Pro
        35                  40                  45

Ala Val Ala Glu Val Val Arg Val Gln Leu Asp Val Lys Phe Asp Phe
    50                  55                  60

Asp Lys Ser Lys Val Lys Glu Asn Ser Tyr Ala Asp Ile Lys Asn Leu
65                  70                  75                  80

Ala Asp Phe Met Lys Gln Tyr Pro Ser Thr Ser Thr Thr Val Glu Gly
                85                  90                  95

His Thr Asp Ser Val Gly Thr Asp Ala Tyr Asn Gln Lys Leu Ser Glu
            100                 105                 110

Arg Arg Ala Asn Ala Val Arg Asp Val Leu Val Asn Glu Tyr Gly Val
        115                 120                 125

Glu Gly Gly Arg Val Asn Ala Val Gly Tyr Gly Glu Ser Arg Pro Val
    130                 135                 140

Ala Asp Asn Ala Thr Ala Glu Gly Arg Ala Ile Asn Arg Arg Val Glu
145                 150                 155                 160

Ser Ser His Ser Lys Glu Thr Glu Ala Arg Leu Thr Ala Thr Glu Asp
                165                 170                 175

Ala Ala Ala Arg Ala Gln Ala Arg Ala Asp Glu Ala Tyr Arg Lys Ala
            180                 185                 190

Asp Glu Ala Leu Gly Ala Ala Gln Lys Ala Gln Gln Thr Ala Asp Glu
        195                 200                 205

Ala Asn Glu Arg Ala Leu Arg Met Leu Glu Lys Ala Ser Arg Lys
    210                 215                 220
```

ALUMINUM COMPOUNDS FOR USE IN THERAPEUTICS AND VACCINES

RELATED APPLICATIONS

This application is a continuation of U.S. application Ser. No. 14/873,344, filed Oct. 2, 2015, which is a divisional of U.S. application Ser. No. 13/449,596, filed Apr. 18, 2012, the disclosure of each of which is incorporated by reference herein in its entirety.

FIELD OF THE INVENTION

The invention relates to the fields of pharmaceuticals and vaccines. More in particular the invention relates to the field of compounds and compositions that are being co-administered with the medicament and/or antigen.

BACKGROUND OF THE INVENTION

Aluminium compounds (herein also referred to as "aluminium"), including aluminium phosphate (AlPO4), aluminium hydroxide (Al(OH)3), and other aluminium precipitated vaccines are currently the most commonly used adjuvants with human and veterinary vaccines. The adjuvants are often referred to as "alum" in the literature.

Aluminium adjuvants have been used in practical vaccination for more than half a century. They induce early, high-titre, long-lasting protective immunity. Billions of doses of aluminium-adjuvated vaccines have been administered over the years. Their safety and efficacy have made them the most popular adjuvants in vaccines to date. In general, aluminium adjuvants are regarded as safe when used in accordance with current vaccination schedules.

In human vaccinations, of old, aluminium adjuvants have been used in tetanus, diphtheria, pertussis and poliomyelitis vaccines as part of standard child vaccination programmes. Aluminium adjuvants have also been introduced into hepatitis A and hepatitis B virus vaccines and Japanese encephalitis virus (also referred herein as "JEV") vaccines. Other aluminium-adsorbed vaccines against, for example, anthrax, are available for special risk groups. In veterinary medicine aluminium adjuvants have been used in a large number of vaccine formulations against viral and bacterial diseases, and in attempts to make antiparasite vaccines.

Adjuvants typically serve to bring the antigen, the substance that stimulates the specific protective immune response, into contact with the immune system and influence the type of immunity produced, as well as the quality of the immune response (magnitude or duration); Adjuvants can also decrease the toxicity of certain antigens; and provide solubility to some vaccines components. Studies have shown that many aluminium-containing vaccines cause higher and more prolonged antibody responses than comparable vaccines without the adjuvant. The benefit of adjuvants has usually been observed during the initial immunization series rather than with booster doses.

There are three general types of aluminium-containing adjuvants:

Aluminium hydroxide, Aluminium phosphate and Potassium aluminium sulphate (collectively often referred to as "Alum").

The effectiveness of each salt as an adjuvant depends on the characteristics of the specific vaccine and how the manufacturer prepares the vaccine. To work as an adjuvant, the antigen is typically adsorbed to the aluminium; that is, it is clumped with the aluminium salt to keep the antigen at the site of injection.

Not all vaccines contain aluminium salts. Sometimes an adjuvant may not have been needed or another adjuvant was selected. Examples of commercial vaccines that do not contain aluminium salts are inactivated Polio Virus (IPV) vaccine, measles, mumps and rubella vaccine (MMR), varicella vaccine, Meningococcal conjugate (MCV4) vaccine, and influenza vaccines. That the commercial vaccines do not contain aluminium salts does typically not mean that an aluminium salt would not work. It just means that for some reason another adjuvant was selected.

Examples of US licensed vaccines for children that contain aluminium adjuvants are: DTP (diphtheria-tetanus-pertussis vaccine); DTaP (diphtheria-tetanus-acellular pertussis vaccine); some but not all Hib (*Haemophilus influenzae* type b) conjugate vaccines; Pneumococcal conjugate vaccine; Hepatitis B vaccines; Hepatitis A vaccines; Human Papillomavirus vaccine; Anthrax vaccine; and Rabies vaccine.

Aluminium is a very abundant element in our environment. It is in many foods we eat, many personal hygiene products we apply to our skin (deodorants, for example), and many medicines we ingest. Various government agencies establish guidelines for exposure to potentially toxic substances. These guidelines are called "minimal risk levels"—the maximum amount that one can be exposed to over time-usually on a daily basis-without expected harm.

The US Agency for Toxic Substances and Disease Registry (ATSDR) estimated these levels for infants taking into account the amount of aluminium (e.g. in form of a salt) a child would eat as well as receive by injection of vaccines. The body burden of aluminium from both sources is below the minimal risk level except transiently following vaccinations; since 50-70% of injected aluminium is excreted within 24 hours, this is believed to have no negative effect.

Aluminium hydroxide and aluminium phosphate adjuvants are generally prepared by exposing aqueous solutions of aluminium ions, to usually slightly alkaline conditions in a well-defined and controlled chemical environment. Various soluble aluminium salts can be used for the production of aluminium hydroxide. Anions present at the time of precipitation may coprecipitate (for review see, Lindblad, E B (2004) Immunol. and Cell Biol. Vol 82: 497-505).

Aluminium salt is also used in the manufacture and composition of medicaments. For instance, factor VIII is purified from plasma cryoprecipitate. The precipitate is solubilised, absorbed on aluminium hydroxide and then treated to inactivate lipid enveloped viruses. After several other processing steps the concentrate is used to treat hemophilia A patients (Burnouf T, (1991) Vox Sang. Vol 60: pp 8-15).

SUMMARY OF THE INVENTION

In the present invention it has been shown that stability of a biological in a composition that also comprises an aluminium salt is not always the same. The present invention, for instance, shows that the stability of a protein component (e.g. as such or within a complex such as e.g. a virus or other pathogen) in the context of an aqueous composition that also comprises aluminium salt is dependent on the content of heavy metals. To estimate a priori whether the protein will be stable in this composition, the present invention provides that it is necessary to determine the residual heavy metal content in the composition (otherwise the aqueous composition comprising a protein is at risk of being degraded over time in particular the invention provides that this risk is considerable when the residual heavy metal content is above 350 ppb (i.e. about 350 ng per ml) in said aqueous composition). Further, the invention also revealed that this residual heavy metal content cannot easily be removed from the aluminium compound. To this end the invention provides a method for preparing an aqueous composition comprising aluminium and a protein said method comprising—combining an aluminium-salt, said protein and water to produce said aqueous composition and—determining the level of a heavy metal in the aqueous composition and/or the aluminium-salt. Compositions comprising less than 350 ppb heavy metal based on the weight of the aqueous composition, can be stored in a liquid phase at a temperature of between 0 and 30 degrees Celsius, for at least 1 month, such as e.g. 20 months at 2-8° C. The protein component in said composition is stable for at least 1 month in said liquid phase. Compositions comprising more than 350 ppb heavy metal based on the weight of the aqueous composition cannot be stored for a prolonged period under such conditions as the protein component in said composition changes in at least one aspect over the indicated time period. One milliliter or one gram of aqueous composition thus preferably contains no more than 350 nanogram heavy metal. The aqueous composition preferably comprises between 0.1 mg/ml and 2.5 mg/ml aluminium. The average dose of aluminium per administration is preferably not more than 1.25 milligram (mgram). In a particularly preferred embodiment the dose of aluminium per administration is not more than 0.25 Ingram aluminium. A dose typically comprises between 0.5 and 1 ml of the aqueous composition.

In a further aspect of the present invention it has been shown that stability of a biological in a composition that comprises an aluminium salt and a reactive compound is not always the same. The present invention, for instance, shows that the stability of a protein component (e.g. as such or within a complex such as e.g. a virus or other pathogen) in the context of an aqueous composition that also comprises aluminium salt and a reactive compound such as e.g. a sulphite is critically dependent on the content of heavy metals. To estimate a priori whether the protein component (such as e.g. protein component within a complex such as e.g. a virus particle; herein also referred to simply as protein) will be stable in this composition, it is necessary to determine the heavy metal content in the composition. To this end the invention provides a method for preparing an aqueous composition comprising aluminium and a protein said method comprising—combining an aluminium-salt, said protein and water to produce said aqueous composition and—determining the level of a heavy metal in the aqueous composition and/or the aluminium-salt. Compositions comprising less than 350 ppb heavy metal based on the weight of the aqueous composition, can be stored in a liquid phase at a temperature of between 0 and 30 degrees Celsius, for at least 1 month, such as e.g. 20 months at 2-8° C. The protein component in said composition is stable for at least 1 month in said liquid phase, such as e.g. 20 months at 2-8° C. Compositions comprising more than 350 ppb heavy metal based on the weight of the aqueous composition cannot be stored for a prolonged period under such conditions as the protein component in said composition changes in at least one aspect over the indicated time period. One milliliter or one gram of aqueous composition thus preferably contains no more than 350 nanogram heavy metal. The aqueous composition preferably comprises between 0.1 mg/ml (milligram per milliliter) and 2.5 mg/ml aluminium. The average dose of aluminium per administration is preferably not more than 1.25 milligram (mgram). In a particularly preferred embodiment the dose of aluminium per administration is not more than 0.25 mgram aluminium. A dose typically comprises between 0.5 and 1 ml of the aqueous composition. An aqueous composition comprising a protein, an aluminium-salt, and optionally a reactive compound, said composition comprising less than 350 ppb heavy metal based on the weight of the aqueous composition is herein also referred to as "an aqueous composition comprising a protein according to the invention" or "a composition comprising a protein according to the invention".

It has been observed that the aluminium component is an important source for the heavy metal in the aqueous composition. Thus one way to control the amount of heavy metal in the aqueous composition is to control the amount of heavy metal in the aluminium source used to generate the aqueous composition. The invention therefore further provides a method for preparing an aqueous composition comprising aluminium and a protein said method comprising

- preparing or selecting an aluminium-salt solution (such as e.g. 10 mg/ml aluminium hydroxide liquid (such as e.g. ALHYDROGEL® 2% from Brenntag Biosector, catalogue number 843261) that in the final protein formulation comprises no more than 350 ppb based on the weight of the aqueous composition (e.g. for the ALHYDROGEL® 2% and final amount of 0.25 mgram aluminium hydroxide in the aqueous composition of 0.5 ml (=dose), the selected or prepared aluminium-salt solution should not contain more than 7 microgram heavy metal pro milliliter of the ALHYDROGEL® 2% solution, about 7 ppm heavy metal content), and
- combining said aluminium-salt solution, said protein, water and optionally a reactive compound to produce said aqueous composition (with no more than 350 ppb heavy metal in the aqueous composition).

For example, the aluminium-salt solution, e.g. the aluminium hydroxide liquid (used as a component to be mixed to result in the final aqueous composition) should not have a heavy metal content higher than 7 ppm (given as an example herein where the 10 mg/ml aluminium hydroxide liquid will be diluted to 0.5 mg/ml to result in about 350 ppb heavy metal content, assuming 1 ppm=about 1 mg/ml) on the basis of weight of the aluminium hydroxide liquid. The limit of acceptable heavy metal content may also be expressed in relation to the weight of the aluminium-salt such as the aluminium hydroxide in solution (referred to also as "starting aluminium compound"). The acceptable heavy metal content in this example then may not exceed 7 microgram of heavy metal for each gram of aluminium hydroxide solution (i.e. about 7 ppm), i.e. the ALHYDROGEL® 2% solution. As indicated herein above the aqueous composition comprising the protein preferably (such as e.g. if used as a vaccine) comprises between 0.1 to 2.5 mg/ml of the aluminium compound. The concentration of heavy metal in the aqueous composition however should according to the invention not exceed 350 ppb, i.e. about 350 ng per ml of the final composition and thus the selection or preparation of the starting aluminium compound has to be made accordingly. In order to further illustrate the selection of an appropriate starting aluminium compound solution (e.g. in the form of a concentrated solution (see above ALHYDROGEL® 2%=10 mg/ml), it is shown that an aluminium compound solution of 10 mg/ml aluminium hydroxide having about 7 ppm heavy metal impurities corresponds to a concentration of heavy metal in the protein composition when the aluminium concentration is about 0.1 mg/ml of about 70 nanogram/ml or 70 ppb (so well below the 350 ppb provided as the limit of the heavy metal content as taught by the invention). A concentration of 2.5 mg/ml of the aluminium hydroxide in the final aqueous composition starting with an aluminium solution of 10 mg/ml aluminium hydroxide having about 7 ppm heavy metal impurities will result in a heavy metal content in the aqueous protein composition that corresponds to a concentration of heavy metal of about 1.75 microgram/ml or about 1,750 ppm (so well above the 350 ppb provided as the limit of heavy metal content as taught by the invention).

A method of preparing an aqueous composition comprising a protein preferably further comprises packaging aliquots of said aqueous composition having less than 350 ppb heavy metal based on the weight of the aqueous composition in separate air-tight storage containers. The protein in the air-tight storage containers is stable and can be stored for at least three months, such as e.g. 4, 5, 6, 7, 8, 9, 10, 11, 12, 13, 14, 15, 16, 17, 18, 19, 20, 21, 22, 23, 24 months, preferably 20 or 24 months, more preferably 20 months at a temperature of between 2 to 8° C. degrees Celsius.

Without being bound to theory, antigen degradation in aqueous compositions, such as immunogenic composition, comprising heavy metal ions present in an aluminium salt, such as aluminium hydroxide, might be explained with an underlying degradation pathway assuming free-radicals such as e.g. free-radicals of sulphite. Formation of free radicals can be catalysed by heavy metal ions present in, for instance, aluminium hydroxide and this effect (in case of a certain amount of heavy metal as indicated according to the invention) could be the underlying root cause mechanism for stability issues as identified as part of the inventive contribution. The experimental part of this application shows in great detail the evidence of this root cause for the Japanese encephalitis vaccine (also referred to as "JEV") and makes a similar showing for a simple aluminium adjuvanted polypeptide composition that comprises a reactive compound such as sulphite. Thus, it is evident that similar reaction may occur also in other aqueous composition comprising aluminium (with high, e.g. higher than 350 ppb based on the weight of the composition, heavy metal content), protein and possibly a reactive component such as sulphite and/or other radical forming particles. Heavy metal-catalysed oxidation is a degradation pathway resulting in covalent modification of proteins. The modified physicochemical properties of the oxidized/modified protein or antigen may result in loss of biological activity (Li et al., 1995; Mayo et al., 2003; Stadtman, 1990).

The following reaction schemes (as possibly occurring in the JEV product as described in the experimental part) are indicative for compositions of the invention comprising in addition to the protein and the heavy metal also sulphite such as e.g. sulphite and formaldehyde.

Sodium-metabisulphite ($Na_2S_2O_5$) in solution dissolutes into bisulphite ($S_2O_5^{2-}$), in an alkaline solution the bisulphite equilibrium is towards sulphite ($SO_3^{2-}$) and in an acidic solution towards $H_2SO_3/SO_2$. After dissolution of $Na_2S_2O_5$ in water, it is hydrolysed into $NaHSO_3$ as follows $$Na_2S_2O_5 \Leftrightarrow 2NaHSO_3$$

At neutral pH we can assume the following equilibrium:

$$HSO_3^- \Leftrightarrow H^+ + SO_3^{2-} \quad pKa=7.2$$

This means that at pH 7 the equilibrium is shifted towards HSO3- and at more basic conditions (e.g. pH 8) towards $SO_3^{2-}$.

Formaldehyde forms a bisulphite adduct during neutralization according to the following equation:

$$CH_2O + HSO_3^- \rightarrow CH_2(OH)(SO_3)^-$$

After bisulphate is used up, the reaction proceeds until equilibrium is reached as follows:

$$CH_2O + SO_3^{2-} + H_2O \rightarrow CH_2(OH)(SO_3)^- + OH^-$$

Formaldehyde and sulphite react with each other, however, formaldehyde and sulphite have been found to be still present in equilibrium in the JEV vaccine and can be detected in the following range (n=49):

| Release Results in DS | Free Sulphite | Free Formaldehyde |
|---|---|---|
| Average (ppm) | 113.9 | 41.9 |
| Average (mM) | 1.41 | 1.36 |
| Standard deviation (ppm) | 24 | 14.3 |
| Min (ppm) | 66 | 10.6 |
| Max (ppm) | 174 | 78.7 |

According to the literature (Ranguelova et al., 2010), transition metal ions catalyse the auto-oxidation of (bi) sulphite via sulphur trioxide anion radical ($.SO_3^-$) formation:

$$M^{n+} + SO_3^{2-} \rightarrow M^{(n-1)+} + .SO_3^-$$

where M may be copper ($Cu^{2+}$), iron ($Fe^{3+}$), oxivanadium ($VO^{2+}$), manganese ($Mn^{2+}$), Nickel ($Ni^{2+}$) or chromate anion ($CrO_4^{2-}$) (Alipazaga et al. 2004; Berglund et al. 1993; Brandt and Elding 1998; Lima et al. 2002; Shi 1994).

It was shown that such sulphite radicals are highly reactive and can oxidize various substances, such as ascorbate, Hydroquinone and Histidine (Huie at al., 1985). A review of free radical chemistry of sulphite was published by Neta & Huie, 1985. The authors also show that radical formation can be also catalysed by photoionization of sulphite as follows:

$$SO_3^{2-} + h\nu \rightarrow .SO_3^- + e^-$$

Radical formation catalysed by light might also explain differences observed in potency and ELISA results of unlabeled naked syringes (used for release testing and reference purposes) and fully packaged final vaccine lot samples for the JEV product. Fully packed samples are completely protected from light, whereas unlabeled syringes might be exposed to light during storage and handling.

An important reaction of the sulphite radical in autooxidation systems is with molecular oxygen to form a peroxyl radical which is much more reactive:

$$.SO_3^- + O_2 \rightarrow .SO_5^-$$

The solubility of $O_2$ in water at 0° C. and 20° C. is 0.4 mM and 0.25 mM, respectively. Assuming that $O_2$ solubility in a composition of the invention is in a similar range, a considerable amount of oxygen is present to form the peroxyl radical. This radical is a much stronger oxidant compared to $.SO_3^-$ and can oxidize certain substrates which are not attached by $.SO_3^-$ at all and which, in fact, can form radicals that oxidize sulphite ions. In such cases, when the redox potential of the substrate is intermediate between those of $.SO_3^-$ and $.SO_5^-$, a reaction chain is likely to develop in presence of $O_2$ following the general pattern:

$$.SO_3^- + O_2 \rightarrow .SO_5^-$$

$$.SO_5^- + X \rightarrow SO_5^{2-} + .X^+$$

$$.X^+ + SO_3^{2-} \rightarrow X + .SO_3^-$$

The intermediacy of a substrate X may enhance the chain process of sulphite oxidation by oxygen. The one-electron reduction of $.SO_5^-$ yields $HSO_5^-$ (peroxymonosulfate), a very strong oxidant that is capable to oxidize many organic compounds (Lambeth et al., 1973; Ito & Kawanashi, 1991). Peroxymonosulfate is also a precursor sulphate anion radical $.SO_4^-$.

$$.SO_5^- + HSO_3^{\bullet} \rightarrow .SO_4^-. + HSO_4^-$$

The $.SO_4^-$. radical is a very strong oxidant, nearly as strong as the hydroxyl radical (.OH), and is very likely to oxidize other biomolecules by one-electron oxidation.

In a preferred embodiment, the composition comprising a protein according to the invention is a therapeutic composition or an immunogenic composition, such as a vaccine. Therapeutic compositions are administered to individuals, such as a human or an animal. In particular for such compositions, it is important that the protein within the composition still has its therapeutic effect at the time it is administered to said individual. Degradation of the protein or changes to the protein in its structure may result in the protein to lose its therapeutic activity. Similarly, degradation or structural changes of the immunogenic composition will also lead to a reduction in the effectivity of the composition in inducing and/or boosting an immune response in an individual. An immunogenic composition is preferably administered to an individual to counteract or prevent a viral or bacterial infection. Protein contained within the aqueous immunogenic composition can be a single protein or a multimeric protein or part of a complex comprising said protein (e.g. such as part of a virus or a cell, e.g. bacterial cell). In a preferred embodiment said complex comprises a live attenuated or inactivated virus or bacterium or a immunogenic viral or bacterial protein or an immunogenic part of such protein (e.g. an immunogenic peptide). If said immunogenic composition is administered to provide protection against a viral or bacterial infection, degradation of protein may result in loss of protective capability of the immunogenic composition. The term "immunogenic viral or bacterial protein" refers to a viral or bacterial protein which is capable of eliciting an immune response. The term "immunogenic part" as used herein refers to a part of a viral or bacterial protein which is capable of eliciting an immune response. Preferably the immune response elicited recognizes both said part of the protein and the entire protein. Therefore, in one embodiment, an aqueous composition comprising a protein according to the invention is an immunogenic composition. Said composition is preferably a therapeutic composition and/or prophylactic composition such as a vaccine. Also provided is a vaccine that is an aqueous composition comprising a protein according to the invention.

An "immunogenic composition" is herein defined as a composition that is capable of eliciting an immune response when administered to an individual. The elicited immune response can be humoral, cellular or a combination thereof and includes, but is not limited to, the production of antibodies, B cells such as activated B cells, and T cells such as activated T cells. An immune response as used herein is preferably directed specifically to one or more immunogens within a composition comprising a protein according to the invention. An immunogenic composition of the present invention can be administered to an individual by any technique known in the art including, but not limited to, intramuscular (IM), intradermal (ID), subcutaneous (SC), intracranial (IC), intraperitoneal (IP), or intravenous (IV) injection, transdermal, oral, intranasal, or rectal administration, and combinations thereof, preferred are intramuscular (IM), intradermal (ID), subcutaneous (SC), intracranial (IC), intraperitoneal (IP), or intravenous (IV) injection. In a preferred embodiment an immunogenic composition comprising a protein according to the invention is used for eliciting an immune response that may be useful in chronic setting (such as cancer treatment) or prophylactic setting (such as a typical vaccine). It is preferred that the immunogenic composition is used as a vaccine, i.e. prophylactic use. In this embodiment the aluminium is typically present as the adjuvant.

An "adjuvant" as used herein refers to a pharmacological or immunological agent that modifies the effect of other agents, such as an immunological agent that increases the antigenic response. Adjuvants typically serve to bring the antigen—the substance that stimulates the specific protective immune response—into contact with the immune system and influence the type of immunity produced, as well as the quality of the immune response (magnitude or duration); decrease the toxicity of certain antigens; and provide solubility to some vaccines components.

An "individual" is herein defined as a human or an animal. Individuals include but not limited to chickens, ducks, geese, turkeys, swans, emus, guinea fowls and pheasants, humans, pigs, ferrets, seals, rabbits, cats, dogs and horses. In a preferred embodiment of the invention an individual is a mammal, preferably a human.

An aluminium adjuvant is often prepared by controlled exposure of an aqueous solution of aluminium ions, to alkaline conditions (for review see, Lindblad, E B (2004) Immunol. and Cell Biol. Vol 82: 497-505). In the present invention it has been found for the JEV product (see experimental part) that a large amount of the heavy metal in this aqueous solution of aluminium ions ends up in the aluminium salt precipitate for the aluminium adjuvant. It has further been found that the amount of heavy metal in the aluminium precipitate affects the stability of the vaccine during storage of the vaccine. The amount of heavy metal that is present in the aluminium-salt can thus be controlled by determining the amount of heavy metal in the salt but also, and preferably, by controlling the amount of heavy metal in the aqueous solution of aluminium ions. The invention thus further provides a method for preparing a clinical grade aluminium-salt precipitate for incorporation into a medicament and/or vaccine, said method comprising preparing an aqueous solution of aluminium ion and precipitating said aluminium-ions from said solution, and determining the level of a heavy metal in the solution and/or the aluminium-salt precipitate, preferably wherein said solution and/or the aluminium-salt precipitate is determined to comprise an amount that results in less than 350 ppb heavy metal in the final composition e.g. when re-suspended in the final composition.

Also provided is a pharmaceutical composition comprising a protein according to the invention, optionally further comprising a pharmaceutically acceptable carrier and/or diluent. "A pharmaceutically acceptable diluent" as used herein is defined as any solution, substance or combination thereof that has no biologically or otherwise unwanted activity, meaning that it can be administered to an individual together with other components of an immunological composition without causing a substantial adverse reaction. Examples of suitable carriers for instance comprise keyhole limpet haemocyanin (KLH), serum albumin (e.g. BSA or RSA) and ovalbumin. In one preferred embodiment said suitable carrier comprises a solution, like for example saline.

In one aspect, a method according to the invention is used for prolonging the storage life or shelf life of an aqueous composition comprising a protein according to the invention. As used herein, the term "shelf life" is defined as the period of time a composition comprising a protein according to the invention can be stored without becoming unsuitable for use, for instance due to degradation of protein (e.g. is within the potency specification of the composition, e.g. vaccine, as required by the regulatory agency that approved or will approve the vaccine). During storage of aqueous compositions as described herein, degradation of the protein may occur, in particular when a certain level (as described herein) of heavy metals is exceeded. Degradation generally increases with time when such aqueous compositions are stored. Now that it is found that degradation of protein is reduced in an aqueous composition comprising in addition to said protein an aluminium-salt, if said composition comprises less than 350 ppb heavy metal based on the weight of the aqueous composition, it has become possible to counteract degradation of protein in aqueous compositions. By counteracting degradation of protein with a method according to the invention, the stability of said protein within said composition is increased and the storage life of an aqueous compositions comprising said protein is prolonged. An aqueous composition according to the present invention provides the advantage that it is stable and does not undergo degradation of protein during a prolonged period. Such aqueous composition comprising a protein according to the invention is stable for at least one month at elevated temperature such as e.g. 20 or 37° C., preferably for at least three months at elevated temperature such as e.g. 20 or 37° C.

An aqueous composition comprising a protein according to the invention is preferably stored at a temperature of between 0° C. and 20° C. to contribute to an increased shelf life, more preferably between 2° C. and 15° C., more preferably between 2° C. and 10° C., most preferably between 2° C. and 8° C. The shelf life at temperature between 2° C. and 8° C. is stable preferably for at least three months such as e.g. 4, 5, 6, 7, 8, 9, 10, 11, 12, 13, 14, 15, 16, 17, 18, 19, 20, 21, 22, 23, 24 months, preferably 20 or 24 months, more preferably 20 months at a temperature of between 2 to 8° C. degrees Celsius. Provided is thus an aqueous composition comprising a protein according to the invention having a shelf life of around 12 to 24 months. The invention further provides an aqueous solution according to the invention which has been stored for at least one month, preferably for at least two months, more preferably for at least three months, more preferably for at least six months.

As used herein "a stable protein composition" means that when compared to a starting composition not more than 50%, preferably not more than 40%, even more preferably not more than 30%, even more preferably not more than 20%, even more preferably not more than 10, even more preferably not more than 5% of the protein in said composition is degraded. "Degraded" in this context refers to any detectable modification of the protein when compared to the protein in the starting composition. For instance, a decrease in detection of the protein with a monoclonal antibody such as e.g. an antibody recognizing a neutralizing epitope is suitable and can be measured with any method known in the art, such as ELISA (see Example 4). The level detected can for instance be compared with the level detected with a polyclonal specific for the same protein such as e.g. representing the amount of total protein (changed or unchanged). Also provided is a method of prolonging the shelf life of an aqueous composition comprising a protein and an aluminium-salt, said method comprising selecting and/or preparing an aluminium-salt resulting in an aqueous composition with a heavy metal content of less than 350 ppb based on the basis of weight of the aqueous composition and combining said aluminium salt, said protein and water to produce said aqueous composition.

Further provided is a method of improving the shelf life reproducibility of preparations of aqueous compositions comprising a protein and an aluminium-salt, said method comprising obtaining at least two different aluminium-salt preparations, determining the amount of at least one heavy metal in said aluminium-salt preparations, selecting from said aluminium-salt preparations, aluminium-salt preparations that comprise less than 350 ppb of said at least one heavy metal; and combining aluminium salt of said selected preparations with said protein and water to produce said aqueous compositions.

In another aspect the invention provides a method for analysing the storage stability of a composition comprising aluminium and a therapeutic or prophylactic compound, said method comprising combining into a composition a predetermined amount of therapeutic or vaccine and a predetermined amount of an aluminium salt, said method further comprising storing said composition for at least 2 weeks, preferably at least 4 weeks and preferably at least one month, at a temperature of more than 20° C., preferably at a temperature of about 22° C. and determining the stability and/or the amount of protein, preferably therapeutic or prophylactic compound, in said composition. As demonstrated in Examples 1 and 2, a temperature of 22° C., which is higher temperature compared to normal storage conditions or about 2-8° C., results in accelerated degradation of protein in an aqueous composition comprising protein, an aluminium-salt and more than 350 ppb of said heavy metal based on weight with respect to said composition. Thus, a temperature of about 22° C. and a storage duration of at least 2 weeks, preferably at least 4 weeks, are suitable to determine the storage stability of aqueous compositions comprising a protein according to the invention. The storage stability can be determined by any method known in the art. The storage stability of an aqueous composition comprising a protein according to the invention is preferably analyzed by determining the storage stability of said protein, preferably by determining a storage sensitive epitope on said protein. For instance, as described in Example 1 and 2, the stability of a protein, preferably an antigen, is determined by determining the ratio of intact storage sensitive epitope, such as intact antigenic epitope (e.g. epitope of a neutralizing epitope) content, and total protein content. "Intact storage sensitive epitope" or "intact antigenic epitope" as used herein means that degradation has not occurred within said epitope. The intact antigenic epitope content is for instance measured by determining protein bound to a monoclonal antibody specifically directed against said epitope in, for example, an ELISA. The total protein content is for instance measured by determining protein bound to polyclonal antibody which is directed against various epitopes within the protein, for example by ELISA. The relative specific epitope content can then be expressed as the ratio of the total antigen content determined by binding to monoclonal antibody divided by total antigen content determined by binding to polyclonal antibody. A high ratio indicates high antigenic epitope content and a low ratio indicates a low antigenic epitope content. A low ratio measured for an aqueous composition after storage at least 20° C., preferably 22° C., for at least 2 weeks, preferably 4 weeks, as compared to the ratio measured for said aqueous composition before storage, indicates that structural changes have taken place within the antigenic epitope. Structural changes within said antigenic epitope indicate reduced storage stability of the aqueous composition.

The heavy metal content of an aqueous composition prepared according to the invention is less than 350 ppb based on the weight of the aqueous composition. Generally, the less heavy metal such aqueous composition contains, the less degradation of protein occurs. Preferably, therefore, the heavy metal content is less than 325 ppb based on the weight of the aqueous composition, more preferably less than 300 ppb, more preferably less than 275, more preferably less than 250 ppb and more preferably less than 235 ppb based on the weight of the aqueous composition.

As used herein the term "heavy metal" refers to the total amount of elements that exhibit metallic properties and includes the transition metals, metalloids, lanthanides, and actinides. Transition metals are elements whose atom has an incomplete d sub-shell, or which can give rise to cations with an incomplete d sub-shell, and include zinc, molybdenum, cadmium, scandium, titanium, technetium, palladium, vanadium, chromium, manganese, iron, cobalt, rhodium, hafnium, copper, nickel, yttrium, niobium, zirconium, ruthenium, silver, tantalum, rhenium, tungsten, osmium, meitnerium, platinum, iridium, mercury, bohrium, seaborgium, hassium. Metalloids are Boron (B), Silicon (Si), Germanium (Ge), Arsenic (As), Antimony (Sb), Tellurium (Te), Polonium (Po). The lanthanides are the fifteen metallic chemical elements with atomic numbers 57 through 71, i.e. Lanthanum, Cerium, Praseodymium, Neodymium, Promethium, Samarium, Europium, Gadolinium, Terbium, Dysprosium, Holmium, Erbium, Thulium, Ytterbium and Lutetium. The actinides are the fifteen metallic chemical elements with atomic numbers from 89 to 103, actinium, thorium, protactinium, uranium, neptunium, plutonium, americium, curium, berkelium, californium, einsteinium, fermium, mendelevium, nobelium and lawrencium. Preferably said heavy metal is selected from the transitional metals. In another preferred embodiment, said heavy metal is a metal having a molar mass of between 21 and 83, more preferably from Cu, Ni, W, Co, Os, Ru, Cd, Ag, Fe, V, Cr, Pb, Rb and Mo. In an even more preferred aspect, the heavy metal is selected from the heavy metals Cu, Ni, and Fe.

As demonstrated in the Examples, Aluminium hydroxide (Alum) Lot 4230 was identified to contribute significantly to antigen degradation in JEV vaccine FVL09L37. In Example 3 it is shown that this Alum lot comprises at least the following metals: Cu, Ni, W, Co, Os, Ru, Cd, Ag, Fe, V. Higher levels of Fe, Ni and Cu ions were noted in Alum lot 4230 when compared to other investigated lots. Lot 4230 was the only one where residual Cu ions were detected. Therefore, preferably said heavy metal is selected from the group consisting of Cu, Ni, W, Co, Os, Ru, Cd, Ag, Fe, V, more preferably from Fe, Ni and Cu.

The amount of heavy metal in an aqueous composition of the invention is defined herein above. This amount is typically for the total of determined heavy metals, or for the heavy metals Fe, Cr and Ni, or a combination thereof which constitute the major heavy metals by weight in the aqueous composition of the invention. For specific heavy metals different maximums amounts may be preferred. For instance, it is preferred that the amount of Fe in the aqueous composition of the invention is less than 350 ppb based on the weight of the aqueous composition. In a preferred embodiment the amount of Fe is less than 250 ppb Fe based on the weight of the aqueous composition.

There is strong evidence that many of the pro-inflammatory effects of aluminium adjuvants are mediated via the formation of reactive oxygen species (ROS). Aluminium can, under physiological conditions, promote the reduction of Fe(III) to Fe(II) and the oxidation of the latter. Thus the combination of Fe and Al in the adjuvant will potentiate the formation and activities of ROS (Exley, C (2010). Trends in Immunol. Vol. 31: pp 103-109). In the present invention it has been found that Fe can be present in an aqueous composition of the invention without significantly affecting the storage stability of the composition. In this embodiment of the invention it is preferred that the aqueous composition of the invention comprises between 5 ppb and 250 ppb Fe based on the weight of the aqueous composition. In these amounts the formation of ROS during storage due to the presence of such amount of Fe (if any ROS) does not significantly affect the storage stability of the aqueous composition as defined elsewhere herein. However, the amounts are sufficient to allow pro-inflammatory effects following administration of the vaccine in vivo.

In the present invention it has been found that particularly the presence of heavy metal Cu seriously affects the storage stability of the composition of the invention. In a particularly preferred embodiment an aqueous composition of the invention therefore comprises less than 3 ppb Cu based on the weight of the aqueous composition. Preferably less than 2.5 ppb. In a particularly preferred embodiment said aqueous composition comprises Cu at a level that is below the detection limit of the method for the detection of copper as described in the Examples.

In the present invention it has been found that particularly the heavy metal Ni affects the storage stability of the composition of the invention. In a particularly preferred embodiment an aqueous composition of the invention therefore comprises less than 40 ppb Ni based on the weight of the aqueous composition. Preferably less than 30 ppb, more preferably less than 20 pbb and more preferably less than 15 pbb Ni based on the weight of the aqueous composition. In a particularly preferred embodiment said aqueous composition comprises Ni at a level that is below the detection limit of the method for the detection of nickel as described in the Examples.

The heavy metal can be present in electronic neutral form or it can be ionised. Typically and preferably the heavy metal is present in ionic form in an aqueous composition of the invention.

Metal content of a composition can be determined in various ways. In one aspect, a method according to the invention comprises determining the level of a heavy metal in an aqueous composition and/or the aluminium-salt present in said aqueous composition. Methods for measuring the level of one or more heavy metals in an aqueous solution are known in the art. Examples of such methods inductively-coupled-plasma mass spectrometry (ICP-MS), flame atomic absorption spectrometry (F-AAS), and/or graphite furnace atomic absorption spectrometry (GF-AAS).

An example of an assay which can be used to determine the content of heavy metals is described in Example 3. The assay involves treating a sample of an aqueous solution containing an Aluminum-salt with concentrated $HNO_3$ under heat until a clear solution is obtained. The clear solution can then be further diluted and analyzed, for instance by ICP-MS, F-AAS and/or GF-AAS., for the presence and content of metal ions including Pb, Cd, Cr, Co, Fe, Cu, Ni, Ag, W and Al.

Examples 1 and 2 demonstrate that the JEV antigen shows higher stability at pH 7.5-8 as compared to pH 7. In the Examples antigen stability is expressed as the ratio of monoclonal/polyclonal ELISA. The monoclonal antibody used (clone 52-2-5) was shown to recognize a neutralizing epitope in the Japanese Encephalitis Vaccine (JEV). The relative specific epitope content can be expressed as the ratio of the total antigen content determined by "monoclonal ELISA" divided by total antigen content determined by "polyclonal ELISA". Without being bound to theory, the effect of a higher antigen stability at pH 7.5-8 can be explained based on the underlying assumed complex reaction chemistry of sulphites. pH might influence the related to equilibrium reaction conditions of the sulphite/formaldehyde reaction and surface charge of certain proteins/amino acid side chains accessible to modification. The pH may affect oxidation by direct influence on redox potentials of the amino acid residues and the oxidizing agents, e.g. free radicals. Therefore, in one embodiment, a method according to the invention comprises buffering said aqueous composition at a pH of between 7.5 and 8.5.

Various aluminium salts are being used in compositions for administration of an individual. Aluminium adjuvant typically contains an aluminium oxide or sulphate or a combination thereof. In a preferred embodiment the aluminium salt comprises aluminiumoxide ($Al_2O_3$), aluminiumhydroxide ($Al(OH)_3$) or aluminiumphosphate ($AlPO_4$).

In a preferred embodiment the aqueous composition of the invention further comprises a reactive compound. Typically though not necessarily the reactive compound is present as a result of a manipulation of the aqueous composition, for instance to treat or inactivate infectious agent if any in the composition. The reactive compound can also be present for another reason. Sulphite, for instance, is sometimes present to inactivate any residual formaldehyde in the aqueous solution. Formaldehyde is typically a chemical that is often used to inactivate any infectious agent.

The reactive compound is preferably a redox active compound, radical building compound and/or a stabilizing compound. In a preferred embodiment said aqueous composition of the invention comprises formaldehyde, ethanol, chloroform, trichloroethylene, acetone, TRITON™ X-100 (Polyethylene glycol tert-octylphenyl ether), deoxycholate, diethylpyrocarbonate, sulphite, $Na_2S_2O_5$, beta-proprio-lacton, polysorbate such as TWEEN® 20 (Polysorbate 20) or, TWEEN® 80 (Polysorbate 80), $O_2$, phenol, PLURONIC (poloxamer) type copolymers, or a combination thereof.

Sulphite is preferably present in an amount of between 0.1 mM and 5 mM, or preferably between 0.5-2 mM. Formalin is preferably present in an amount of between 0.1 mM and 5 mM, more preferably between 0.5 mM and 2 mM. Oxygen is preferably present in an amount that is equivalent to the solubility of $O_2$ at the measured temperature, $O_2$ is preferably present in an amount of between 10 and 250 uM when measured at 20 degrees Celsius. When measured at a temperature of 0 degrees Celsius $O_2$ is preferably present in an amount of between 10 and 400 uM. A stabilizing compound is preferably present in an amount of between 10 and 400 uM. Similarly a redox active compound is present in an amount of between 0.1 mM and 5 mM, or preferably between 0.5-2 mM. A radical building compound is preferably present in an amount of between 0.1 mM and 5 mM, or preferably between 0.5-2 mM. In this context and for the sake of clarity it is important to note that redox active compound, the radical building compound and/or the stabilizing compound is consumed in the production of a radical, whereas the heavy metal is indicated herein above, is a catalyst in the production of a radical and is not consumed, as such. The redox active compound, the radical building compound and/or the stabilizing compound is therefore not a heavy metal.

The total amount of redox active compound, the radical building compound and/or the stabilizing compound although small in absolute amounts can still be significant in relation to the antigen or protein in the aqueous composition of the invention. The antigen/protein is preferably present in an amount of between 0.1 nmol to 1 umol, more preferably between 1 nmol and 100 nmol.

The concentration of protein, preferably a therapeutic or vaccine protein, in an aqueous composition comprising a protein according to the invention is preferably between 1 ng/ml and 10 mg/ml, preferably between 10 ng/ml and 1 mg/ml, more preferably between 100 ng/ml and 100 ug/ml, such as between 1 ug/ml and 100 ug/ml. The concentration is preferably at least 1 ng/ml to ensure that the therapeutic or vaccine protein is in a concentration sufficient to exert its therapeutic effect when administered to an individual. The concentration should, however, preferably not exceed 10 mg/ml in order to prevent or reduce the occurrence of possible side effects associated with administration of said protein to an individual. In particular, the concentration of viral protein in an aqueous composition according to the invention comprising JEV is preferably between 0.01 μg/ml and 1 mg/ml, more preferably between 0.1 μg/ml and 100 ug/ml. In an exemplary embodiment, of the invention, an aqueous composition according to the invention comprises about 10 ug/ml of JEV. The dose of a single administration of an aqueous composition comprising a protein, preferably a therapeutic or vaccine protein, according to the invention is preferably between 0.1 ml and 10 ml, preferably between 0.5 ml and 5 ml, such as 0.5 ml, 1 ml, 1.5 ml, 2 ml, 2.5 ml, because such dose allows for convenient administration to an individual, such as a human.

A method according to the invention is preferably used to increase stability of an immunogenic composition, preferably a vaccine, comprising an aluminium-salt based adjuvant. Non-limiting examples of such vaccines are those directed against infection with *Bacillus anthracis* (causing Anthrax), *Corynebacterium diphtheriae* (causing diphtheria), *Clostridium tetani* (causing tetanus), *Pseudomonas* such as *Pseudomonas aeruginosa, Staphylococcus* such as *Staphylococcus aureus* or *Staphylococcus epidermidis, Haemophilus influenzae* type B bacteria (Hib), polio virus, hepatitis A virus, hepatitis B virus, Human Papillomavirus, influenza virus, Japanese encephalitis virus, Rotavirus, Rickettsiae bacteria (causing Typhus), yellow fever virus, Varicella Zoster Virus, Meningococcus, or combinations thereof, such as, but not limited to, DTP (diphtheria, tetanus, polio). An aqueous composition comprising a protein according to the invention therefore preferably comprises a protein which is a viral or bacterial protein, preferably a protein of *Bacillus anthracis, Corynebacterium diphtheriae, Clostridium tetani, Haemophilus influenzae* type B bacteria (Hib), polio virus, hepatitis A virus, hepatitis B virus, Human Papillomavirus, influenza virus, Japanese encephalitis virus, Rotavirus, Rickettsiae bacteria, yellow fever virus, Varicella Zoster Virus and/or Meningococcus. In a preferred embodiment, said protein contained in a composition comprising a protein according to the invention is a viral protein from a virus of the Flaviviridae family, preferably of a Japanese encephalitis virus (JEV). As demonstrated in the Examples, the stability of aqueous compositions comprising a JEV protein, an aluminium-salt and comprising less than 350 ppb heavy metal based on the weight of the aqueous composition, and in particular wherein the amount of Cu is less than 3 ppb based on the weight of the aqueous composition, is increased as compared to aqueous composition comprising more than 350 ppb of heavy metal and more than 3 ppb of Cu. Thus, a method according to the invention is particularly suitable to increase stability of an aqueous composition comprising a JEV protein.

In another preferred embodiment or aspect of the invention, said protein contained in a composition comprising a protein according to the invention is a bacterial protein from a bacterium of the *Pseudomonas* family, preferably of *Pseudomonas aeruginosa*. As demonstrated in the Examples, the stability of aqueous compositions comprising *Pseudomonas aeruginosa* fusion protein (SEQ ID NO: 1) and an aluminium-salt is reduced when more than 350 ppb heavy metal based on the weight of the aqueous composition is present.

An aqueous composition comprising a protein according to the invention is particularly suitable for use as an immunogenic composition or vaccine. For instance, such compositions are particularly useful for immunize an individual to treat or prevent a viral or bacterial infection. In one embodiment, the invention therefore provides a method for the treatment of an individual comprising obtaining an immunogenic aqueous composition comprising a protein and an aluminium-salt, said aluminium-salt having less than 350 ppb heavy metal based on the weight of the aqueous composition, preferably less than 3 ppb of Cu, and administering the immunogenic aqueous composition to an individual in need thereof. Also provided is a method for the prophylactic treatment of an individual comprising obtaining an immunogenic aqueous composition comprising a protein and an aluminium-salt, said aluminium-salt having less than 350 ppb heavy metal based on the weight of the aqueous composition, preferably less than 3 ppb of Cu, and administering the immunogenic aqueous composition to an individual in need thereof. Further provided is a method for inducing and/or boosting an immune response towards an antigen in an individual, said method comprising obtaining an aqueous composition comprising a protein comprising said antigen and an aluminium-salt, said aluminium-salt having less than 350 ppb heavy metal based on the weight of the aqueous composition, preferably less than 3 ppb of Cu, and administering the aqueous composition to an individual in need thereof. In another aspect the invention provides a method for immunizing an individual comprising administering to said individual at least two immunogenic compositions at an interval of at least two weeks between each administration, and wherein each of said at least two immunogenic compositions comprise the same antigen, and wherein at least one of said immunogenic compositions further comprises an aluminium salt having less 350 ppb heavy metal based on the weight of the aqueous composition, preferably less than 3 ppb of Cu, and administering the immunogenic aqueous composition to an individual in need thereof. Nucleic acid compositions are sometimes also administered together with aluminium. Thus for the present invention it is possible to replace "protein" in an aqueous composition of the invention with nucleic acid. Thus in one embodiment the invention provides a method for preparing an aqueous composition comprising aluminium and a nucleic said method comprising—combining an aluminium-salt, said nucleic acid and water to produce said aqueous composition and—determining the level of a heavy metal in the aqueous composition and/or the aluminium-salt. The invention also provides a method for preparing an aqueous composition comprising aluminium and a nucleic acid said method comprising—preparing or selecting an aluminium-salt having less 350 ppb heavy metal based on the weight of the final aqueous composition, preferably less than 3 ppb of Cu, and administering the immunogenic aqueous composition to an individual in need thereof and combining said aluminium salt, said nucleic acid and water to produce said aqueous composition. In a preferred embodiment said methods further comprising buffering said aqueous composition at a pH of between 7.5 and 8.5. In a particularly preferred embodiment said methods, further comprise packaging aliquots of said aqueous composition having less than 350 ppb heavy metal based on the weight of the aqueous composition in separate air-tight storage containers. The nucleic acid may be administered for therapeutic purposes. For instance, in the form of an antisense RNA, RNAi or mimic thereof. The nucleic acid may also be administered in the form of an infectious agent, typically a virus or a modified virus, as is the case in many gene therapy approaches. In that case the nucleic acid is enclosed in a particle that comprises protein. The invention thus further provides an aqueous composition comprising a nucleic acid and an aluminium-salt, said composition comprising less than 350 ppb heavy metal based on the weight of the aqueous composition.

The invention is further explained in the following examples. These examples do not limit the scope of the invention, but merely serve to clarify the invention.

REFERENCES

Alipazaga M V, Moreno R G M, Coichev N. 2004. Synergistic effect of Ni(II) and Co(II) ions on the sulphite induced autoxidation of Cu(II)/tetraglycine complex. Dalton Trans 13:2036-2040.

Arunee Wittayanukulluk, Dongping Jiang, Fred E. Regnier, Stanley L. Hem, "Effect of microenvironment pH of aluminum hydroxide adjuvant on the chemical stability of adsorbed antigen", Vaccine 22 (2004) 1172-1176.

Berglund J, Fronaeus S, Elding L I. 1993. Kinetics and mechanism for manganese-catalyzed oxidation of sulfur (IV) by oxygen in aqueous solution. Inorg Chem 32:4527-4538.

Brandt C, Elding L I. 1998. Role of chromium and vanadium in the atmospheric oxidation of sulfur (IV). Atmos Environ 32(4):797-800.

Exley, C (2010). Trends in Immunol. Vol. 31: pp 103-109.

Ito, Kimiko and Kawanashi, Shosuke. Site-specific fragmentation and modification of Albumin by sulphite in presence of metal ions or peroxidase/$H_2O_2$: Role of Sulphate radical. Biochem and Biophys Res Comm., 1991, 176, 1306-1312.

Huie R. E., Neta P. One-electron redox reaction in aqueous solutions of sulphite with hydroquinone and other hydroxyphenols. J. Phys. Chem., 1985, 89 (18), 3918-3921.

Kalina Ranguelova, Marcelo G. Bonini, and Ronald P. Mason: (Bi)sulphite Oxidation by Copper,Zinc-Superoxide Dismutase: Sulphite-Derived, Radical-Initiated Protein Radical Formation. Environmental Health Perspectives 2010, 118 (7), 970-975.

Lampeth D. O., Palmer G. The kinetics and mechanism of reduction of electron transfer proteins and other compounds of biological interest by dithionite. J. Biochem. Chem. 1973, 248, 6095-6103.

Li S, Schöneich C, Borchardt R T. Chemical instability of protein pharmaceuticals: Mechanisms of oxidation and strategies for stabilization. Biotechnol Bioeng. 1995 Dec. 5; 48(5):490-500.

Lindblad, E B (2004) Immunol. and Cell Biol. Vol 82: 497-505.

Lima S, Bonifacio R L, Azzellini G C, Coichev N. 2002. Ruthenium(II) tris(bipyridyl) ion as a luminescent probe for oxygen uptake on the catalyzed oxidation of $HSO_3^-$. Talanta 56:547-556.

Mayo J C, Tan D X, Sainz R M, Natarajan M, Lopez-Burillo S, Reiter R J. Protection against oxidative protein damage induced by metal-catalyzed reaction or alkylperoxyl radicals: comparative effects of melatonin and other antioxidants. Biochim Biophys Acta. 2003 Mar. 17; 1620(1-3): 139-50.

Neta P., Huie R. E.: Free Radical Chemistry of Sulphite. Environmental Health Perspectives 1985, 64, 209-217.

Shi X. 1994. Generation of $.SO_3^-$ and OH radicals in $SO_3^{2-}$ reactions with inorganic environmental pollutants and its implications to $SO_3^{2-}$ toxicity. J Inorg Biochem 56(3): 155-165.

Stadtman E R. Metal ion-catalyzed oxidation of proteins: biochemical mechanism and biological consequences. Free Radic Biol Med. 1990; 9(4):315-25.

BRIEF DESCRIPTION OF THE DRAWINGS

FIG. 14: Amino acid sequence of Ala-(His)6-OprF190-342-OprI21-83 (SEQ ID NO: 1)—herein also referred as "protein A".

EXAMPLES

Example 1

Figure 1:
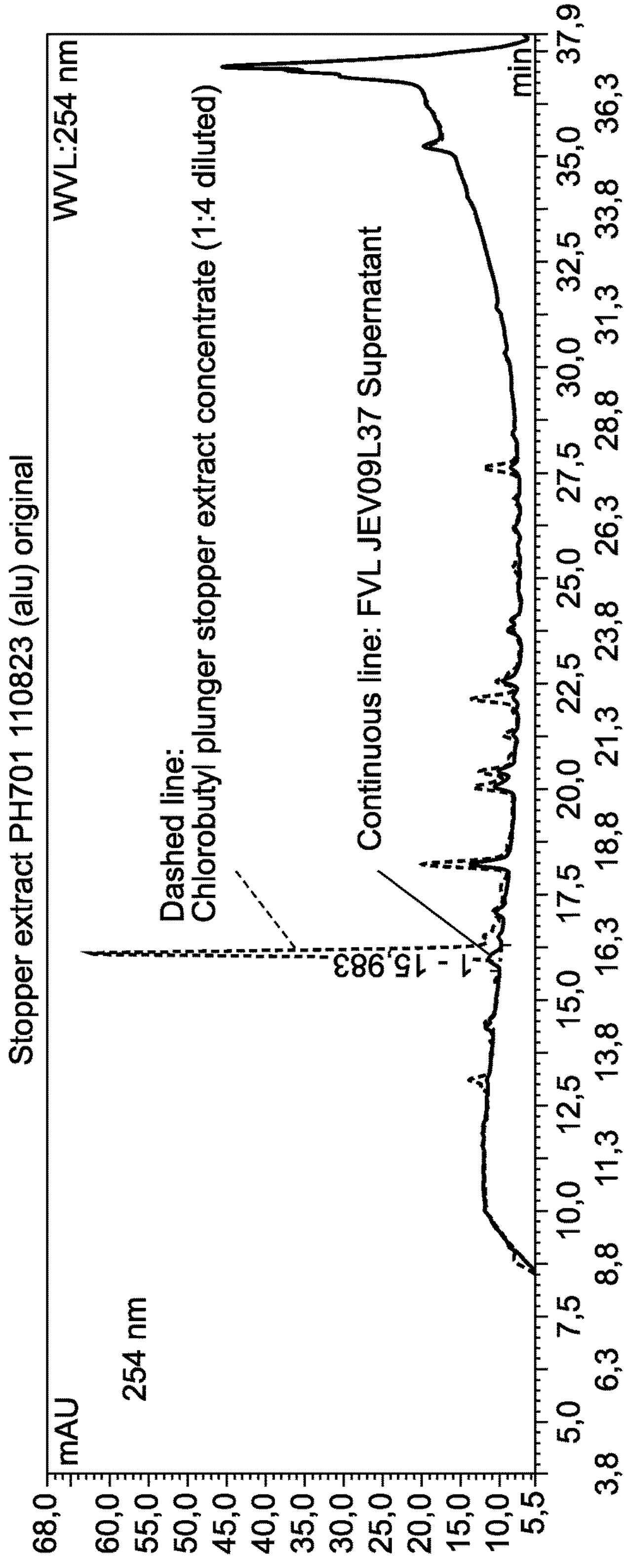
FIG. 1: RP-HPLC elution profiles of chlorobutyl stopper extract (1:4 diluted) and JEV09L37 SN.

Aluminium hydroxide (Alum) Lot 4230 was previously identified to contribute significantly to antigen degradation in FVL09L37. In this particular Alum lot much higher residual metal ion content was observed compared to other Alum lots used for formulation of the inactivated JEV antigen. This Example demonstrates additional studies carried out to further identify the underlying root-cause mechanism and influence of metal ions on degradation pathway of JEV. Design of experiments (DOE) was performed to work out the influence of individual parameters on antigen stability.

Parameters tested in a 25 full factorial DOE were

Aluminium hydroxide Lot 4230 vs. Aluminium hydroxide Lot 4074

Presence of excess Protamine sulfate fragments

Presence of leachables from chlorobutyl rubber stopper pH range 7 to 8

Residual formaldehyde content

Alum lot 4230 contains much higher levels of residual metal ion impurities compared to other Alum lots used for formulation of JEV. A "Design-of-Experiment" (DOE) was selected to further investigate the potential root cause mechanism and interaction of parameters that finally could lead to product degradation. In factorial designs, multiple factors are investigated simultaneously during the test. As in one factor designs, qualitative and/or quantitative factors can be considered. The objective of these designs is to identify the factors that have a significant effect on the response, as well as investigate the effect of interactions (depending on the experiment design used). Predictions can also be performed when quantitative factors are present, but care must be taken since certain designs are very limited in the choice of the predictive model. For information about DOE in general see (Siebertz, Karl; van Bebber, David, Hochkirchen, Thomas: Statistische Versuchsplanung: Design of Experiments (DoE). Publisher: Springer Berlin Heidelberg; 1st Edition (2010), ISBN-10: 3642054927).

1.1 DOE Study Design 1.1.1 Definition of Parameters and Levels for DOE Design

The following parameters and levels were taken into consideration for designing an appropriate DOE experiment:

Residual metal ion content of Alum: Aluminium hydroxide Lot 4230 and Lot 4074 were selected as representative of the two extremes quality with regard to residual metal ions content of Aluminium hydroxide. The center point was a mixture of 50/50% of both Alum lots. Initial analysis for remaining metal ion impurities in 2% Aluminium hydroxide stock solution by ICP-MS showed significant differences in Cr, Fe, Ni and Cu ion content between these two lots (see Table 1).

Protamine Sulphate fragments: Protamine sulfate (PS) fragments are present at low quantity (<5 µg/mL) in the final vaccine lot. It was tested if PS fragments could contribute to virus surface modification (e.g. interaction/covalent linkage to the virus surface proteins) in combination with Alum and other factors used in this study. Therefore a stock solution of PS fragments was prepared by digestion with Trypsin followed by heat inactivation and ultrafiltration using a 5 kDa membrane for protease inactivation and removal of the enzyme. This stock solution was used for spiking additional PS fragments into the respective formulations at the high level of 50 µg/mL. In low level samples no additional PS fragments were spiked and the actual level in formulations was <5 µg/mL according to HPLC analysis.

pH: Lower and upper level of pH in formulations was 7 and 8 with the center point at pH 7.5.

Leachables/Extractables from syringe plunger: Syringe plungers (made of chlorobutyl PH701/50 black) that are currently used in the container closure system. It was tested if leachables from the chlorobutyl rubber in the formulation could contribute to antigen modification. Therefore a stock solution of leachables was prepared and used for spiking experiments. The high level of spiked leachables in formulation was estimated to be on average 1.4× higher compared to commercial Final Vaccine Lot (FVL). Due to the harsh extraction conditions additional peaks were detected not present in FVL samples. Therefore the spiked formulations represent a "worst case" with regard to leachables and extractables. Formulations at the low level did not contain any leachables from chlorobutyl rubber.

Residual formaldehyde: For low level formulations no additional formaldehyde was spiked into the formulation samples. The lower level was the residual formaldehyde that was still present in diluted NIV sample after inactivation/neutralization and 2-fold dilution was in the range of approx. 37 ppm (recalculated from commercial DS release GMP analytical certificate). For the high level additional 40 ppm formaldehyde were spiked into the corresponding formulation (total final content approx. 77 ppm). It was tested if residual formaldehyde in combination with higher level of metal ions present in Alum 4230 and possible other factors could further react with the virus leading to hyper-cross linking of surface proteins and loss of relevant epitopes.

Determination of Other Residual Process Related Impurities:

Residual formaldehyde, sulphite and sucrose in final formulations were estimated based on GMP certificates for commercial drug substance JEV11A74. Results were recalculated by the actual 2-fold dilution of NIV to DS used within the DOE experiments.

Residual Sulphite: The concentration of residual sulphite was constant in all formulations with approx. 93 ppm.

Residual sucrose: The concentration of residual sucrose was constant in all formulations with approx. 1% v/w.

1.1.2 DOE Design

These 5 factors were combined in a 25 DOE plan resulting in a total number of 34 experiments including 2 center points with the following base design. DOE planning and evaluation were carried out with an appropriate software (Statgraphic Plus 3.0)

Base Design: Factorial 25
Number of experimental factors: 5
Number of blocks: 1
Number of responses: 1
Number of centerpoints per block: 2
Number of runs: 34
Error degrees of freedom: 18
Randomized: Yes

| Factors | Low | High | Units | Continuous[1)] |
|---|---|---|---|---|
| pH | 7.0 | 8.0 | | Yes |
| Alum[2)] | 0.0 | 100.0 | Alum 4230% | Yes |
| Spiked PS Fragments[3] | 0 | 50 | µg/mL | No |
| Spiked leachables [4)] | 0 | 1.4 | relative content compared to FVL | No |
| Spiked Formaldehyde[5)] | 0 | 40 | ppm | No |

-continued

| Responses | Units |
|---|---|
| ELISA (monoclonal, polyclonal) of desorbed antigen | AU/mL |

[1)]Continuous means that a center point (mean value from high and low level) is present in the study design. No Center point means that only low and high levels are present in the study design.

[2)]Low level (0%) means that formulation was prepared with Alum Lot 4074. High level (100%) means that formulation was prepared with Alum lot 4230. For center point formulations an equal mixture (50/50%) of both Alum lots was used.

[3]Since PS is present in NIV used for preparation of drug product samples, actual PS concentration in non-spiked formulations was <5 µg/mL and ~50-55 µg/mL for PS-spiked formulations.

[4)] No leachables were assumed in non-spiked formulations since samples were prepared/stored in low-bind Eppendorf tubes. Total content of leachables from chlorobutyl rubber syringe plunger in spiked samples was approx. 1.4 times higher compared to FVL.

[5)]Actual formaldehyde concentration in non-spiked DP samples was approx. 37 ppm, total formaldehyde concentration in spiked samples was approx. 77 ppm.

2 Definitions & Abbreviations

AcCN Acetonitrile
DOE Design of experiments
DS Drug substance
FVL Final Vaccine lot
HPLCHigh performance liquid chromatography
ICP-MS Inductively-coupled-plasma mass spectrometry
PS Protamine sulphate
RP Reversed Phase
SEC Size exclusion chromatography
SN Supernatant
TFA Trifluoroacetic acid
w/o without

3 Materials and Methods 3.1 DOE Studies 3.1.1 Materials

- Syringe plunger stoppers: PH701/50/C black Sil6 7002-1051 (obtained from West, Order No. 2116)
- 100 mL Glass bottle (Schott)+Teflon coated screw cap
- Aluminium foil
- HQ water
- Electrical water bath (IKA, HBR 4 digital)
- LoBind Eppis 2 ml (Eppendorf, Cat. No. 0030 108.132)
- Speed Vac (Christ, RVC-2-25)
- HPLC vials, clear glass, 900 µL, Chromacol (VWR, Cat. no.: 548-1124)
- HPLC vials, PP, 900 µL, (Agilent, Item no. 5182-0567)
- Caps for HPLC vials, pre-cut (VWR, Cat. no.: 548-1260)
- 15 ml Falcon tubes (Greiner, Cat. No. 188724)
- Alum batch 4470 (RQCS 1342); Alum Lot 4230 (RQCS 1200)
- 10×PBS (Gibco, Order No. 14200-091)
- Parafilm
- Waters Atlantis T3 column; 3 µm particle diameter; column diameter/length 2.1×100 mm (Order No. 186003718; Lot 0107372331)
- Acetonitril (Merck, Cat No. 1.13358.2500)
- TFA (Sigma, Order No. 302031
- HPLC system Dionex 3000
- Solvent Rack SR-3000
- Pump UltiMate-3000, analytical low pressure gradient pump
- Autosampler WPS-3000 TSL, analytical autosampler—temperature controlled
- Column compartment TCC-3200, temperature controlled PDA-Detector PDA-3000

Formaldehyde solution 37% Merck, Cat No. 1.040031000)

Protamine sulphate (Intercell Biomedical Ltd, Batch no. 086056)

Ultrafilatrion device (Amicon® Ultra 3 kDa) (Millipore, Cat No. UFC900324)

Incubator Infors HT Incubator Multitron Standard (Infor-sAG)

Trypsin (Sigma, Order No: T0303)

3.1.2 Procedure for Preparation of Extractables from Syringe Plunger

Syringe plunger (made of chlorobutyl PH701/50 black) that are currently used in the FVL container closure system were obtained from West (Germany). Therefore a stock solution of leachables was prepared by heat treatment of syringe plunger in water (90° C./2 h) followed by concentration in a speed-vac. The relative content of leachables in this stock solution was estimated by RP-HPLC using a C18 column (Atlantis T3 column) and compared to FVL JEVO9L37 supernatant.

Extraction Method

A 100 mL Schott glass bottle with a Teflon coated screw top and a piece of aluminum foil were washed with hot water and thoroughly rinsed with HQ water. 30 stoppers were filled in the bottle and 30 ml of HQ-water were added. The bottle was closed with the aluminum foil fitted between bottle and screw and sealed additionally with Parafilm. The bottle was heated in the water bath to 90° C. for 2 hours and allowed to cool to room temperature. The extract was transferred to 14 low-bind Eppendorf tubes (a total of 28 mL extract was recovered). Twelve vials (total of 24 mL) were concentrated in a Speed Vac for approximately 44 hours and pooled into a falcon tube to obtain 6 ml of 4× concentrated stopper extract. A control sample containing 30 mL HQ water w/o stopper was prepared in the same way to evaluate any possible contamination.

C18 RP-HPLC Method

Leachables were separated by RP-HPLC C18 column (Atlantis T3) operated at 40° C. and 0.25 mL/min. Solvent A was 0.1% TFA in 1120, solvent B was 0.1% TFA in AcCN. Separation was performed by linear gradient ranging from 0 to 95% B in 30 min. Detection was done at 214 nm, 254 nm and 280 nm. The total relative concentration of concentrated stopper extract was estimated to be 80 fold higher compared to peaks detected in Final Vaccine Lot supernatant (FVL SN; obtained by removal of Ahun particles by centrifugation at 5000 g/5 min) as detected at 254 nm. Therefore a total relative content of 80 U/mL (arbitrary Units U) were assigned for the stock solution, whereas the total relative concentration of leachables in FVL SN was set to 1 U/mL. For DOE studies, the stock solution was diluted 16-fold into the respective formulations yielding approx. 5 U/mL of total extractables.

3.1.3 Preparation of Protamine Sulfate Fragments

A stock solution of PS fragments was prepared by digesting a PS solution (2 mg/mL in PBS) with Trypsin (200 ng/mL for 60 min at 37° C.). The enzyme was subsequently inactivated by heat (90° C. for 10 min) followed by ultrafiltration using a 3 kDa membrane (Amicon® Ultra centrifugal filter). Due to the cut-off of the membrane Trypsin remained in the retentate, whereas the PS fragments were present in the permeate. Complete inactivation of the enzyme was evaluated by spiking 500 μg/mL of full length PS into an aliquot of the obtained PS fragment followed by incubation at 37° C. for 18 h. No degradation of full length PS was observed indication complete inactivation/removal of Trypsin. Degradation was monitored by PS-SEC HPLC.

3.1.4 DOE Plan

Samples were prepared according to the pipetting scheme as shown in Table 2. NIV Batch JEV11A74 obtained from a commercial production run was used as starting sample. NIV was diluted 2-fold to DS using PBS buffer followed by pH adjustment. 5 mL aliquots were removed and adjuvanted with the corresponding Alum lot 4230, 4074 or a 50/50% mixture of both. The final amount of Alum stock (2% A1203) added was 500 μg/mL Aluminium (0.1% A1203). Each formulation (5 mL) was split into two parts (2×2.5 mL) using Lo-bind Eppendorf tubes. One aliquot was stored at 2-8° C., another aliquot stored at 22±1° C. (Infors HT Incubator) under gentle shaking (20 rpm).

3.2 Inactivated JEV ELISA (Polyclonal Based)

Desorption of the antigen from Alum and ELISA analysis was carried out using polyclonal sheep anti JEV antibodies for coating the 96 well ELISA plates as described in Example 4.

3.3 Inactivated JEV ELISA (Monoclonal Based)

A monoclonal (mAb) based JEV ELISA was developed. The assay is primarily based on the "polyclonal JEV ELISA" assay format, only a monoclonal anti-JEV antibody (clone 52-2-5) is used for coating. The employed mab 52-2-5 was shown to be specific for JEV and to recognize a neutralizing epitope. Mab clone 52-2-5 was obtained by subcutaneously immunizing BALB/c mice with commercially available vaccine lot JEV08J14B. Spleen cells of the mice were fused to myeloma cells. From resulting hybridoma cells single clones were selected and sub-cloned. The clones were negatively screened against Bovine Serum Albumin, Protamine sulphate and an extract of the production cell line of the JE-vaccine (Vero cells). A positive screen was done against Neutralized Inactivated Virus (NIV) of vaccine lot JEV08M20. For screening, microtiter plates were coated with the relevant antigen and reacted with supernatant of cultures of the selected clones. For detection a goat anti mouse polyclonal antibody conjugated with alkaline phosphatase was used. Mab clone 52-2-5 was shown to recognize a neutralizing epitope on domain III of the envelope (E) protein of JEV containing Ser331 and Asp332 (Lin C.-W. and Wu W.-C. J Virol. 2003; 77(4):2600-6). Binding of the mab to the indicated neutralizing epitope is for instance determined as described in Lin and Wu (2003) by site-directed mutagenesis of the domain III at position 331 (for instance: S→R), and/or by alanine mutations at or near position 331 of domain III, for instance of residues Ser 331 and Asp332, followed by immunoblots to determine binding of the mab to the mutated proteins. Negative binding results indicate that the epitope of the mab is the neutralizing epitope identified by Lin and Wu (2003). The neutralizing characteristic of the epitope gives rise to the assumption that the epitope might be of importance for the antigen to elicit a protective immune response.

JEV samples were analyzed by both ELISA assays, polyclonal and monoclonal. The relative specific epitope content can be expressed as the ratio of the total antigen content determined by "monoclonal ELISA" (clone 52-2-5) divided by total antigen content determined by "polyclonal ELISA". Any differences in the ratio may indicate differences in specific epitope content 52-2-5. Results close to 1 would correspond to high epitope contents, and results close to 0 correspond to low relative epitope content. A low ratio indicates presence of structural changes of the neutralizing epitope.

In the course of development of this "mAb ELISA", differences between vaccines lots were detected, which could be correlated with potency results of these lots.

3.4 Protamine Sulfate SEC-HPLC

PS (full length) and its fragments were analyzed by size-exclusion HPLC (SEC-HPLC) using a Superdex Peptide 10/300 GL, 10×300 mm, 13 μm (GE Healthcare) using 0.1% (v/v) Trifluoroacetic acid (TFA) in 30% acetonitrile (CAN) as mobile phase at a flow rate of 0.6 mL/min. PS containing samples were prepared in duplicated, i.e. diluted with mobile phase before injection.

4 Results 4.1 Analysis of Stopper Leachables Used for Spiking Experiments

RP-HPLC elution profiles of concentrated stock solution obtained after extraction of stoppers under heat compared to FVL SN is shown in FIG. 1. Similar peak pattern as observed for both samples. Due to the harsh extraction conditions additional peaks were detected in the concentrate that were not present in FVL samples or present only at a much lower relative content Therefore the spiked formulations represent a "worst case" with regard to leachables and extractables. The total relative content of individual peaks in extract concentrate and spiked formulation in comparison to FVL SN is summarized in Table 3. The total amount of leachables in the stock solution was calculated as the sum of all peaks detected and expressed in arbitrary units as 67 U/mL. Since the stock solution was diluted 16 times into the respective formulation, the resulting total content of leachables was estimated as 4.2 U/mL. This corresponds on average 1.4 fold increase compared to FVL JEV09L37 supernatant (3.0 U/mL).

4.2 Analysis of Protamine Sulphate Fragments

Figure 2:
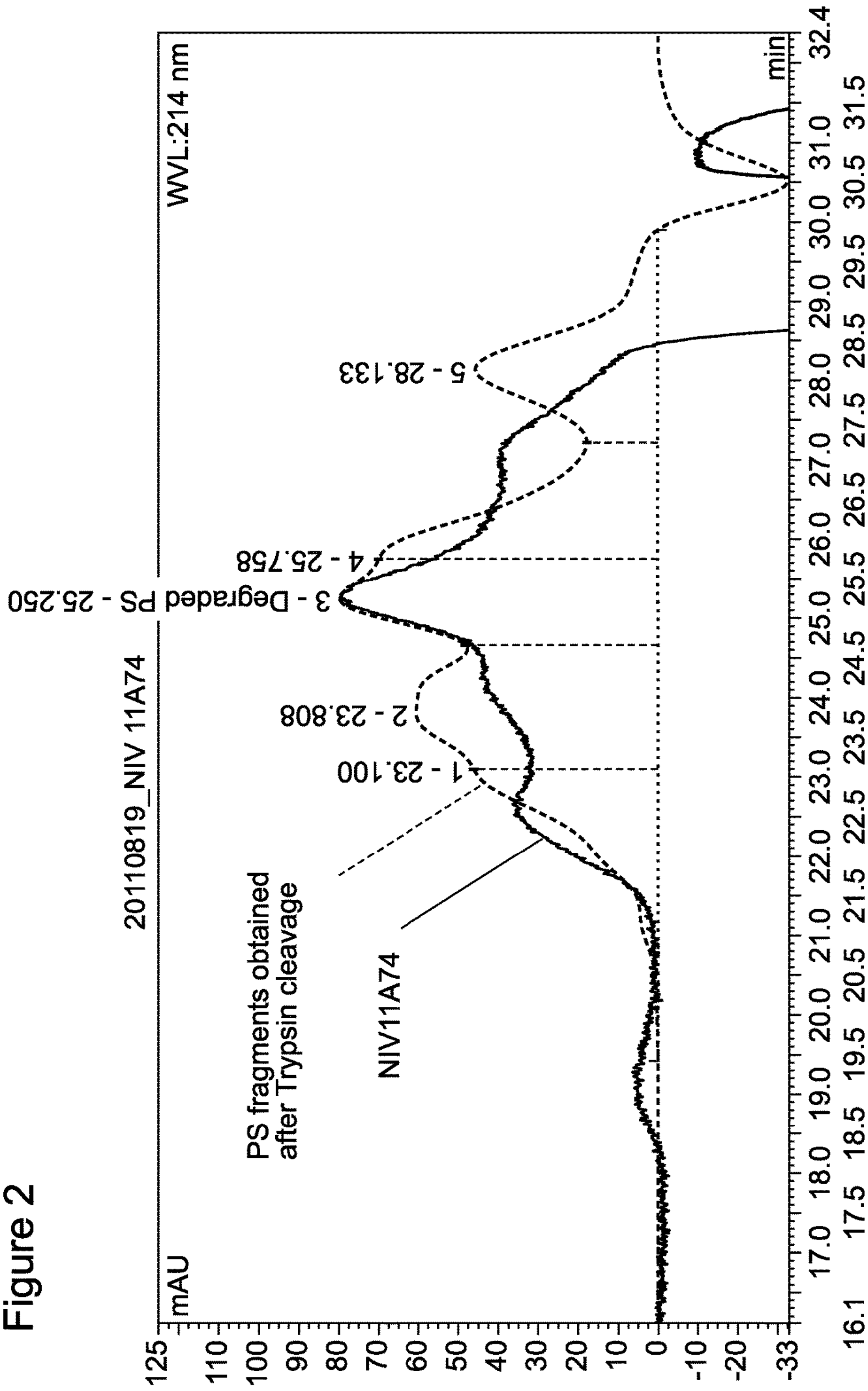
FIG. 2: SEC HPLC elution profiles of PS (2 mg/mL) before and after trypsin cleavage.
Figure 3:
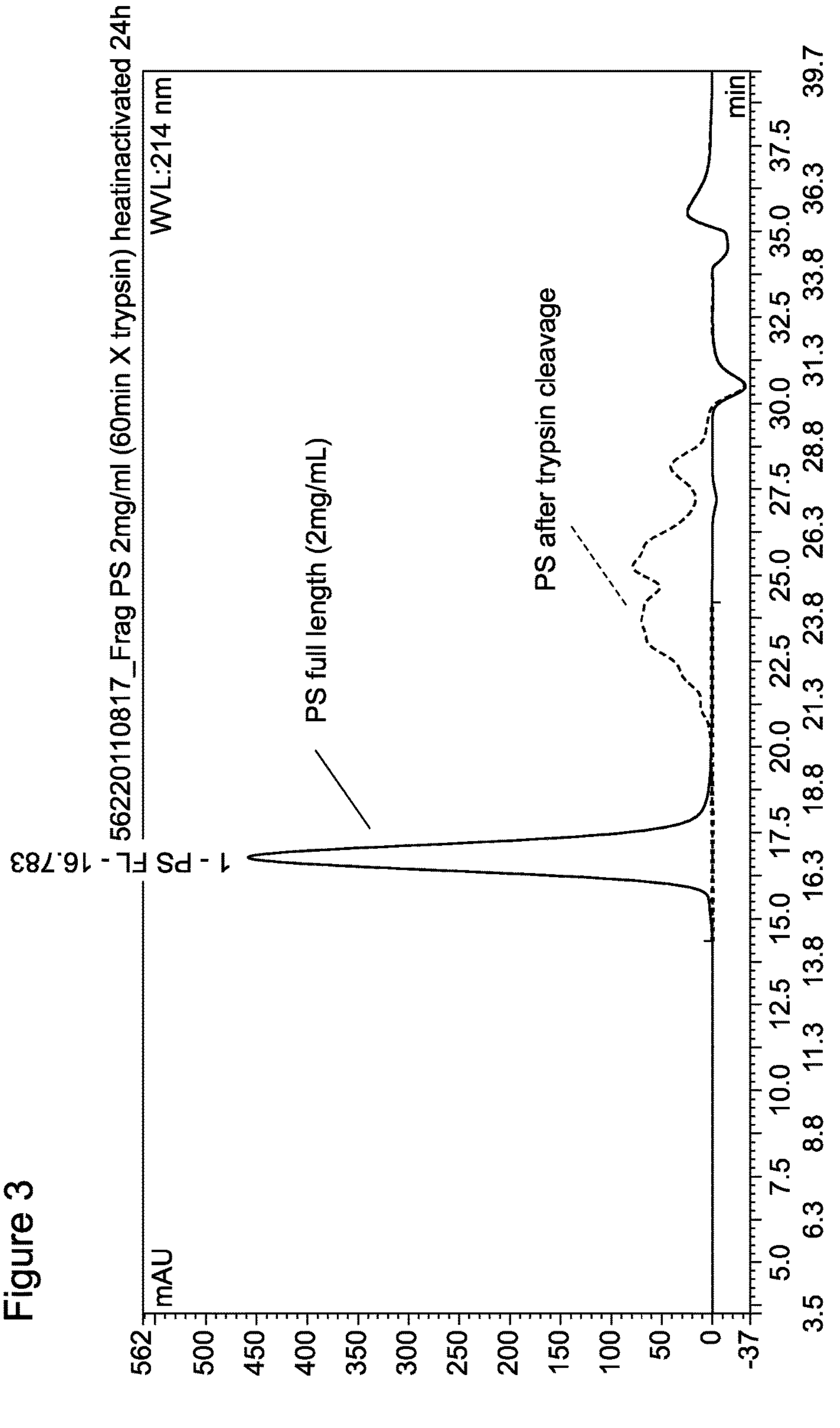
FIG. 3: SEC HPLC elution profiles of Trypsin treated PS and degraded PS as present in NIV11A74. Note that elution profiles were normalized to similar peak height to allow better comparison.

PS fragments obtained after cleavage of full length PS by Trypsin are shown in FIG. 2. Similar peak profiles of Trypsin treated PS and already degraded PS present in NIV11A74 were obtained by HPLC (see FIG. 3).

4.3 DOE Evaluation

Formulations prepared for this DOE were analyzed after 4 weeks and 8 weeks of incubation at accelerated conditions (22° C.). It was considered that any degradation reaction would be accelerated when stored at higher temperature compared to normal storage conditions (2-8° C.). However, samples are still stored at 2-8° C. and will be analyzed on a later time point (~4-6 month). First analysis of samples stored at 22° C. for 4 and 8 weeks are shown in the Table 4.

4.3.1 DOE Evaluation after 4 Weeks at 22° C.

Statistical evaluation of the DOE matrix results obtained after 4 weeks at 22° C. showed that the specific epitope content 52-2-5 (expressed as the ratio of desorbed antigen analyzed by monoclonal/polyclonal ELSIA) was statistically significant influenced (95% confidence level, see Table 5) by the following factors:

- lower specific epitope content 52-2-5 in presence of Alum lot 4230
- lower specific epitope content 52-2-5 at lower pH 7
- Higher specific epitope content 52-2-5 at increased concentration of formaldehyde Presence of higher concentration of PS fragments and chlorobutyl rubber leachables did not show any influence on specific epitope content. No 2nd or higher order interactions between individual parameters were detected.

Figure 4:
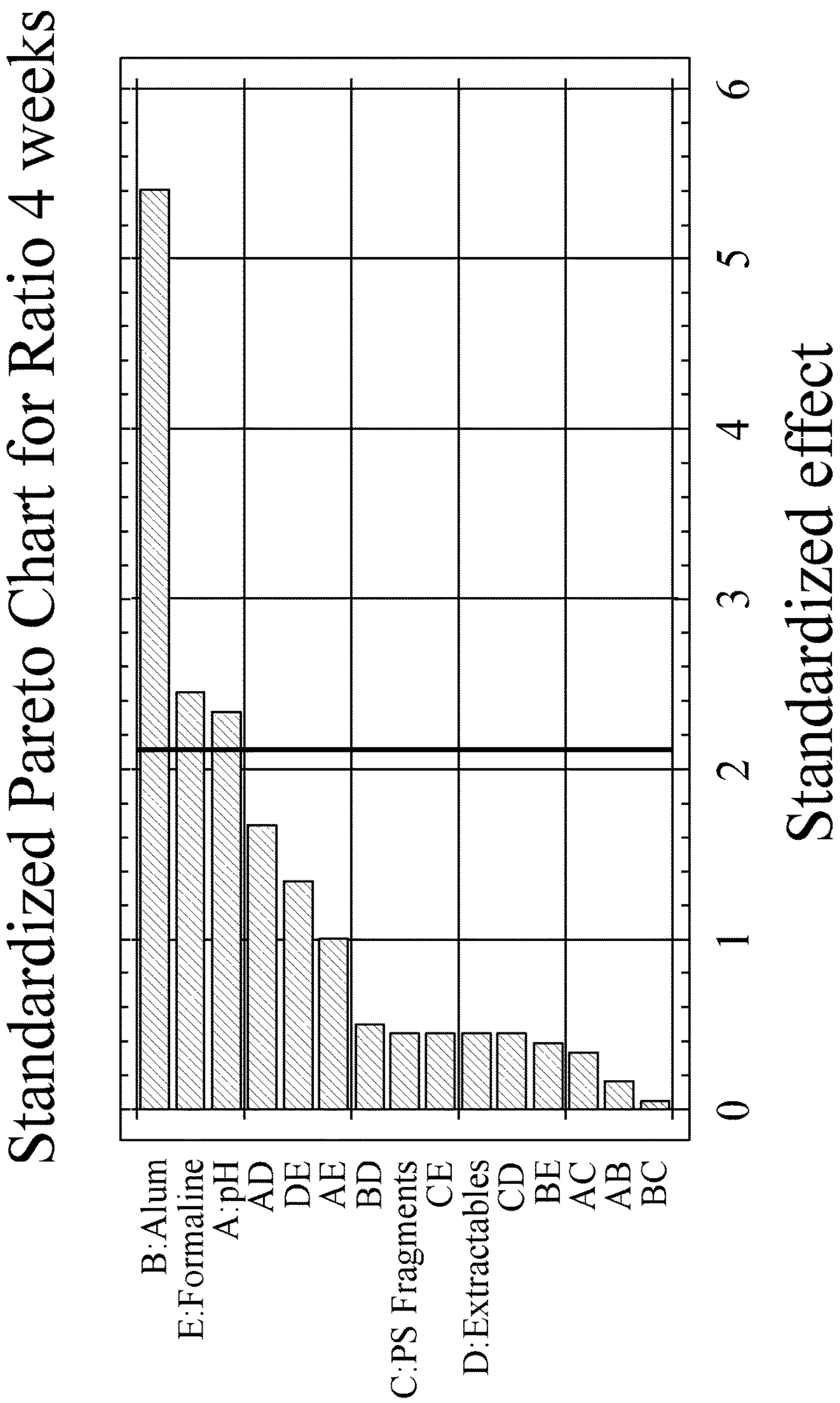
FIG. 4: DOE evaluation of the ratio monoclonal/polyclonal ELISA by Pareto chart analysis and main effects plots (4 weeks at 22° C.).
Figure 4:
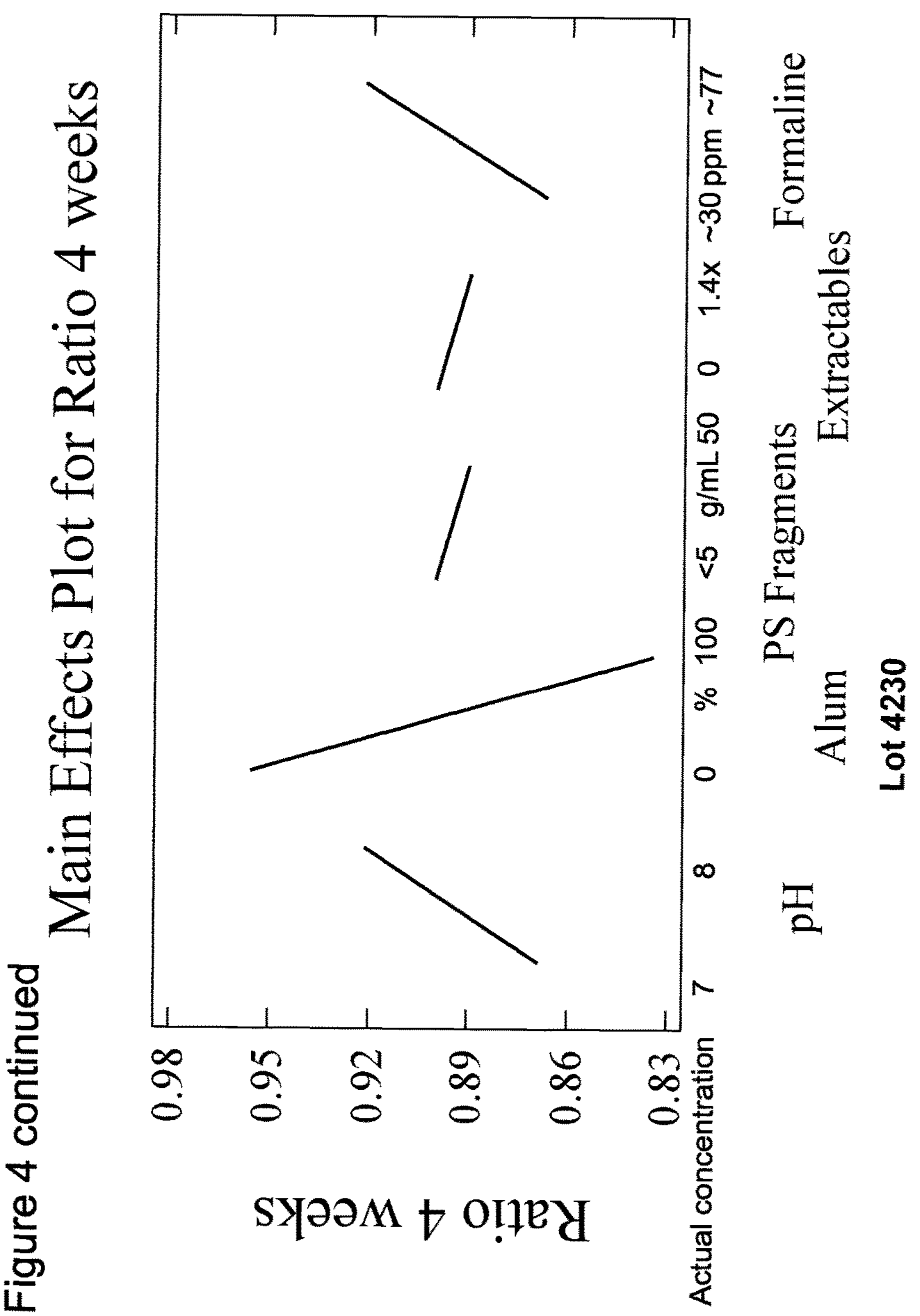

The ANOVA table partitions the variability in "Ratio 4 weeks" into separate pieces for each of the effects. It then tests the statistical significance of each effect by comparing the mean square against an estimate of the experimental error. In this case, 3 effects (Alum, pH, Formaldehyde) have P-values less than 0.05, indicating that they are significantly different from zero at the 95.0% confidence level. The R-Squared statistic indicates that the model as fitted explains 74.85% of the variability in Ratio 4 weeks. The adjusted R-squared statistic, which is more suitable for comparing models with different numbers of independent variables, is 51.27%. The standard error of the estimate shows the standard deviation of the residuals to be 0.063. The mean absolute error (MAE) of 0.0353 is the average value of the residuals. The Durbin-Watson (DW) statistic tests the residuals to determine if there is any significant correlation based on the order in which they occur in your data file. Since the DW value is greater than 1.4, there is probably not any serious autocorrelation in the residuals. Effects are also displayed by standardized Pareto chart and main effect plots as shown in FIG. 4.

4.3.2 DOE Evaluation after 8 Weeks at 22° C.

Statistical evaluation of the DOE matrix results obtained after 8 weeks at 22° C. were similar to results obtained after 4 weeks. Evaluation shows that the specific epitope content 52-2-5 (expressed as the ratio of desorbed antigen analyzed by monoclonal/polyclonal ELSIA) was statistically significant influenced (95% confidence level, see Table 6) by the following factors:

- lower specific epitope content 52-2-5 in presence of Alum lot 4230
- lower specific epitope content 52-2-5 at lower pH 7

Presence of higher concentration of PS fragments, chlorobutyl rubber leachables and formaldehyde did not show any influence on specific epitope content. Note that P-value for formaldehyde (P=0.08) is quite close to be significant. No 2nd or higher order interactions between individual parameters were detected.

Figure 5:
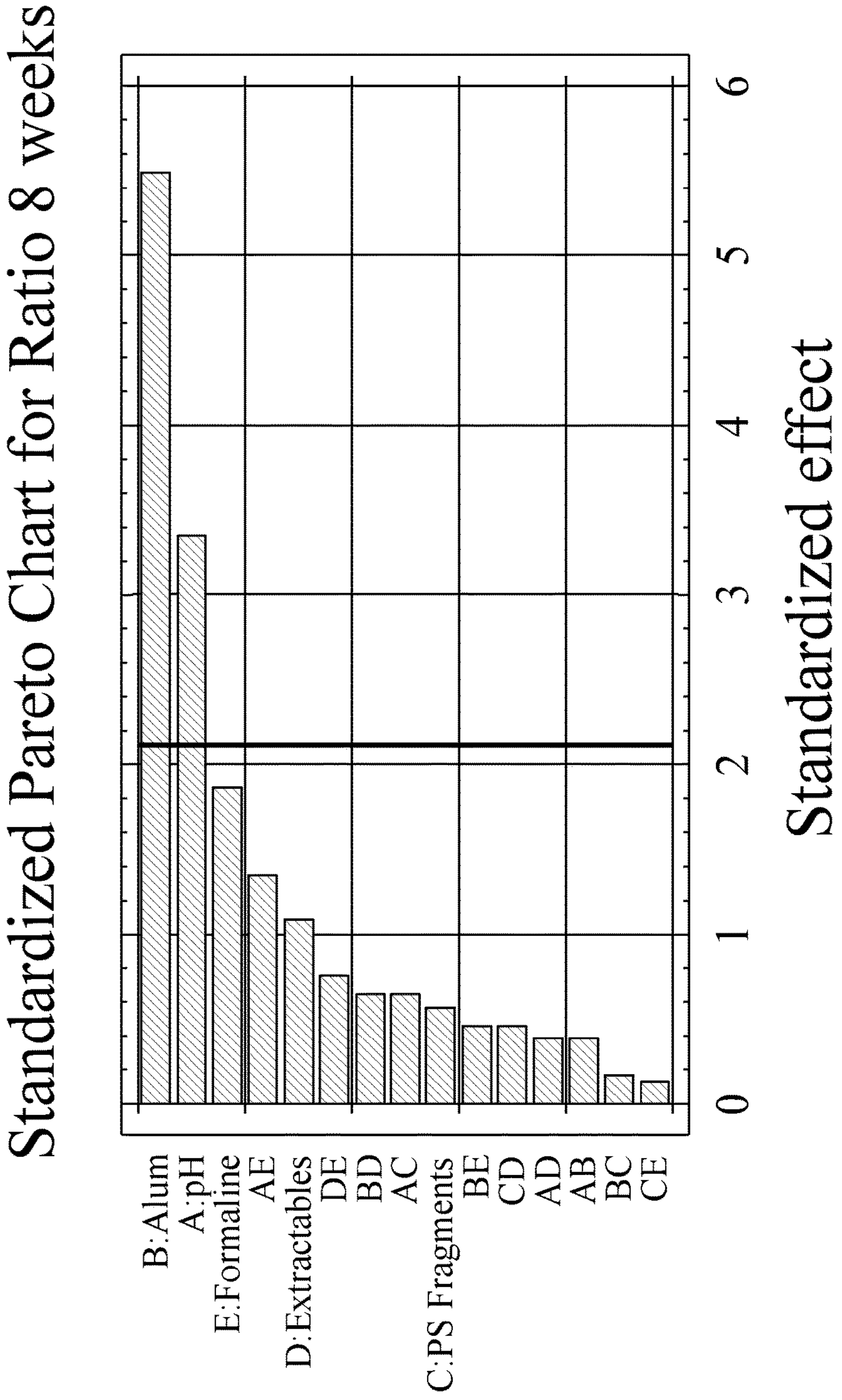
FIG. 5: DOE evaluation of the ratio monoclonal/polyclonal ELISA by Pareto chart analysis and main effects plots (8 weeks at 22° C.).
Figure 5:
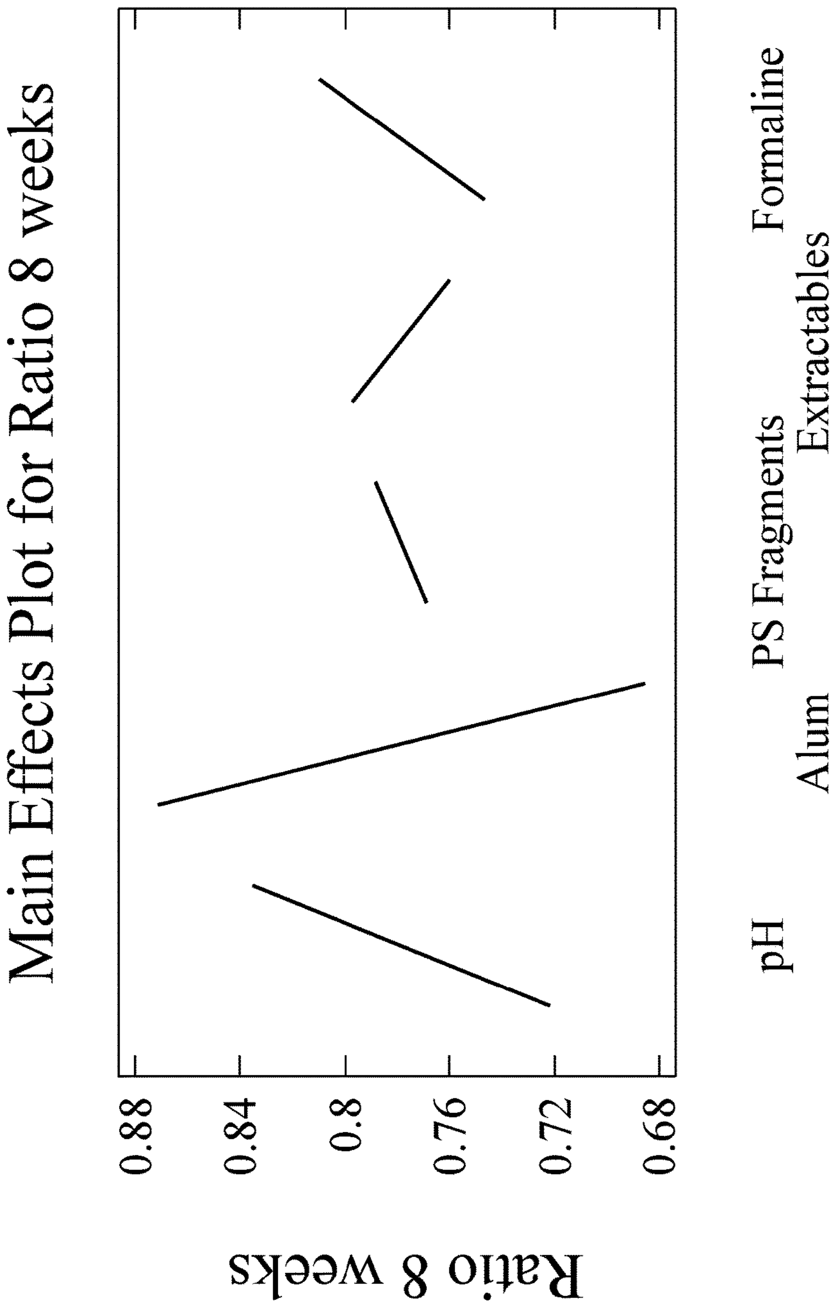

The ANOVA table partitions the variability in "Ratio 8 weeks" into separate pieces for each of the effects. It then tests the statistical significance of each effect by comparing the mean square against an estimate of the experimental error. In this case, 2 effects (Alum and pH) have P-values less than 0.05, indicating that they are significantly different from zero at the 95.0% confidence level. The R-Squared statistic indicates that the model as fitted explains 75.9% of the variability in "Ratio 8 weeks". The adjusted R-squared statistic, which is more suitable for comparing models with different numbers of independent variables, is 53.3%. The standard error of the estimate shows the standard deviation of the residuals to be 0.095. The mean absolute error (MAE) of 0.057 is the average value of the residuals. Effects are also displayed by standardized Pareto chart and main effect plots as shown in FIG. 5.

Figure 6:
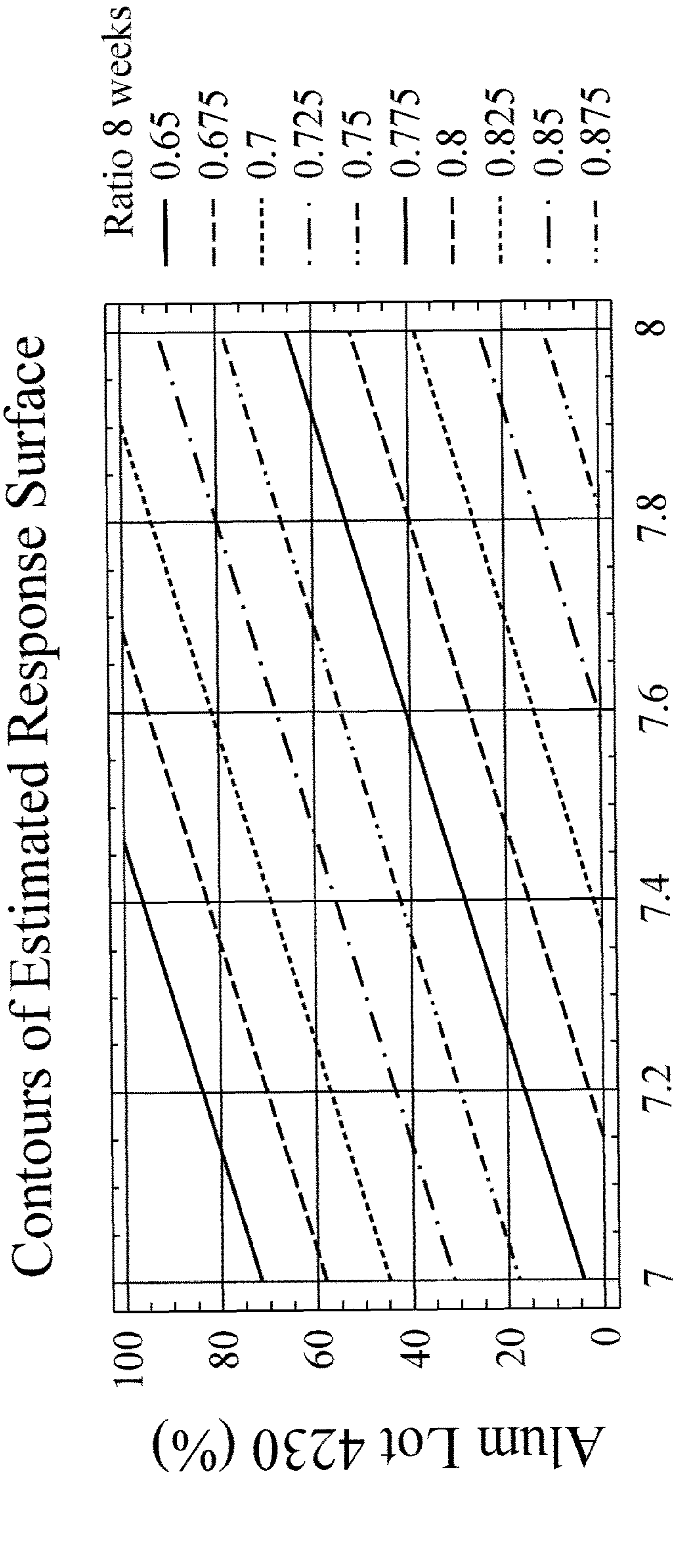
FIG. 6: Contour plot of the estimated response.
Figure 7:
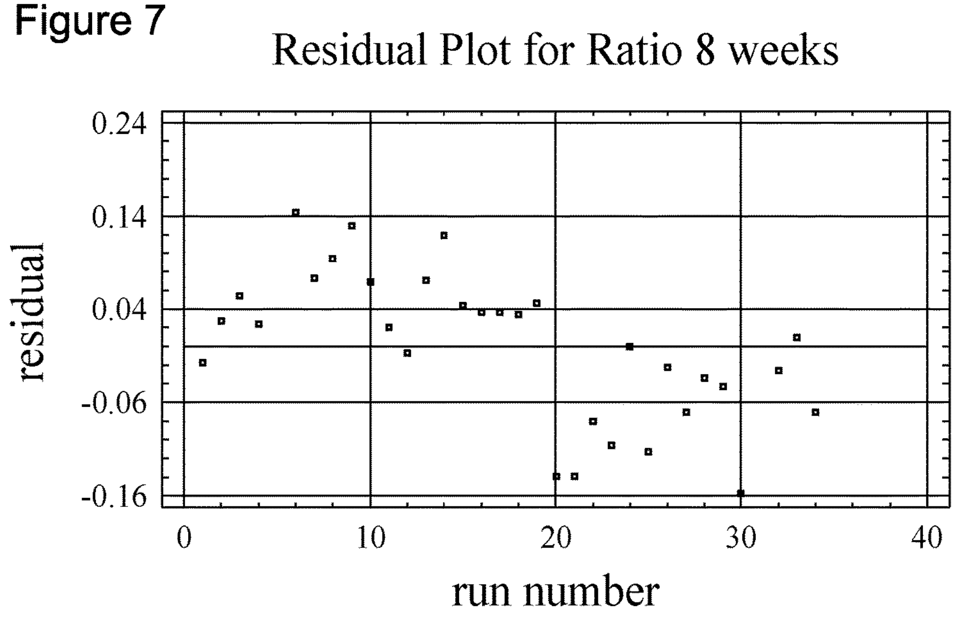
FIG. 7: Residual plot of the estimated response.

Regression analysis was also performed to the fitted data and calculated regression coefficients are shown in Table 7. The regression equation is displayed below which has been fitted to the data including pH, Alum and Formaldehyde. The equation of the fitted model is $$\text{"Ratio 8 weeks"}=0.0228125+0.113125*\text{pH}-0.00185625*\text{Alum}+0.0315625*\text{Formaldehyde}$$

where the values of the variables are specified in their original units, except for the categorical factors which take the values −1 for the low level and +1 for the high level. The contour of the estimated response and residual plot is shown in FIG. 6 and FIG. 7. The ratio increases when relative Alum content Lot 4230 decreases and pH increases.

Table 8 contains information about values of "Ratio 8 weeks" generated using the fitted model. The table includes:

(1) the observed value of "Ratio 8 weeks"
(2) the predicted value of "Ratio 8 weeks" using the fitted model
(3) 95.0% confidence limits for the mean response As shown the experimental results are well predicted by the regression model.

5 Summary

Out of the parameters tested, Alum lot 4230 was shown to contribute significantly to antigen degradation as analyzed by monoclonal/polyclonal ELISA under accelerated conditions (22° C., testing time points 4 and 8 weeks). DOE results obtained after 4 and 8 weeks at 22° C. show that Alum 4230 is the most significant factor with regard to antigen degradation as detected by the ratio of monoclonal/polyclonal ELISA. Formulations made with Alum 4074 (much higher purity with regard to residual metal ions) show in general much higher specific epitope content.

Formaldehyde and pH also contributed to antigen stability, but to a lower extent. The effect of increased antigen stability in samples formulated with Alum 4230 at higher formaldehyde level was well demonstrated (e.g. samples #19 and 29). However, influence of formaldehyde was less pronounced after extended storage period (8 weeks at 22° C.).

Better stability of the antigen was observed at pH 8 compared to pH 7. Protamine sulphate and leachables from chlorobutyl rubber stopper did not contribute to the antigen degradation.

Example 2

In previous studies (see Example 1) Aluminium hydroxide Lot 4230 was identified a significant contributing factor to the observed antigen degradation in FVL09L37. In this particular lot of Aluminium hydroxide (Alum), a much higher residual metal ion content was observed compared to other Alum lots used for formulation of the inactivated JEV antigen. This Example summarizes additional studies carried out to evaluate the influence of metal ions on stability of inactivated JEV. Spiking studies were conducted with the antigen either present in inactivated neutralized virus (NIV) solution or in drug product (DP) suspension following formulation of the antigen with Aluminium hydroxide.

1 Study Description

It was previously shown that Alum lot 4230 contains much higher levels of residual metal ion impurities compared to other Alum lots used for formulation of JEV (see also Example 3). Additional studies were performed to evaluate the influence of metal ions on the stability and on a potential surface modification of JEV. The inactivated antigen was either present in neutralized inactivated virus (NIV) solution or in drug product (DP) suspension following further dilution of NIV and formulation with Aluminium hydroxide. In another set of experiments, different Alum lots covering a broad content range of residual metal ions were used and formulated with a single defined NIV lot. All of these formulations still contained residual formaldehyde and bisulphite at representative concentrations compared to commercial product. Stock solution of metal salts were dissolved in water and spiked to the samples to the desired final concentration.

2 Definitions & Abbreviations

AcCN Acetonitrile
ANOVA Analysis of variance
DOE Design of experiments
DP Drug product
DS Drug substance
FBV Final bulk vaccine
FVL Final Vaccine lot
GI Gamma irradiated
HPLCHigh performance liquid chromatography
LSD Fisher's least significant difference
mAb Monoclonal antibody
NIV Neutralized inactivated virus
PS Protamine sulphate
RP Reversed Phase
SEC Size exclusion chromatography
SN Supernatant
TFA Trifluoroacetic acid
w/o without 3 Materials and Methods 3.1 Materials

- Iron(II)chloride tetrahydrate (Sigma, Order no. 44939)
- Iron(III)chloride hexahydrate (Sigma, Order no. 31232)
- Nickle(II)sulphate hexahydrate (Sigma, Order no. N4882)
- Cobalt(II)chloride hexahydrate (Sigma, Order no. 31277)
- Copper(II)chloride dehydrate (Sigma, Order no. 807483)
- Zinksulphate heptahydrate (Sigma, Order no. 24750)
- Crom(III)chloride hexahydrate (AlfaAesar, Order no. 42114)
- Ethylenediaminetetraacetic acid disodium salt dehydrate (EDTA) (Sigma, E5134)
- Aqua bidest. (Fresenius Kabi, Art no. 0712221/01 A)
- 10×PBS (Gibco, Order No. 14200-091)
- Formaldehyde solution 37% (Merck, Cat No. 1.040031000)
- Protamine sulphate (Intercell Biomedical Ltd, Batch no. 086056)
- LoBind Eppis 2 ml (Eppendorf, Cat. No. 0030 108.132)
- 15 ml Falcon tubes (Greiner, Cat. No. 188724)
- Incubator Infors HT Incubator Multitron Standard (InforsAG)
- 0.2 μm filter Mini Kleenpak 25 mm (Pall)
- NIV11A74 and Final bulk vaccine (FBV, formulated with Alum lot 4539) JEV 11D87 from commercial production runs was obtained from Intercell Biomedical (Livingston, UK) and stored at 2-8° C. until further processing
- Stock solutions of metal salts in water (final concentration 1 mM) used for spiking experiments were prepared and stored at 2-8° C. until usage
- Aluminium hydroxide samples (2% Al2O3, Brenntag Biosector) were either retain samples obtained from Intercell Biomedical or purchased directly from Brenntag. Alum samples were stored at 2-8° C. The following Alum lots were used in this study: 4470, 4563, 4621, 3877, 4230 (non-gamma irradiated and gamma irradiated)

3.2 Preparation of Metal Stock Solutions 3.2.1 Iron(II) Stock Solution 20 mM Iron(II) stock solution was prepared by dissolving 397 mg of Iron(II)chloride tetrahydrate in 100 mL aqua bidest.

3.2.2 Iron(III) Stock Solution 20 mM Iron(III) stock solution was prepared by dissolving 540 mg of Iron(III)chloride hexahydrate in 100 mL of aqua bidest.

3.2.3 Nickle(II) Stock Solution 20 mM Nickle(II) stock solution was prepared by dissolving 525 mg of Nickle(II)sulphate hexahydrate in 100 mL of aqua bidest.

3.2.4 Cobalt(II) Stock Solution 20 mM Cobalt(II) stock solution was prepared by dissolving 476 mg of Cobalt(II)chloride hexahydrate in 100 mL of aqua bidest.

3.2.5 Copper(II) Stock Solution 20 mM Copper(II) stock solution was prepared by dissolving 341 mg of Copper(II)chloride dihydrate in 100 mL of aqua bidest.

3.2.6 Zink Stock Solution 20 mM Zink stock solution was prepared by dissolving 575 mg of Zinksulphate heptahydrate in 100 mL of aqua bidest.

3.2.7 Crom(III) Stock Solution 20 mM Crom(III) stock solution was prepared by dissolving 533 mg of Crom(III)chloride hexahydrate in 100 mL of aqua bidest.

3.3 Preparation of Working Solutions

Working solutions of metal ions (1 mM final concentration if not otherwise stated) were prepared by dilution of metal ion stock solutions with aqua bidest and sterile filtration via 0.2 μm syringe filter.

3.4 Preparation of Formulation

All formulations were prepared under sterile conditions. NIV and FBV obtained from commercial production runs were adjusted to the desired pH and spiked with aliquots of metal stock solution. All samples were stored in plastic tubes if not otherwise stated. In all formulations using Alum, the final Al content was 500 μg/mL, corresponding to 0.1% Al2O3. It has to be noted that metal ions, especially iron (II), iron (III) and to a certain extent Cr (III), formed a precipitate with the phosphate ions present in the buffer resulting in partial co-precipitation of the inactivated virus represented by the low recovery determined by size-exclusion HPLC (SEC-HPLC).

3.4.1 Experiment 20110913(NIV): NIV Formulation at Different Metal Ion Concentration of Ni(II), Cu(II), Cr(III) with or w/o Presence of PS Fragments NIV 11A74 was adjusted to pH 7 and pH 8 followed by spiking of metal ions (Ni(II), Cr(III)) at 100/500/1000 ng/mL final concentration. All formulations were stored in low-bind Eppendorf tubes at 22° C. Aliquots of all formulation were also prepared in presence of protamine sulphate fragments (50 μg/mL). This was done to evaluate for any effect of PS fragments on JEV stability in presence of metals. The preparation of Protamine Sulphate (PS) fragments is described in Example 1. Samples were prepared on the same day (see Table 9) and analyzed three weeks later. All samples were analyzed by SEC-HPLC, but only samples at pH 8 (#21-40) were analyzed by ELISA.

3.4.2 Experiment 20110913(DP): DP Formulation at Different Metal Ion Concentration of Ni(II), Cu(II), Cr(III)

FBV 11D87 (formulated with Alum Lot 4539) was used in this study. FBV was adjusted to pH 7 and pH 8 and spiked with Ni(II)/Cu(II)/Cr(III) at 100, 500 and 1000 ng/mL to evaluate any metal ion concentration/pH depended effect. Table 10 shows the experimental design of this experiment. All formulations were stored in Falcon tubes at 2-8° C. and 22° C. Samples stored at 22° C. were analyzed by SEC-HPLC and ELISA after 5 weeks.

3.4.3 Experiment 20110812-Metal Spiked DP

Final Bulk Vaccine 11D87 (formulated with Alum Lot 4539) was obtained from a commercial production run and used in this study. Residual formalin in DS was analyzed as 28.1 ppm, residual sulphites was 92.2 ppm. Actual content in DP can be considered to be in the same range. FBVJEV11D87 was adjusted to pH 7.0/7.4/7.8 and spiked with 500 ng/mL (final concentration) of Fe(II), Fe(III), Ni(II), Co(II), Cu(II), Zn(II). A metal ion mix formulation was also prepared containing all of the individual metal ions together in solution. Formulations with Cr(III) were prepared later on and Cr(III) was not included in metal ion mix. Control formulations were only adjusted to the desired pH, but not spiked with metals. All formulations (#1-24) were prepared on the same day and stored in Falcon tubes at 2-8° C. and 22° C.

Additional Cr(III) spiked samples (#25-27) were prepared by taking aliquots of the control samples stored at 2-8° C. and spiked with Cr(III) to a final concentration of 500 ng/mL. Formulations were stored at accelerated conditions (22° C.) only. Table 11 shows the experimental set-up of this experiment. All samples stored at 22° C. were analyzed by ELISA (monoclonal and polyclonal) after 4 weeks and 7 weeks.

3.4.4 Experiment 20110819: DP Formulation Using Various Alum Lots

Spiking studies as described above can give first evidence of possible instability of the formulated antigen in presence of certain metals, but might not be completely representative of the real conditions where metals present in Aluminium hydroxide are incorporated in the three-dimensional structure of the gel resulting in different local concentration and orientation/accessibility. To overcome these limitations an initial study was started to simulate the real conditions. A single NIV batch (11A74) obtained from a commercial production run was formulated with various Alum lots produced by Brenntag covering a broad range of residual metals. 4.75 mL of NIV was mixed with 0.25 mL Alum (2%) in Falcon tubes. The final Aluminium hydroxide concentration was 500 μg/mL (=0.1% Al2O3). Formulated vaccine samples were stored at 2-8° C. and under accelerated conditions at 22° C. All of these Alum lots contained residual metal ions at different concentrations. Alum lot 4230 has the highest level for Fe, Cu, Ni and V (see Example 3). Note that metal ion valences cannot be specified by ICP-MS. A mixed Alum sample containing equal amounts of 4230 and 4074 was also prepared to get an "intermediate" level for Ni(II) and Cu(II). Samples were analyzed after 6 weeks of storage at 22° C. The residual amount of formaldehyde and sulphite estimated by recalculation from available DS analysis results corrected by dilution factor of NIV to DS was 76 ppm formaldehyde and 192 ppm sulphite respectively.

3.1 Antigen Desorption from Aluminium Hydroxide for SEC-MALLS Analysis

Viral particles were desorbed from Aluminium hydroxide. ~625 μL of DP was spun down (8° C., 5 min, 3300×g) and the supernatant was either discarded if not otherwise stated or analyzed by JEV-SEC-MALLS to detect the unbound antigen concentration. Viral particles were desorbed by suspending the Aluminium hydroxide particles with 62.5 μL 0.8 M potassium phosphate buffer (pH 8) containing BSA (50 μg/mL). BSA was added to the desorption buffer for SEC-MALLS analysis to minimize losses caused by unspecific adsorption of the antigen. After shaking (500 rpm) the Aluminium hydroxide particles for 10 min at room temperature, particles were removed by centrifugation and the supernatant was collected into a LoBind Eppendorf tube and the desorption procedure repeated on remaining sample. The pooled desorbed antigen (~5× concentrated sample; final volume 125 μL; starting volume ~625 μL) was then further analyzed by SEC-MALLS.

3.2 SEC-MALLS HPLC Method

Desorbed antigen was analyzed by SEC-MALLS. In brief, following desorption of the antigen from Aluminium hydroxide 100 μL of the pooled desorbed material (~5× concentrated) were subsequently loaded onto a Superose 6 10/300 GL SEC column. 1×PBS+250 mM NaCl was used as mobile phase. Ultraviolet (UV) 214 nm and MALLS signals of viral particles were recorded and analysed using Chromeleon and ASTRA software packages.

3.3 Inactivated JEV ELISA (Polyclonal Based)

Desorption of the antigen from Alum and ELISA analysis was carried out using polyclonal sheep anti JEV antibodies for coating the 96 well ELISA plates as described in Example 4.

3.4 Inactivated JEV ELISA (Monoclonal Based)

During course of this investigational testing, a monoclonal (mAb) based JEV ELISA was developed. The assay is primarily based on the "polyclonal JEV ELISA" assay format, only a monoclonal anti-JEV antibody (clone 52-2-5) is used for coating and the current polyclonal antibody for detection. The employed mab 52-2-5 was shown to be specific for JEV and to recognize a neutralizing epitope. Mab clone 52-2-5 was obtained by subcutaneously immunizing BALB/c mice with commercially available vaccine lot JEV08J14B. Spleen cells of the mice were fused to myeloma cells. From resulting hybridoma cells single clones were selected and sub-cloned. The clones were negatively screened against Bovine Serum Albumin, Protamine sulphate and an extract of the production cell line of the JE-vaccine (Vero cells). A positive screen was done against Neutralized Inactivated Virus (NIV) of vaccine lot JEV08M20. For screening, microtiter plates were coated with the relevant antigen and reacted with supernatant of cultures of the selected clones. For detection a goat anti mouse polyclonal antibody conjugated with alkaline phosphatase was used. Mab clone 52-2-5 was shown to recognize a neutralizing epitope on domain III of the envelope (E) protein of JEV containing Ser331 and Asp332 (Lin C.-W. and Wu W.-C. J Virol. 2003; 77(4):2600-G). Binding of the mab to the indicated neutralizing epitope is for instance determined as described in Lin and Wu (2003) by site-directed mutagenesis of the domain III at position 331 (for instance: S→R), and/or by alanine mutations at or near position 331 of domain III, for instance of residues Ser 331 and Asp332, followed by immunoblots to determine binding of the mab to the mutated proteins. Negative binding results indicate that the epitope of the mab is the neutralizing epitope identified by Lin and Wu (2003). The neutralizing characteristic of the epitope gives rise to the assumption that the epitope might be of importance for the antigen to elicit a protective immune response.

JEV samples were analyzed by both ELISA assays, polyclonal and monoclonal. The relative specific epitope content can be expressed as the ratio of the total antigen content determined by "monoclonal ELISA" (clone 52-2-5) divided by total antigen content determined by "polyclonal ELISA". Any differences in the ratio may indicate differences in specific epitope content 52-2-5. Results close to 1 would correspond to high epitope contents, and results close to 0 correspond to low relative epitope content. A low ratio indicates presence of structural changes of the neutralizing epitope.

In the course of development of this "mAb ELISA", differences between vaccines lots were detected, which could be correlated with potency results of these lots.

3.5 Statistical Evaluation

Statistical evaluation was done with Statgraphic Plus 3.0.

4 Results 4.1 Experiment 20110913(NIV): NW Formulation at Different Metal Ion Concentration of Ni(II), Cu(II), Cr(III) with or w/o Presence of PS Fragments SEC-HPLC results of NIV formulations (pH 7 and pH 8) containing metal ions [Ni(II), Cu(II), Cr(III)] w/ and w/o PS fragments are summarized in Table 12. SEC-HPLC results show that antigen recoveries of most of the samples was >80%. Some samples (#7, #36, #38) showed slightly reduced recoveries in the range of 70-80%. It has to be noted that the actual virus content is quite low and precision of HPLC results can be estimated as approx. ±20%. Since for samples #36 and #38 the recoveries for following formulations (#37, #39) at next level of individual metal ion content were higher again, these differences might be caused by assay variability and were not considered as significant. Based on the results obtained it was not possible to clarify the influence of metal ions with respect to the recovery of soluble inactivated JEV. However, SEC-HPLC only gives information about content of soluble virus, but no information about any potential surface modification. Only formulations prepared at pH 8 were also analyzed by ELISA (duplicate analysis). The ratio of monoclonal/polyclonal ELISA was calculated and can be used for comparison purpose of results. Analysis of samples by ELISA (see Table 13) do not show any significant influence of tested metals on degradation of inactivated JEV at pH 8 after three weeks at 22° C. There might be a trend of decreasing ratio in presence of Cu(II), but overall it appears that an incubation time of three weeks at 22° C. seems not be sufficient to detect any significant degradation. As also shown in DOE experiment (Example 1) inactivated JEV appears to have higher stability at pH 8 when stored at accelerated conditions at 22° C. and this would also contribute that significant effects were not observed. In this experiment it was also shown that PS fragments do not have any influence on JEV stability. This is also well in agreement with DOE results. NIV samples 1-20 formulated at pH 7 showed significant reduction in monoclonal epitope content in presence of Cu(II). At the highest tested concentration (1000 ng/mL) the ratio was close to zero indication significant structural changes of the antigen.

4.2 Experiment 20110913(DP): DP Formulation with Different Metal Ion Concentration of Ni(II), Cu(II), Cr(III)

Figure 8:
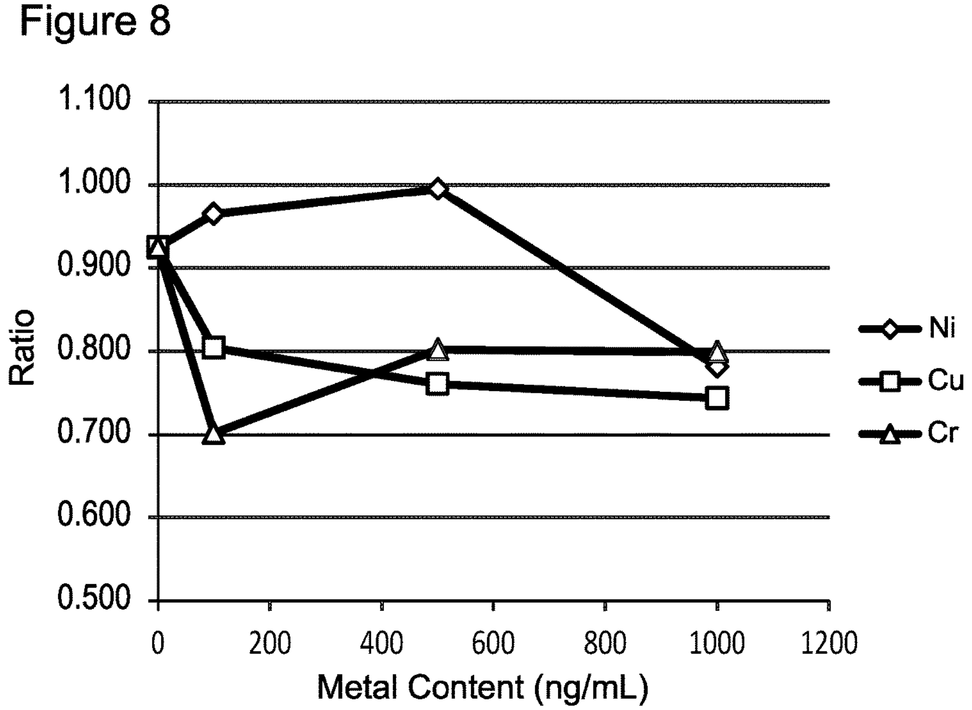
FIG. 8: ELISA ratio (monoclonal/polyclonal) for JEV formulations at pH 7 in presence of Ni, Cu and Cr. Samples were stored at 22° C. for 5 weeks.

Analysis of desorbed JEV antigen is summarized in Table 14 (SEC-HPLC) and Table 15 (ELISA). Antigen recoveries for all samples as determined by SEC-HPLC was >80% after 5 weeks at 22° C. indicating no significant influence of tested metal ions on desorption recovery. As shown in FIG. 8, there is a trend of decreasing ratio as analyzed by ELISA in presence of Cu(II) and Cr(III) at pH 7. Formulations at pH 8 appear to be more stable.

4.3 Experiment 20110812(DP): Metal Ion Spiked DP

Figure 9:
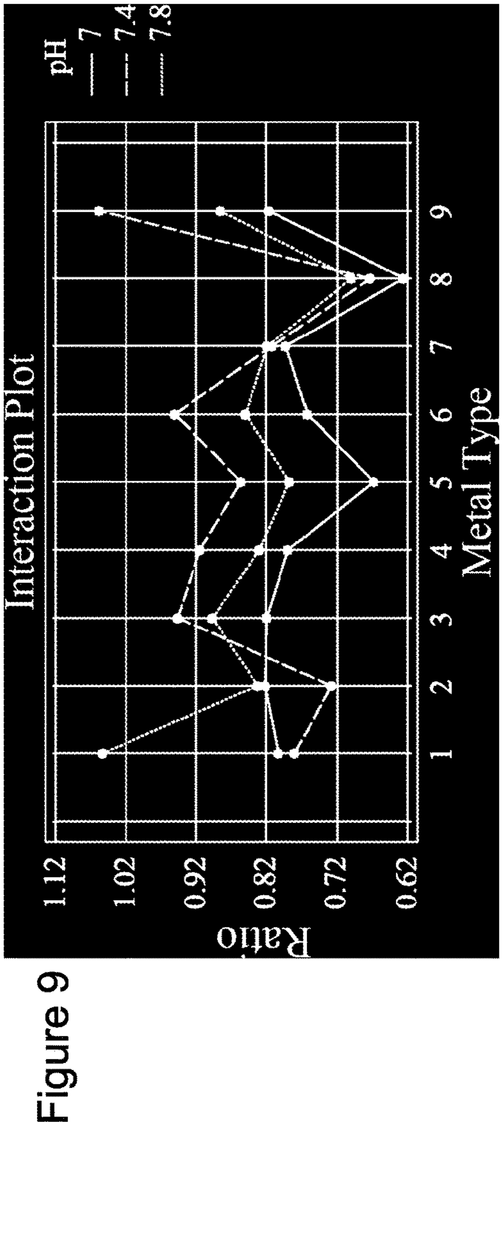
FIG. 9: Summary of results obtained after 7 weeks at 22° C. Shown are the raw data of ratio as a function of pH and metal ion type and combined results for each parameter.
Figure 9:
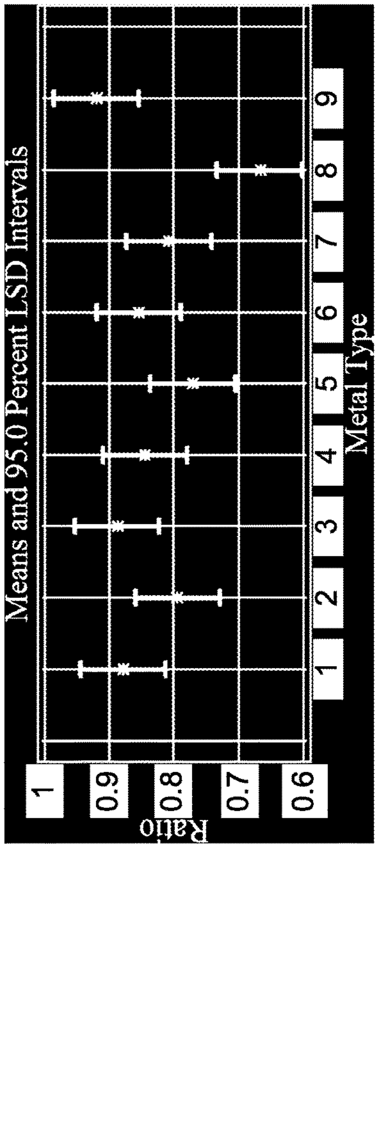
Figure 9:
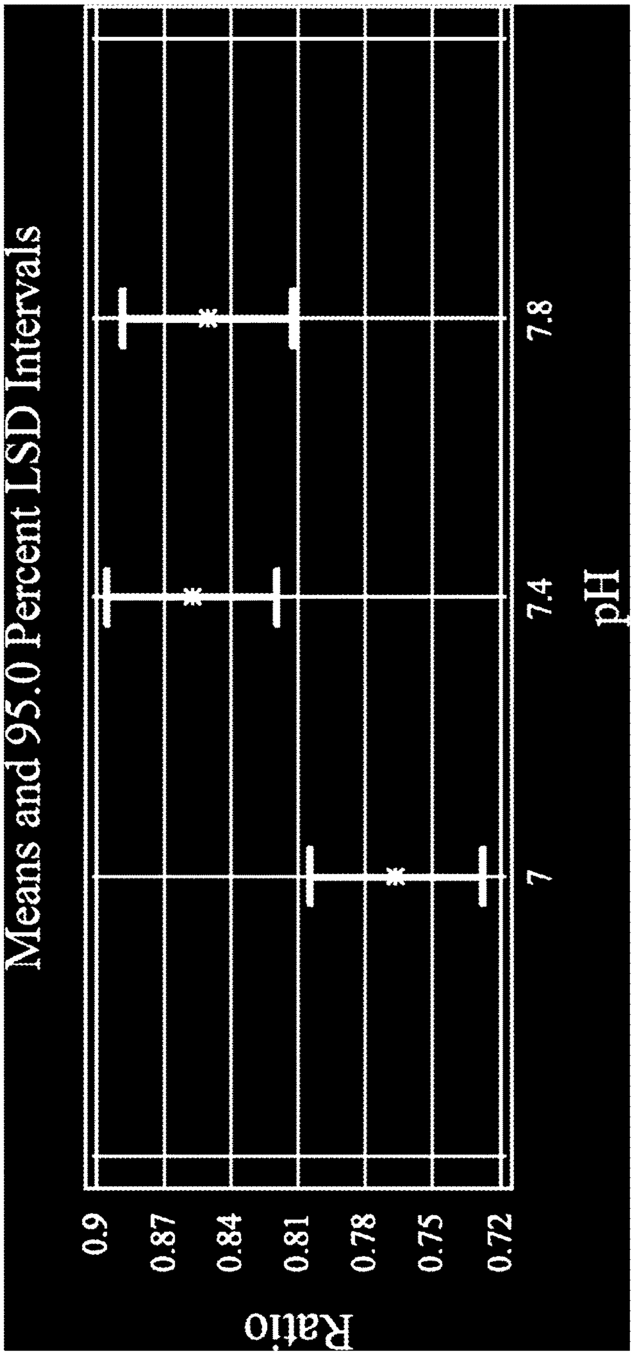

In this experiment FBV11D87 was used as starting material. The formulation pH value was adjusted in a more narrow range (pH 7.0, 7.4, 7.8) and additional metal ions were used for spiking, each at 500 ng/mL (final concentration). The metal ion mix contained all individual metal ions with the exception of Cr(III) in single formulations (each metal at 500 ng/mL). ELISA results obtained after 4 weeks and 7 weeks at 22° C. are summarized in Table 16. Results are also displayed as graphs in FIG. 9.

Statistical evaluation of stability samples stored at 22° C. for 7 weeks was performed. ANOVA (analysis of variance) showed significant effects of parameters (pH and metal type) on antigen stability, that is expressed as the ratio of monoclonal/polyclonal ELISA (see Table 17). The ANOVA table decomposes the variability of Ratio into contributions due to various factors. Since Type III sums of squares have been chosen, the contribution of each factor is measured having removed the effects of all other factors. The P-values test the statistical significance of each of the factors. Since the P-values for pH and metal ion type are less than 0.05, these factors have a statistically significant effect on Ratio at the 95.0% confidence level.

In Table 18 a multiple comparison procedure is applied to determine the significance of the differences observed with respect to the means. Significant effect on ratio was shown for Cu(II) and the metal mix compared to the non-spiked control formulations. The bottom half of the output shows the estimated difference between each pair of means. An asterisk has been placed next to 7 pairs, indicating that these pairs show statistically significant differences at the 95.0% confidence level. At the top of the page, 3 homogenous groups are identified using columns of X's. Within each column, the levels containing X's form a group of means within which there are no statistically significant differences. The method currently being used to discriminate among the means is Fisher's least significant difference (LSD) procedure. With this method, there is a 5.0% risk of calling each pair of means significantly different when the actual difference equals 0.

Significant effect on ratio was shown for Cu(II) and the metal ion mix. The influence of other metal ions might become significant at longer storage period. The metal ion mix contained the highest total concentration and might represent a worst case. However, it was concluded that several metal ions present in Alum might contribute to degradation, each to different extent. These results further support the proposed root cause of metal ion-catalysed antigen degradation. It has to be noted that spiking experiment might not fully simulate the real conditions of residual metal ion impurities present in Alum 4230. Metal ions are incorporated in the Alum structure and the local concentration and orientation might be different from metal ions used in spiking experiments. It is also known that metal ions (e.g. Fe) have low solubility in presence of phosphate ion ($PO43^-$). Therefore the actual concentration of soluble metal ions and contribution of metals present as metal-phosphate complex on JEV degradation is unknown.

4.4 Experiment 20110819: Preparation of DP Samples with Different Alum Lots

Spiking studies as described earlier can give first evidence of possible instability of the formulated antigen in the presence of some metal ions, but might not be completely representative of the real conditions where these metal ions present in Aluminium hydroxide are expected to be incorporated in the three-dimensional structure of the Aluminium-hydroxide gel resulting in different local concentration and orientation/accessibility. To overcome these limitations an initial study was started to simulate the real conditions. A single NIV (11A74) was formulated with various Alum lots obtained by Brenntag covering a broad range of residual metals. Formulated vaccine samples were stored at 2-8° C. and under accelerated conditions at 22° C. All of these Alum lots contained residual metal ions at different levels. Lot 4230 had the highest level for Fe, Cu, Ni and V (see Table 19). Note that the actual content of metal ions present in the formulated product is only 1/20 of the concentration in Alum (2%) stock solution. Note that metal ion valences cannot be specified by ICP-MS. Analysis of desorbed antigen by ELISA of samples stored at 22° C. for 6 weeks is shown in Table 20.

Figure 10:
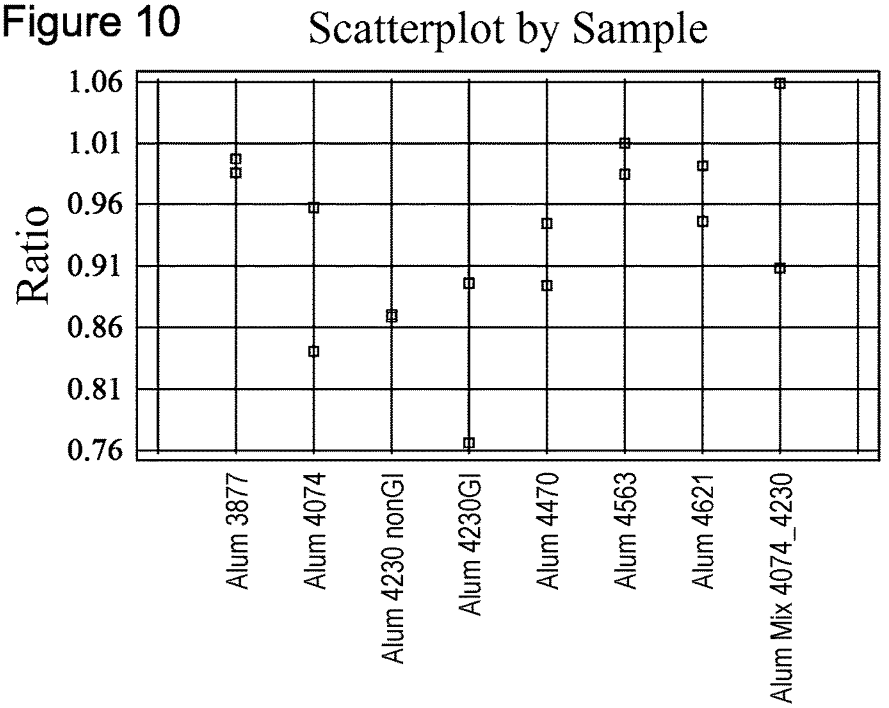
FIG. 10: Mean ratio of DP formulations prepared with different Alum lots. Samples were stored for 6 weeks at 22° C. Error bars represent the 95% confidence interval calculated based on pooled standard deviation. Samples from left to right: Alum 3877, Alum 4074, Alum 4230 nonGI, Alum 4230 GI, Alum 4470, Alum 4563, Alum 4621, Alum Mix 4074_4230.
Figure 10:
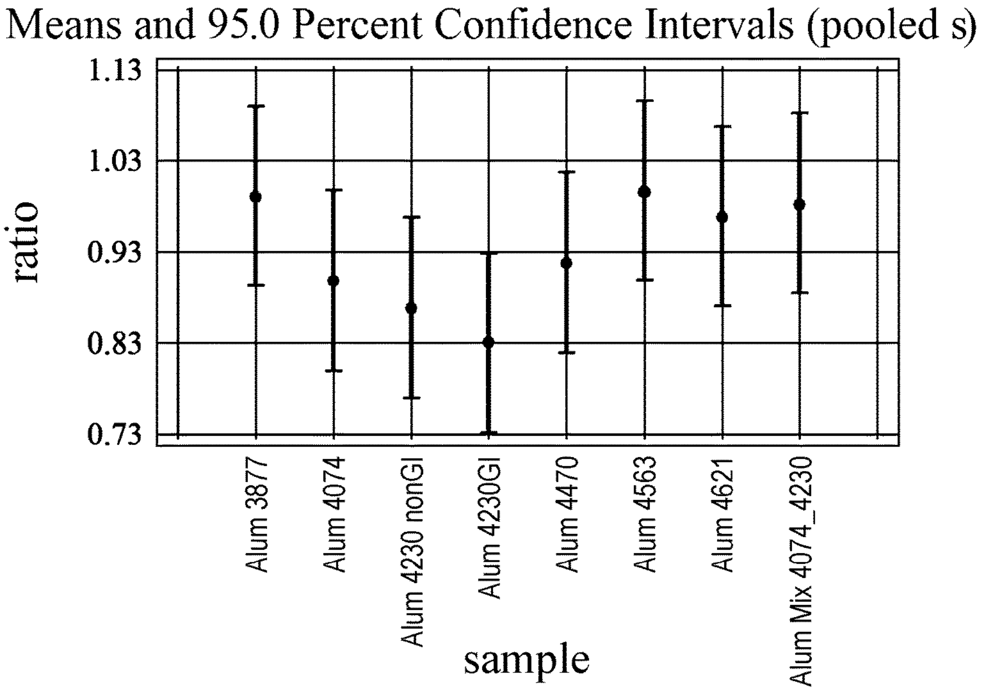

Pooled standard deviation was calculated from all samples (spooled ~0.075) as a measurement of experimental uncertainty. Mean values for ratio and 95% confidence intervals (calculated based on spooled) were plotted against the individual formulations (see FIG. 10). Samples formulated with Alum 4230 showed a trend to lower ratio compared to the other samples. However, differences were not as large to show statistical significant differences between the various formulations.

5 Summary

It was shown that metal ions contribute to the degradation of the inactivated JEV under accelerated storage conditions (22°). In spiking studies higher concentration of residual metal ions (range 100-1000 ng/mL) were used than present in FVL formulated with Alum lot 4230 (e.g. Fe~310 ng/mL; Cr~64 ng/mL; Ni~52 ng/mL). Cu content in FVL can be only estimated as 3 ng/mL based on ICP-MS data of 2% Alum stock solution since LOD is 25 ng/mL. Higher metal concentration and storage temperature were chosen to increase the rate of any potential degradation reaction. In fact, for FVL JEV09L37, the potency loss occurred after 11 month stored at 2-8° C. It was also shown that metals can form insoluble complexes with phosphate ions making estimation of actual levels of metals present difficult.

In spiking experiments ELISA results showed statistically significant structural changes of virus surface in as little as 4 weeks at 22° C. in presence of metal ions. It was shown that the ELISA ratios for formulations containing Cu(II) and metal ion mix (containing Fe(II), Fe(III), Co(II), Cu(II) and Zn(II)) were statistically significant lower compared to the non-spiked control formulation. Cu(II) was also found in Alum lot 4230 (2% stock solution) at 64 ng/mL, corresponding to ~3 ng/mL in FVL. In all other Alum (2%) lots Cu(II) content was <25 ng/mL (below limit of detection).

For formulation experiments of the antigen using different Alum lots, longer storage time (>6 weeks at 22° C.) at accelerated conditions is required. There is a trend that formulations prepared with Alum 4230 showed lower ELISA ratios compared to other lots. Slower degradation rate compared to spiked formulation might be contributing to lower metal ion content in commercial Alum lots. It was also observed that the antigen shows higher stability at pH 7.5-8 compared to pH 7 and that PS fragments do not contribute to any degradation reaction. These results are in good agreement with DOE results described in Example 1.

Example 3

As part of the out-of-specification investigation concerning FVL JEV09L37, the used Aluminum hydroxide lot (lot 4230) was determined to be the most probable root cause for the observed loss of potency. Aluminum hydroxide (referred to as Alum during the manufacturing process of JE-PIV) is purchased from Brenntag Biosector as autoclaved suspension termed "ALHYDROGEL® Aluminium Hydroxide Gel Adjuvant". Each batch is sterilized by radiation prior to use in the JEV production process.

A number of different ALHYDROGEL® batches were analyzed for appearance, metal ion content and physical properties.

1 Introduction 1.1 Aluminum Hydroxide

Brenntag Biosector's ALHYDROGEL® has a specified Aluminum content of 10 mg/mL which translates to 2% $Al_2O_3$ and 3% $Al(OH)_3$, respectively. Further specifications are Nitrogen (max 0.005%), free Sulphate (max 0.05%), total Sulphate (max 0.1%) and pH (6.5±0.5). it has a shelf life of 26 months when stored at room temperature.

1.2 Generation of Aluminum Hydroxide

ALHYDROGEL® 2% (referred to as Aluminum hydroxide) is manufactured by Brenntag (CAS no. 21645-51-2).

1.3 Use of Aluminum Hydroxide Lots in JEV Manufacturing

For the production of commercial JEV vaccine batches a total of 5 different Brenntag ALHYDROGEL® 2% lots have been used so far.

2 Definitions & Abbreviations

ALHYDROGEL® 2% Aluminum hydroxide solution (also referred to as alum)

DS/DP Drug Substance/Drug Product

ESG Environmental Scientifics Group

F-AAS Flame Atomic Absorption Spectrometry

FVL Final Vaccine Lot

GF-AAS Graphite Furnace Atomic Absorption Spectrometry

ICP-MS Inductively-Coupled-Plasma Mass Spectrometry

JEV Japan Encephalitis Virus

JE-PIV Japan Encephalitis Purified Inactivated Virus

LOQ Limit Of Quantification

P&TDPatch & Technical Development

PSD Particle Size Distribution

PZC Point of Zero Charge

QCI Quality Control Immunology

3 Materials and Methods 3.1 ALHYDROGEL® Batches

ALHYDROGEL® 2% lots: 3877, 4074, 4187, 4230, 4414, 4470, 4539, 4563, 4587, 4621 (not all Alum lots listed were used in the formulation of JE-PIV) ALHYDROGEL® 2% 7× washed lots: 4577, 4580, 4596 (sourced from Brenntag, not typical of the 2% Alum received for formulation).

3.2 ALHYDROGEL® PSD Measurements

Aluminum hydroxide particle size distribution (PSD) was analyzed on a Malvern Mastersizer 2000 μPsystem with a 20 mL sample cell.

ALHYDROGEL® 2% bulk substance was diluted 1:20 in water and 1 mL was added to the sample cell. Final dilution of sample in sample cell was therefore 400 fold (0.005% Aluminum hydroxide).

3.3 ALHYDROGEL® Zeta-Potential Measurements

Zetapotential and point of zero charge (PZC) was measured on a Malvern Zetasizer ZS system equipped with a MPT-2 autotitrator. ALHYDROGEL® 2% bulk substance was diluted 1:20 in PBS and equilibrated over night at room temperature. For recording of the charge titration curve the pH was adjusted using 100 mM HCl and 100 mM NaOH solutions. PZC was determined by extrapolation of the zero charge in the titration plot (intersection of titration curve and x-axis). Point of zero charge corresponds to the pH value where the surface of the sample has no net charge.

3.4 Analysis of Metal Ions in Aluminum Hydroxide

Selected metal ions were analyzed either by inductively-coupled-plasma mass spectrometry (ICP-MS), flame atomic absorption spectrometry (F-AAS) and graphite furnace atomic absorption spectrometry (GF-AAS) at the Medical Laboratory Bremen (Germany). In short, samples containing Aluminum hydroxide were treated with conc. $HNO_3$ under heat until a clear solution is obtained. The clear solution is then further diluted and analyzed. The presence and content of following metal ions were determined: Pb, Cd, Cr, Co, Fe, Cu, Ni, Ag, W and Al. Depending on the sample dilution, the limit of quantification (LOQ) was 5 to 25 ng/mL.

In addition a semi-quantitative 70-Element scan was performed by ESG (UK) using a combination of ICP-MS (Agilent 7500ce) and ICP-AES (Perkin Elmer Optima 4300DV), which were calibrated using certified standards. The element scan is a screening method and not as sensitive as trace metal analysis for selected metals as performed by Medical Laboratory Bremen. However, such a screening gives a good overview about the presence and levels of certain metals.

4 Results 4.1 Determination of ALHYDROGEL® Particle Size Distribution

Figure 11:
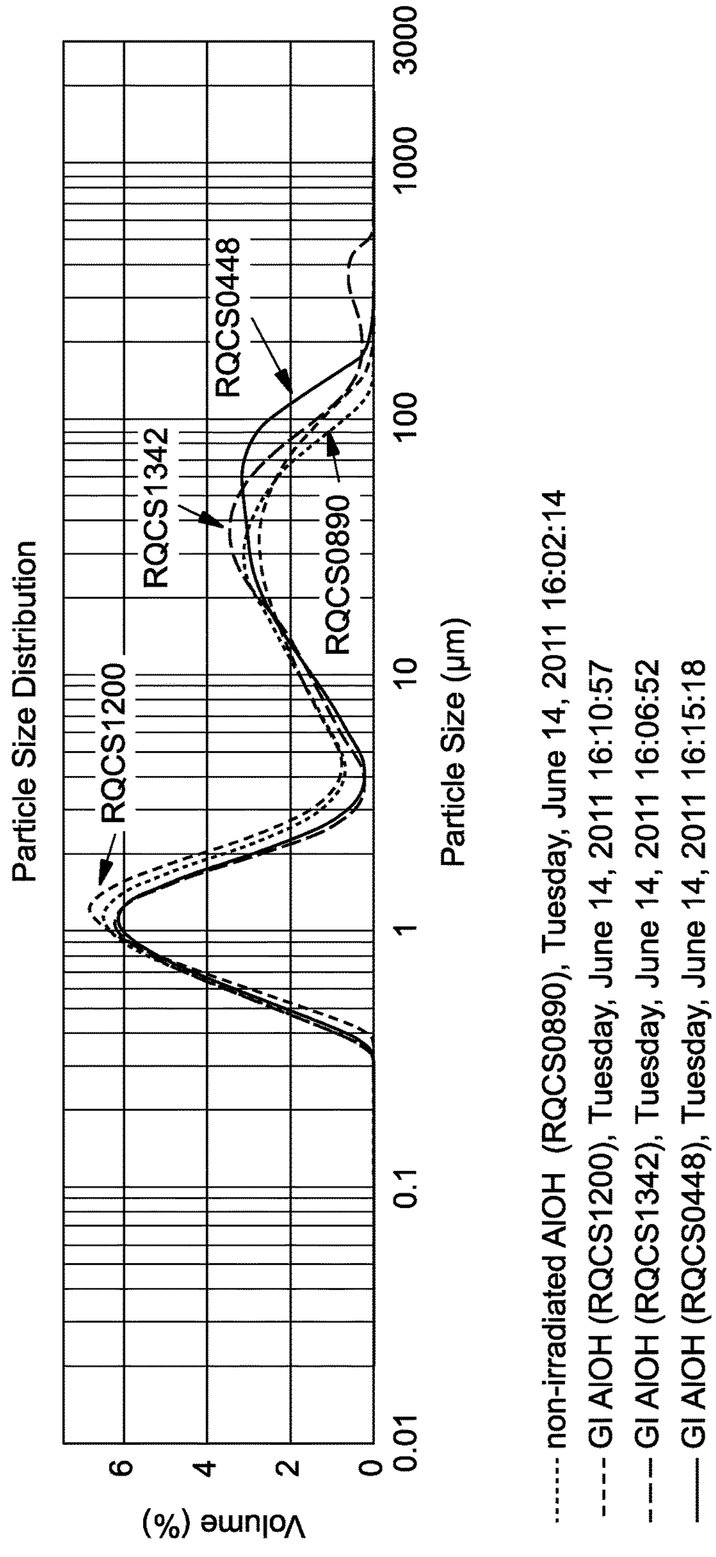
FIG. 11: Particle size distribution of ALHYDROGEL® samples.

Table 21 summarizes PSD data of two sublots each of ALHYDROGEL® lots 4230 and 4740. Distribution results are shown in FIG. 11. Mean particle was ~2-4 μm with populations of smaller (<1 μm) and larger (>20 μm) particles being present in all four samples. The four tested ALHYDROGEL® samples showed no significant difference in mean particle size distribution.

4.2 Zeta-Potential Measurements

Figure 12:
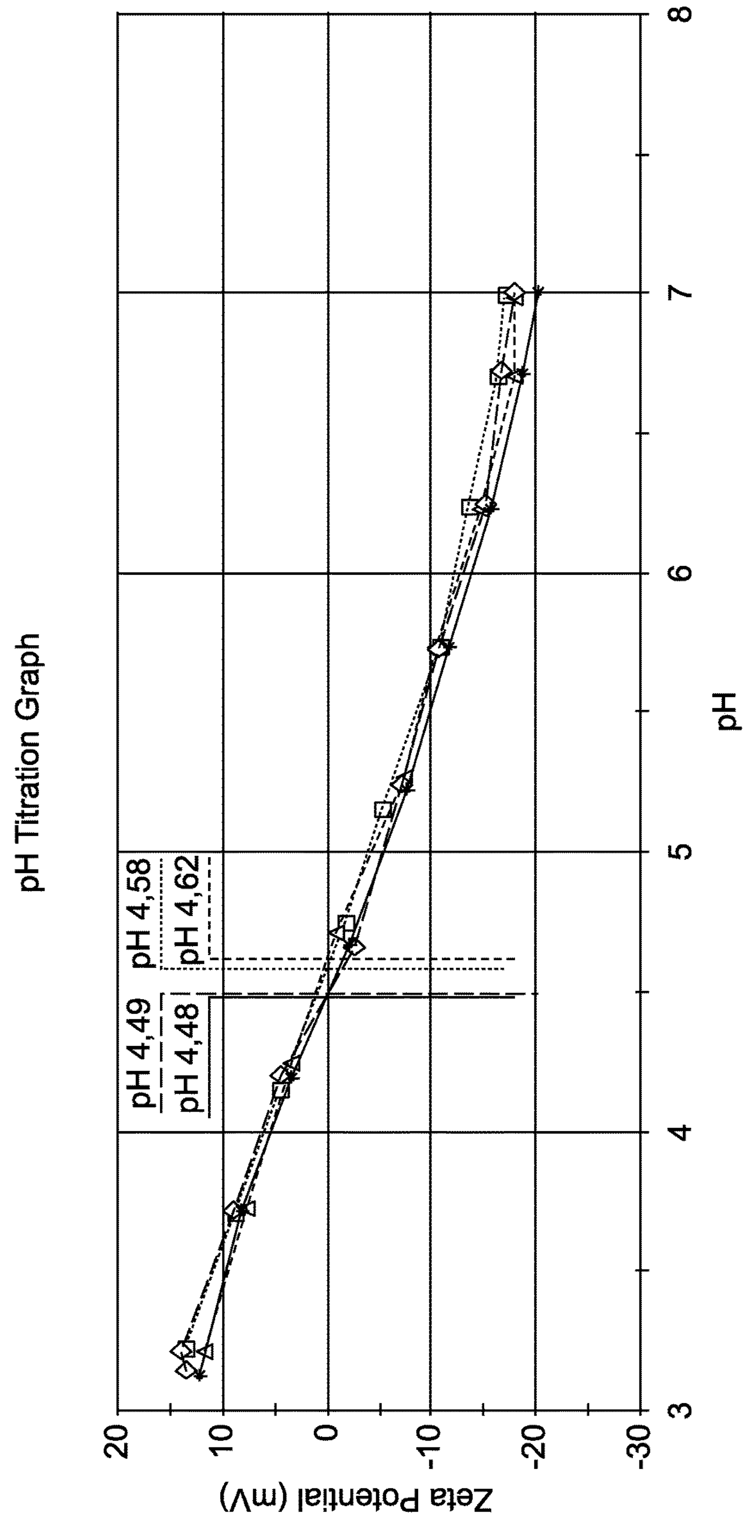
FIG. 12: ALHYDROGEL® titration curves in PBS. ■ non-irradiated AlOH (RQCS0890), ▲ GI AlOH (RQCS1200), ♦ GI AlOH (RQCS1342), + GI AlOH (RQCSO448).

Two sublots each of ALHYDROGEL® lots 4230 and 4740 (2% stock solution diluted 20 fold in PBS and equilibrated overnight at RT before analysis) were analyzed for point of zero charge. Table 22 summarizes results of PZC for the four samples showing very similar PZC in PBS buffer. Titration curves are shown in FIG. 12. No difference in the titration curves and PZC could be observed between the four analyzed samples.

4.3 Determination of Residual Metal Ion Content in ALHYDROGEL® Batches

The current limits for Fe in 2% Aluminum hydroxide solutions according to the Ph. Eur. are 15 ppm (=15 μg/mL) and a total maximum of 20 ppm (=20 μg/mL) for other heavy metals (such as Pb). However, a concentration of 15 ppm Fe would correspond to 0.27 mM Fe in solution. Taking into consideration that even trace amounts of residual metal ions can catalyze a variety of degradation reactions for proteins (e.g. oxidation, activation of proteases etc.) and that metals remain stable in solution, differences in metal ion content between Aluminum hydroxide lots might cause differences in antigen stability over time.

The concentrations of a number of metal ions in commercially available aluminum hydroxide lots were analyzed using ICP-MS. The results of these analyses are summarized in Table 23. Lots 4074, 4230, 4470, 4414 and 4539 were used in the production of commercial JEV batches. As a 2% ALHYDROGEL® stock solution equals an Al concentration of 10 mg/mL the quantification of Al content in the different samples can be used as reference for the results obtained for the other metal ions. Indeed an average Aluminum content of 10.3 mg/mL could be measured showing the accuracy and reproducibility of the method.

When comparing the different ALHYDROGEL® lots large variations in the amount of contaminating metal ions could be observed. Most notable contaminating metal ions are Fe, Cr and Ni which were detected in all batches. In addition lot 4230 contained detectable amounts of Cu which was below LOQ in all other batches.

However, it has to be noted that none of these metals were detected in quantities near the specifications of ALHYDROGEL® mentioned above. For example the highest concentration of iron found in lot 4230 was 5.6 μg/mL or roughly 40% of the permitted concentration.

An "improved" ALHYDROGEL® is washed 7 times with water during the purification step instead of only 4 times for standard ALHYDROGEL®. To test if this additional washing steps would result in reduced metal ion contamination three different lots (4580, 4596 and 4577) were analyzed. Results are included in Table 23. No difference in metal ions comparing to the standard grade ALHYDROGEL® could be observed suggesting that the metal ions are either strongly bound to the surface of the Aluminum hydroxide particles or actually co-precipitate during the production process.

Figure 13:
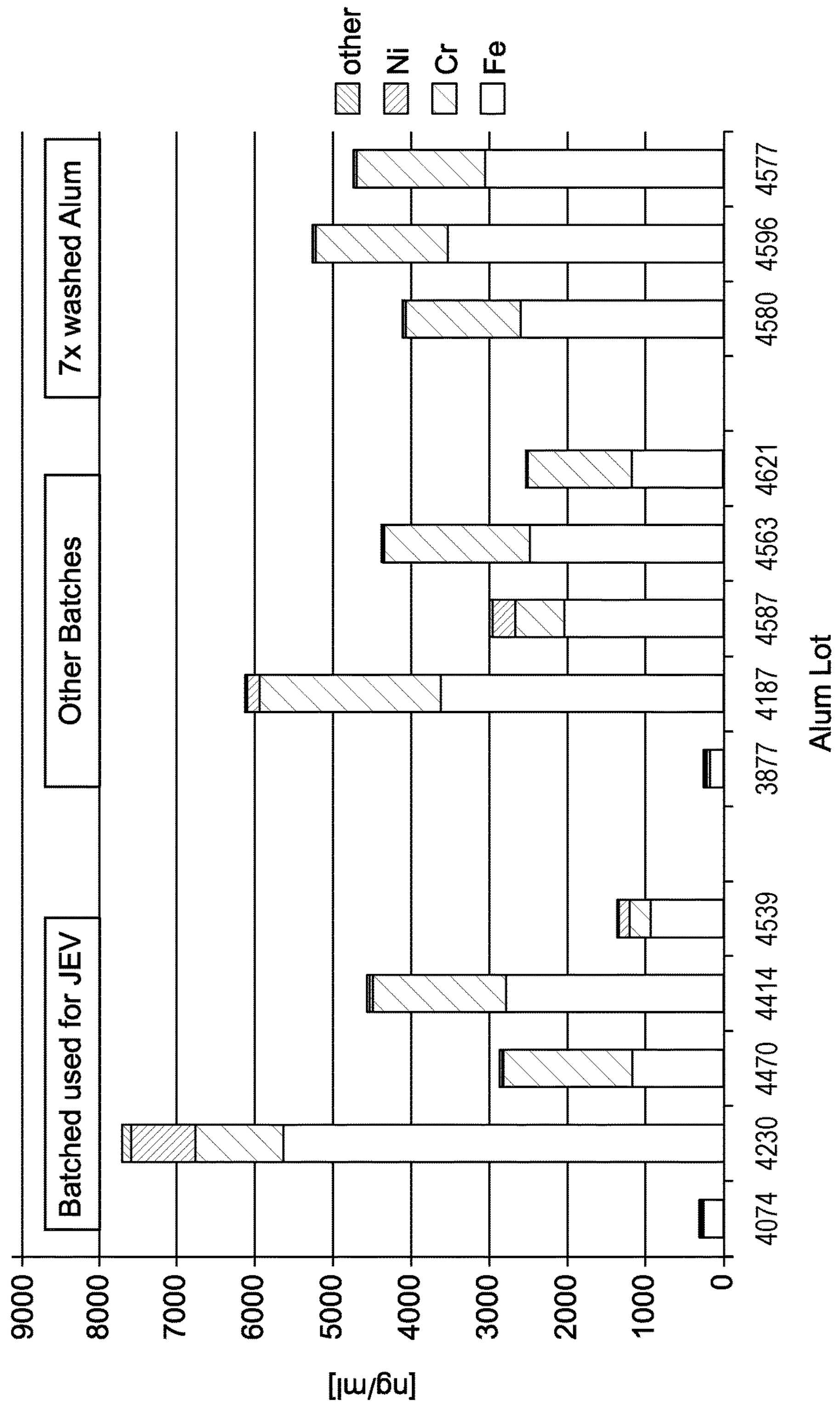
FIG. 13: Overview of tested ALHYDROGEL® batches. Total concentration of contaminating metal ions in ng/mL and share of the main metal ions Fe, Cr and Ni are shown.

FIG. 13 shows a comparison of the different ALHYDROGEL® lots analyzed. The total contaminating metal ion content for all tested contaminating elements are shown with the absolute shares for the three major metals Fe, Cr and Ni depicted in different colors. As can be seen lot 4074 has very little contaminating metal ions compared to the majority of the other analyzed batches. Only lot 3877 showed a similar lot contamination whereas lot 4230 shows by far the highest contamination of all batches analyzed during this investigation.

During the investigational testing a large variation in the metal ion content was observed between different batches of ALHYDROGEL® (see FIG. 13). To test if these contaminating metal ions are located in the Aluminum hydroxide fraction or in the supernatant Lot 4230 was separated into a supernatant and a sediment fraction (see Table 24). As can be seen less than 2% of the metal ions could be detected in the supernatant indicating that all contaminating metal ions are either bound to the Aluminum hydroxide particle surface or inside the particle structures. The local metal ion concentration can therefore be estimated to be at least 50-100 times higher since the solid volume fraction (volume of Alum-pellet after centrifugation) of 0.1% Al2O3 (corresponding 0.5 mg/mL Al) used in JEV vaccine formulation is approx. 10-20 μL per 1000 μL of FVL.

5 Summary

ALHYDROGEL® is used in a 0.1% final concentration as adjuvant in the current JEV vaccine formulation. During the investigation of an out-of-specification (OOS) potency result for production FVL JEV09L37 an evaluation of the ALHYDROGEL® production process was initiated. A total of 13 different ALHYDROGEL® lots were analyzed for the presence of contaminating metal ions that could reduce protein stability.

Large variations in the concentration of a number of metal ions were observed for different ALHYDROGEL® lots. When analyzing the raw materials it was shown that these contaminations were present at the same concentration as found within the ALHYDROGEL®.

Higher levels of Fe, Ni and Cu ions were noted in ALHYDROGEL® lot 4230 when compared to the other investigated lots. Lot 4230 was the only one where residual Cu ions were detected. This lot 4230 was used for the formulation of FVL JEV09L37.

When analyzing supernatant and insoluble fraction of an ALHYDROGEL® batch these contaminating metal ions could only be found in the precipitate indicating that these ions are either bound to the Aluminum hydroxide particle surface or actually part of the particle.

Although macroscopic and in composition different from other ALHYDROGEL® lots used for JEV production, lot 4230 fulfilled all requirements detailed by the Ph. Eur. Also physical characterization (particle size distribution and point of zero charge) showed no differences between lot 4230 and other ALHYDROGEL® lots not showing these high metal ion contaminations.

Example 4

1.1. Materials, Equipment and Methods 1.2. Equipment

Analytical balance (readability of 0.1 mg; e.g. Mettler Toledo XP205DR/M)

Precision balance (readability of 0.1 g; e.g. Mettler Toledo, Model No XS6002S Delta Range)

Filter Units 0.22 μm (e.g. Stericup Cat No SCGPV01RE) or 0.2 μm filter system (e.g. 50 mL Millipore Steriflip)

Freezer (−20° C.) and Ultra-Freezer (−80° C.)

Fridge (+2 to 8° C.)

Magnetic stirrer (e.g. KIKA Labortechnik RCT basic) and magnetic stir bars

Microplate Washer: e.g. BioTek ELx405

Microplate Reader: e.g. BioTek Synergy 2 and Gen5 Secure software

Microplate Incubator (37° C.)

Microtiter Sealing tape (e.g. Thermo Electron 9503130)

Multichannel pipettes and tips (e.g. Eppendorf Research Pro 50-120044,

Eppendorf Research, 10-100 μL)

pH meter (e.g. WTW Series ino Lab, Terminal 740 and pH/Cond. 740)

Pipettes and tips (e.g. Eppendorf Research, 0.5-10 μL, 2-20 μL, 20-200 μL, 100-1000 μL, 500-5000 μL)

Pipettor (e.g. IBS Biosciences Pipetboy)

PP Tubes 15 mL (e.g. Sarstedt 62.515.006) or PP tubes 50 mL (e.g. Greiner 227261)

Reagent Reservoir 50 mL (e.g. Corning Incorporated 4870)

Serological pipettes (e.g. Falcon, 2 mL, 5 mL, 10 mL, 25 mL, 50 mL)

Titertube Micro Tubes—Bulk (BioRad 223-9391)

Vortex mixer (e.g. VWR Analog Vortex Mixer, Model No 945304)

1.5 mL or 2.0 mL Eppendorf LoBind tubes (Cat No 0030 108.116, Cat No 0030 108.132, respectively)

96 well Microplate (F96 Cert. Maxisorp Nunc-Immuno-plates)

For Analysis of DP Samples in Addition:

Bench top centrifuge (e.g. Beckman coulter, Microfuge 16 Centrifuge, Cat No A46473)

Orbital shaker (e.g. Eppendorfer Thermomixer compact)

50 mL PP tubes (e.g. Greiner 227261)

1.3. Reagents

PBS 10× (e.g. Gibco, Cat. No 14200-083)

Tween 20 (e.g. Sigma Cat. No P7949)

2M Sulphuric Acid (Volumetric solution, e.g. Fisher, Cat. No. J/8410/17)

De-ionised water, e.g. (Milli-Q, 18.20)

Sodium carbonate—bicarbonate capsules (e.g. Sigma, Cat. No. C3041)

Hydrochloric acid (HCl) 1 mol/L (e.g. Merck, Cat. No 1.09057.1000)

Sodium hydroxide (NaOH) 1 mol/L (e.g. Merck, Cat. No 1.09132.1000)

Glycerol (e.g. Sigma)

For Analysis of DP Samples in Addition:

Di-potassium hydrogen phosphate trihydrate (e.g. Sigma, Cat No. P5504)

Potassium di-hydrogen phosphate (e.g. VWR, AnalaR Normapur, Cat No. 26936.260)

Albumin, Bovine Serum (BSA), ELISA grade (e.g. Sigma, Cat. No. A3059)

TMB Substrate (e.g. BioFX, TMBW-1000-01)

Donkey anti rabbit IgG HRP Conjugate (Jackson Immuno Research, Cat No 711-035-152)

Reconstitution:

The content of 1 vial (0.4 mg) is reconstituted in 0.5 mL of de-ionised water and thoroughly mixed until total dissolution. Add 0.5 mL of Glycerol and mix it further until homogeneity. Aliquots are stored at −20° C. until use.

Inactivated JEV Reference Standard (Intercell Biomedical Ltd.)

Purified sheep anti-JEV (Intercell Biomedical Ltd.)

Purified rabbit anti-JEV (Intercell Biomedical Ltd.)

1.4. Solutions a) 0.05M carbonate buffer at pH 9.6 (used for coating of ELISA plates) For 100 mL buffer, dissolve one bi-carbonate/carbonate buffer capsule in 100 mL de-ionised water. Check the pH and adjust to 9.6±0.1 with HCl or NaOH if required. Use on the day of preparation only. Keep ELISA coating buffer at RT during the day of use, then discard.

b) ELISA wash buffer and part of block/sample diluent (PBS-T)

Prepare approximately 1 liter for every plate used. Dilute 10×PBS stock 1+9 in de-ionised water, mix well and check pH (7.4+/−0.1), adjust with 1M HCl or 1M NaOH as required. Add 0.05% (v/v) TWEEN® 20, mix well.

e.g. ELISA wash buffer (PBS-T) [1 L]:

| | |
|---|---|
| 100 mL | 10x PBS |
| 900 mL | de-ionised water |

Mix well, check/adjust pH (7.4+/−0.1).

0.5 mL TWEEN® 20

Mix well.

Use on the day of preparation only; keep ELISA wash buffer at RT during the day of use, then discard.

c) Blocking solution: 5% BSA in PBS-T

Prepare approximately 25 mL for every plate. Measure required quantity of PBS-T into a clean glass bottle using a serological pipette. Add a clean magnetic stir bar. Weigh the required amount of BSA, add to the surface of the PBS-T and mix gently on a magnetic stirrer until all the BSA has gone into solution. Filter solution using a 0.2 μm filter (either Steriflip filter system or syringe filter).

e.g. Blocking solution [100 mL]

| | |
|---|---|
| 5 g | BSA |
| 100 mL | PBS-T |

Use on the day of preparation only; keep blocking solution at RT during the day of use then discard.

d) Sample diluent: 1% BSA in PBS-T

Prepare as above but using 1 g of BSA per 100 mL PBS-T, approximately 25 mL is required per plate.

e.g. Sample diluent [100 mL]

| | |
|---|---|
| 1 g | BSA |
| 100 mL | PBS-T |

Use on the day of preparation only; keep sample diluent at RT during the day of use, then discard.

For Analysis of DP Samples in Addition:

e) 1×PBS

Prepare 1 part 10×PBS with 9 parts de-ionised water e.g. 1×PBS [100 mL]

10 mL 10×PBS 90 mL de-ionised water

Use on the day of preparation only; keep 1×PBS at RT during the day of use, then discard.

f) 20×ELISA buffer

Weigh an appropriate amount of BSA into a suitable container to make a 20× solution. Add the appropriate volume of 1×PBS. Add TWEEN® 20 to a final concentration of 0.05% Mix on the magnetic stirrer until the BSA is fully dissolved. Filter the solution through a 0.2 μm filter (using either STERIFLIP filter system or syringe filter) into a sterile container (and aliquoted as needed).

e.g. 20×ELISA Buffer [25 mL]

| | |
|---|---|
| 5 g | BSA |
| 25 mL | 1xPBS |
| 12.5 μL | TWEEN ® 20 |

The solution can be stored at +2-8° C. for 1 week.

g) 2×ELISA buffer

It is prepared by dilution of the 20×ELISA Buffer with 1×PBS (1 part 20× ELISA Buffer and 9 part 1×PBS).

e.g. 2×ELISA Buffer [20 mL]

2 mL 20×ELISA Buffer 18 mL 1×PBS

Use on the day of preparation only; keep 2×ELISA buffer at RT during the day of use, then discard.

h) Desorption buffer

Potassium phosphate stock solution: Make a 3× stock solution of potassium phosphate (2.4M) by dissolving the appropriate volume of di-potassium phosphate trihydrate and of potassium dihydrogen phosphate in de-ionised water. Place on a magnetic stirrer and once dissolved make up the required volume, check that the pH of the solution is 8.0+/−0.1. Filter through a 0.2 μm filter.

e.g. 3× stock solution of Potassium phosphate (2.4M) [50 mL]

| | |
|---|---|
| 23.963 g | Di-potassium phosphate trihydrate |
| 2.041 g | Potassium dihydrogen phosphate |

Make up to 50 mL De-ionised water

Store at +2°-8° C. for up to 1 month.

Make working strength desorption buffer (0.8M potassium phosphate buffer containing 1% BSA and 0.05% TWEEN® 20) by adding the appropriate volume of potassium phosphate stock (2.4M), of TWEEN® 20 and of BSA to the required volume of de-ionised water. Mix thoroughly and use on the day of preparation.

e.g. working strength desorption buffer [15 mL]

| | |
|---|---|
| 5 mL | Potassium Phosphate (2.4M) |
| 7.5 μL | TWEEN ® 20 |
| 0.15 g | BSA |
| 10 mL | De-ionised water |

Keep working strength desorption buffer at RT during the day of use.

1.5. Test Samples and Antibodies

Test Samples:

Drug Substance and/or NIV (various batches)

JEV Vaccine samples (final hulk vaccine and final vaccine lot)

Inactivated JEV Reference Standard (Neutralised Inactivated Virus—NIV) (Intercell Biomedical Ltd.)

Polyclonal Antibodies:

Coating antibody: Purified Sheep anti-JEV (Intercell Biomedical Ltd.)

Primary detection antibody: Purified Rabbit anti-JEV (Intercell Biomedical Ltd.)

Secondary conjugated antibody: Donkey anti-Rabbit HRP Conjugate (Jackson Immuno Research Cat. No 711-035-152)

2 Procedure 2.1. Plate Coating

Label the plate with plate number, date and analyst.

Prepare fresh 0.05M carbonate buffer (pH 9.6) on the day of plate coating. Allow approximately 12 mL for each plate coated.

Remove the required number of aliquots of the coating antibody from the freezer and allow thawing at RT. Prepare a dilution of. Purified Sheep anti-JEV in carbonate buffer. Mix well by inversion of the tube.

Using the multichannel pipette, apply 100 μL/well to a 96-well Maxisorp plate within 15 min of preparation of the antibody dilution.

Cover with microtiter sealing tape and incubate 17 to 72 hrs at +2-8° C.

2.2. Washing

Remove plate from the refrigerator and allow warming to room temperature.

Wash the plate/s with the Microtiter plate washer 3 times using the respective wash program (3004 per well, three times, final dispense). After that: remove any remaining wash buffer by decanting. Invert the plate and blot it against a clean paper towel. Do not allow microtiter plate to dry between wash steps and reagent addition.

2.3. Blocking

Prepare a Blocking Solution 5% (w/v) of BSA in PBS-T as above.

Apply 200 μL Blocking Solution per well, cover the plate(s) with a cover plate and incubate at 37° C. for 1 hour+/−10 min.

2.4. Preparation of Standard Curve Dilutions

Remove the NIV reference standard from the freezer, allow thawing at RT, mix well. Prepare a 1 AU/mL stock dilution of the current reference standard; use at least 20 μL of NIV reference standard for dilution. e.g. NIV reference standard Pre-dilution:

Concentration: 235 AU/mL (lot No 03/2009)

To prepare a 1 AU/mL working standard solution dilute it 1 to 235 in sample diluent:

| | |
|---|---|
| 4680 μL | sample diluent |
| 20 μL | NIV reference standard |

Prepare then the following working standard solutions from the 1 AU/mL pre-dilution:

0.8 AU/mL, 0.6 AU/mL, 0.4 AU/mL, 0.2 AU/mL, 0.1 AU/mL and 0.05 AU/mL in sample diluent.

2.5. Quality Control Samples a) Quality control (QC) samples (for example at 0.75, 0.30 and 0.18 AU/mL) should be made from the NIV reference standard pre-dilution freshly at the time of the assay then discarded once used.

b) These controls are part of the system suitability criteria and allow the performance of the assay to be monitored over time.

2.6. Preparation of Test Samples

Drug Substance Preparation

Drug substance test samples are received for testing at unknown concentrations. These will be tested at six dilutions in triplicate. The dilutions will be made independently into the range of the standard curve, e.g. pre-dilution of 1 in 15 or other suitable dilution then six dilutions with sample buffer.

NIV Sample Preparation

NIV samples will be received for testing at unknown concentrations and pre-diluted in the range of the standard curve (e.g. 1 in 30 or other suitable dilution) then diluted six times in the same manner as the DS samples.

Drug Product Supernatant Preparation a) For the analysis of Bulk-DP samples mix well sample by vortexing. Transfer exactly 1 mL into a 1.5 mL LoBind Eppendorf tube.

For the analysis of final product container samples transfer the content of 2 syringes (0.6 mL per syringe) of the same lot into a 1.5 mL LoBind Eppendorf Tube. Mix content of tube thoroughly by inversion to ensure homogeneity of the DP and transfer exactly 1 mL into fresh 1.5 mL LoBind Eppendorf tube.

b) Centrifuge tubes containing 1 mL DP each at 3300×g for 5 minutes.

c) For each sample, pipette 25 μL of 20×ELISA buffer into fresh LoBind Eppendorf tube.

d) Carefully remove 475 μL of the supernatant without disturbing the alum pellet and transfer into the tube containing the 20×ELISA buffer. Mix gently by inversion. Re-spin 2 min at 16,000×g. Store sample at +2-8° C. prior to analysis.

NOTE: DP supernatant samples prepared in this way should be measured neat in triplicate in the inactivated JEV ELISA.

e) Carefully remove as much of the residual supernatant from the centrifuged tube using a 10-200 μL pipette without disturbing the alum pellet and discard the supernatant.

f) The pellet obtained is subjected to the Desorption procedure as described below.

Drug Product Desorption Procedure a) Add 158 μL of working strength desorption buffer to each pellet left in the LoBind tube.

b) Resuspend the pellet by pipetting up and down several times to ensure complete re-suspension of the pellet and homogenisation of the sample.

c) Incubate samples for 10 min at RT on an orbital shaker at 500 rpm.

d) After incubation centrifuge samples at 3300×g for 5 minutes.

e) For each sample pipette 250 μL of 2×ELISA buffer into a fresh LoBind Eppendorf tube.

f) Carefully remove 83.3 μL from the upper part of the supernatant containing the desorbed product without disturbing the pellet and transfer into the tube containing the 2×ELISA buffer. Remove remaining supernatant using a 20-200 μL pipette without disturbing the pellet and discard the supernatant.

g) Add another 1584 of working strength desorption buffer to each pellet.

h) Carry out 2 more desorption cycles (3 in total) pooling the 3×83.34 of the desorbed material+250 μL ELISA buffer into the appropriate tube. After the last step the remaining pellet can be discarded.

i) The final concentration of the viral antigen in the desorbed pool(s) should now be the same as the original 1 mL of DP from which it was desorbed. Therefore, the concentration of inactivated JEV antigen content measured in the desorbed pool can be directly related to the original DP.

Note: Analyse the desorbed samples by ELISA on the day of desorption.

j) Dilution of desorbed DP samples:

These will be tested at six dilutions in triplicate. An appropriate pre-dilution will be performed in the range of the standard curve e.g. 1 in 15 (100 μL to 1400 μL diluent) or other suitable dilution, then six dilutions of 1 in 15 pre-dilution will be made independently using sample diluent.

2.7. Sample Loading and Plate Plan

Prepare samples and standards before analysis.

After blocking wash the plate using the plate washer employing the JEV ELISA program. After that, remove any remaining wash buffer by decanting. Invert the plate and blot it against a clean paper towel. Do not allow microtiter plate to dry between wash steps and reagent addition.

Add 100 μL/well of standards/controls/samples and cover with cover plate and incubate for 1 hour+/−10 min at 37° C.

Add 100 μL of sample diluent to all wells not required for testing.

2.8. Preparation of Primary Antibody

Remove the required number of aliquots of the primary antibody from the freezer and allow to thaw at RT. Prepare max 15 min before use Rabbit anti-JEV in sample diluent at a suitable dilution. Following sample incubation, wash the plate using the plate washer employing the JEV ELISA program. After that, remove any remaining wash buffer by decanting. Invert the plate and blot it against a clean paper towel. Do not allow microtiter plate to dry between wash steps and reagent addition.

Add 100 μL/well of diluted primary antibody, cover with cover plate and incubate for 1 hour+/−10 min at 37° C.

2.9. Preparation of Secondary Antibody Conjugate

Remove the required number of aliquots of the secondary antibody conjugate from the freezer and allow to thaw at RT. Prepare max 15 min before use a dilution of Donkey anti-Rabbit-HRP in sample diluent; e.g. for a 1 in 10,000 dilution for make a 1 in 100 pre-dilution then make a second dilution of 1 in 100.

Following primary antibody incubation, wash the plate using the plate washer employing the JEV ELISA program. After that, remove any remaining wash buffer by decanting. Invert the plate and blot it against a clean paper towel. Do not allow microtiter plate to dry between wash steps and reagent addition. Add 100 μL/well of diluted secondary antibody conjugate, cover with cover plate and incubate for 1 hour+/−10 min at 37° C.

2.10. Substrate Incubation

When the conjugate has been added, remove TMB from the 2-8° C. refrigerator. Pipette the required volume (12 mL of TMB per plate) into a 50 mL centrifuge tube, using a serological pipette. Allow the TMB to reach room temperature in the dark. Following conjugate incubation wash the plate 3 times with the plate washer employing the JEV ELISA program. After that: remove any remaining wash buffer by decanting. Invert the plate and blot it against a clean paper towel. Do not allow microtiter plate to dry between wash steps and reagent addition. Add 100 μL/well of TMB and develop the plate in the dark at Room Temperature for 10 minutes.

2.11. Stopping and Reading

After 10 minutes of TMB incubation, stop the development by adding 100 μL/well 2M sulphuric acid. Read the plate at 450 nm (reference filter 630 nm) within 10 minutes of stopping using the BioTek reader and Gen5 Secure software.

2.12. Data Analysis

NIV/DS Data Analysis:

Gen5Secure software will be used to calculate the % Recovery of the QCs, concentration×dilutions, mean concentration of the samples corrected for dilutions and this value multiplied by 1.05 to correct for the addition of ELISA buffer.

DP Data Analysis:

Gen5Secure software will be used to calculate the % Recovery of the QCs, concentration×dilutions and mean concentration of the dilutions for the samples.

For DP Supernatant Samples:

If the concentration of the supernatant sample is below the LLOQ of the assay (i.e. 0.05 AU/ml), then the supernatant sample should be recorded as <0.05 AU/ml If the concentration of the supernatant sample is within the LOQs of the assay (i.e. 0.05 AU/ml to 1.25 AU/ml), the concentration value is recorded for the supernatant sample.

If the concentration of the supernatant sample is above the ULOQ of the assay (i.e. 1.25 AU/ml), the preparation of the drug product supernatant should be repeated. The supernatant sample will be re-tested by performing a suitable pre-dilution into the range of the standard curve followed by 6 sample dilutions. (The desorbed Drug Product sample does not need to be repeated.) The mean concentration for the dilutions that are within the LOQs of the assay (LLOQ 0.05 AU/ml to 1.25 AU/ml) will be the recorded concentration value for the supernatant sample, provided that the system suitability are met and at least 4 out of the 6 sample dilutions are within the LOQs.

2.13. Assay Acceptance Criteria a) The correlation coefficient for the calibration curve must be >0.980.

b) % CVs≤15% for standards and samples (except DP supernatant) for the four highest concentrations of the dilutions, % CV≤15% for controls c) Individual blank ODs must be ≤0.2.

d) Assay controls must be within specified defined limits (for freshly prepared controls 2 out of 3 QCs should have observed concentrations within ±30% of the nominal values; OR the levels set during QC qualification) for the assay to pass.

e) Assay validity will be recorded on the Gen5-print-out. If the plate fails to meet the defined acceptance criteria the assay is deemed invalid.

2.14. Reporting of Data

NIV a) Antigen Content

The reported value for inactivated AU/mL is the mean of the concentrations (which are within the LOQs of 0.04 to 1.25 AU/mL) calculated for the single sample dilutions corrected by the respective dilution factors, and the mean multiplied by a correction factor of 1.05 to account for the 5% volume of 20× ELISA buffer that was added to each sample when it was taken. Antigen content will be recorded on Gen5 print-out.

DS:

a) Identity

If the absorbances of the samples at lowest dilution (highest concentration) are higher than 3 standard deviations above the mean value of the blank the result will be reported as positive b) Antigen Content The reported value for inactivated AU/mL is the mean of the concentrations (which are within the LOQs of 0.04 to 1.25 AU/mL) calculated for the single sample dilutions corrected by the respective dilution factors, and the mean multiplied by a correction factor of 1.05 to account for the 5% volume of 20× ELISA buffer that was added to each sample when it was taken. Antigen content will be recorded on Gen5 print-out.

Desorbed DP:

a) Identity:

If the absorbances of the samples at lowest dilution (highest concentration) are higher than 3 standard deviations above the mean value of the blank the result will be reported as positive.

b) Antigen Content

The reported value for inactivated AU/mL is the mean of the concentrations (which are within the LOQs of 0.05 to 0.8 AU/mL) calculated for the single sample dilutions corrected by the respective dilution factors. Antigen content will be recorded on Gen5 print-out.

DP Supernatant (Degree of Adsorption/Degree of Non-Adsorption):

Degree of adsorption is reported in relationship to aluminium hydroxide formulated drug substance post filtration.

a) For calculation of the reported value, the reported antigen content (AU/mL) for the respective DS sample (post filtration) corrected for the dilution with aluminium hydroxide (5%) will be set at 100% and the percentage of the concentration measured in the supernatant (corrected for the addition of 5% ELISA buffer) calculated in relation to that. The reportable value will be the difference between 100% and the percentage calculated for the supernatant. Results will be reported to 2 decimal places.

$$\text{Degree of adsorption (\%)} = 100\% - \frac{DP \text{ supernatant (AU/mL)} * 1.05}{DS \text{ (AU/mL)} * 0.95} * 100\%$$

The degree of non-adsorption will be calculated as detailed below and results will be reported to 2 decimal places:

$$\text{Degree of non-adsorption (\%)} = \frac{DP \text{ supernatant (AU/mL)} * 1.05}{DS \text{ (AU/mL)} * 0.95} * 100\%$$

b) In case the neat supernatant does not contain any measurable antigen (i.e. observed supernatant concentration less than LLOQ, where LLOQ=0.05 AU/mL), the LLOQ will be used for the calculation of the result. The result in this case is reported as "greater than x %". For example if the DS sample is measured as 12.00 AU/mL and no signal was measured in the supernatant; with the LLOQ of 0.05 AU/mL then amount in supernatant is <0.05*1.05=<0.0525 AU/mL. The amount of DS after buffer correction is 12.00*0.95=11.40 AU/mL, and the reported result for degree of adsorption is <100−0.0525/11.4*100=>99.54%. The degree of non-adsorption will also be reported (i.e. 100−the % degree of adsorption).

Example 5

Introduction:

In order to further investigate the mode of action that leads to product instability/potency loss of the JEV vaccine, Ala-(His)6-OprF190-342-OprI21-83 (SEQ ID NO: 1, FIG. 14)—herein also referred to as "protein A" was used in a preliminary screening assay incorporating ALHYDROGEL® lots with different metal content and spiking with copper ions and sulfite.

Material:

- Copper(II)chloride dihydrate (Sigma, Order no. 807483)
- 10×PBS (Gibco, Order No. 14200-091)
- 15 ml Falcon tubes (Greiner, Cat. No. 188724)
- Incubator infors HT Incubator Multitron Standard (InforsAG)
- Aqua bidest. (Fresenius Kabi, Art no. 0712221/01 A)

Preparation of Stock Solutions:

Copper(II) stock solution 20 mM Copper(II) stock solution was prepared by dissolving 341 mg of Copper(II)chloride dihydrate in 100 mL of aqua bidest.

Sodiummetabisulfite stock solution 200 mM Sodiummetabisulfite stock solution was prepared by dissolving 1.52 g of Sodiummetabisulfite in 35 mL PBS. This solution was adjusted the pH to 7.3 with NaOH and filled up to a volume of 40 mL with PBS. The solution was them filtered via 0.2μ syringe filter.

Preparation of Working Solutions

Working solutions were prepared by dilution of metal stock solutions with aqua bidest. and sterile filtration via 0.2μ syringe filter. (Mini Kleenpak 25 mm-Pall)

Preparation of Buffer Solutions

⅓ PBS+0.9% NaCl

1×PBS buffer solution was prepared by 1:10 dilution of 10×PBS with aqua bidest. The pH of this buffer solution was 7.5. PBS buffer solutions adjusted to pH 7.3 and 8.0 were prepared by adjusting the pH with HCl or NaOH respectively.

9 g of NaCl were dissolved in 333 mL of either pH 7.3 of pH 8.0 buffer solution and then brought to 1000 mL with aqua bidest. followed by filtration via 0.2μ bottle-top filter.

Sample Preparation:

Formulations of Protein A and different lots of ALHYDROGEL® (Lot 4230 & Lot 4074) were prepared in ½ PBS+0.9% NaCl at two different pH values and were spiked with sulfite according to the following scheme:

| Sample | | | | Spike | |
|---|---|---|---|---|---|
| No. | Name | pH | Alum batch | Cu(II) [ng/mL] | Sulfit [mM] |
| 1 | 17112011_PROTEIN A_4074_ref_4°_pH 7.3 | 7.3 | 4074 | | |
| 2 | 17112011_PROTEIN A_4074_ref_37°_pH 7.3 | 7.3 | 4074 | | |
| 3 | 17112011_PROTEIN A_4074_Sulfit_37°_pH 7.3 | 7.3 | 4074 | | 1 |
| 4 | 17112011_PROTEIN A_4230_ref_4°_pH 7.3 | 7.3 | 4230 | | |
| 5 | 17112011_PROTEIN A_4230_ref_37°_pH 7.3 | 7.3 | 4230 | | |

-continued

| Sample | | | | Spike | |
|---|---|---|---|---|---|
| No. | Name | pH | Alum batch | Cu(II) [ng/mL] | Sulfit [mM] |
| 6 | 17112011_PROTEIN A_4230_Sulfit_37°_pH 7.3 | 7.3 | 4230 | | 1 |
| 7 | 17112011_PROTEIN A_4074_ref_4°_pH 8 | 8 | 4074 | | |
| 8 | 17112011_PROTEIN A_4074_ref_37°_pH 8 | 8 | 4074 | | |
| 9 | 17112011_PROTEIN A_4074_Sulfit_37°_pH 8 | 8 | 4074 | | 1 |
| 10 | 17112011_PROTEIN A_4230_ref_4°_pH 8 | 8 | 4230 | | |
| 11 | 17112011_PROTEIN A_4230_ref_37°_pH 8 | 8 | 4230 | | |
| 12 | 17112011_PROTEIN A_4230_Sulfit_37°_pH 8 | 8 | 4230 | | 1 |

Samples 1, 6, 11 and 16 were stored at 4° C. (reference samples). All other samples were incubated at 37° C. for 96 hours.
After 96 hours all samples were subjected to a desorption procedure to seperate the antigen from ALHYDROGEL ®. The desorbed antigen was analyzed by RPC.

Results:

Results showed severe degradation of the antigen Protein A in the presence of sulfite. The degradation was more pronounced in the samples formulated with ALHYDROGEL® of higher metal impurity content.

TABLE 1

Metal ion content in Aluminium hydroxide lot 4230 and 4074 analyzed by ICP-MS.

| Alum Lot (2% solution) | Al µg/mL | Cr ng/mL | Fe ng/mL | Co ng/mL | Ni ng/mL | Cu ng/mL | Ag ng/mL | Cd ng/mL | W ng/mL | Pb ng/mL | V ng/mL | Rb ng/mL | Mo ng/mL |
|---|---|---|---|---|---|---|---|---|---|---|---|---|---|
| Alum Lot 4230 RQCS 0890 | 9570 | 1139 | 5640 | 7 | 816 | 64 | <5 | <5 | <25 | 24 | 13 | <5 | 11 |
| Alum Lot 4074 RQCS0013 | 9130 | 20 | 266 | <5 | 15 | <25 | <5 | <5 | <25 | 19 | <5 | <5 | <5 |
| Mix 50/50% of both Lots* | 9130 | 579 | 2952 | <5.8 | 415 | <45 | <5 | <5 | <25 | 21.6 | <9 | <5 | <8 |

*Calculated residual metal content

TABLE 2

Pipetting scheme of DOE

| Sample | | | | % | % | µg/mL | U | ppm |
|---|---|---|---|---|---|---|---|---|
| No. | Name | pH | NIV dil | Alum 4230 | Alum 4074 | PS Frag. Stock | Extractables Stock | CH2O |
| 1 | 20110819__DOE__spl__1 | 7 | 2 | 100 | 0 | 50 | 4.2 | 0 |
| 2 | 20110819__DOE__spl__2 | 7 | 2 | 0 | 100 | 0 | 4.2 | 0 |
| 3 | 20110819__DOE__spl__3 | 7 | 2 | 0 | 100 | 0 | 0 | 40 |
| 4 | 20110819__DOE__spl__4 | 8 | 2 | 0 | 100 | 50 | 4.2 | 0 |
| 5 | 20110819__DOE__spl__5 | 7.5 | 2 | 50 | 50 | 50 | 0 | 0 |
| 6 | 20110819__DOE__spl__6 | 7 | 2 | 0 | 100 | 50 | 0 | 40 |
| 7 | 20110819__DOE__spl__7 | 7 | 2 | 100 | 0 | 50 | 0 | 0 |
| 8 | 20110819__DOE__spl__8 | 8 | 2 | 0 | 100 | 50 | 0 | 0 |
| 9 | 20110819__DOE__spl__9 | 8 | 2 | 100 | 0 | 0 | 0 | 0 |
| 10 | 20110819__DOE__spl__10 | 8 | 2 | 100 | 0 | 50 | 0 | 0 |
| 11 | 20110819__DOE__spl__11 | 8 | 2 | 0 | 100 | 50 | 4.2 | 40 |
| 12 | 20110819__DOE__spl__12 | 7 | 2 | 100 | 0 | 0 | 4.2 | 0 |
| 13 | 20110819__DOE__spl__13 | 8 | 2 | 0 | 100 | 0 | 0 | 40 |
| 14 | 20110819__DOE__spl__14 | 7 | 2 | 100 | 0 | 0 | 0 | 40 |
| 15 | 20110819__DOE__spl__15 | 8 | 2 | 0 | 100 | 0 | 4.2 | 0 |
| 16 | 20110819__DOE__spl__16 | 8 | 2 | 100 | 0 | 50 | 0 | 40 |
| 17 | 20110819__DOE__spl__17 | 7 | 2 | 0 | 100 | 50 | 4.2 | 0 |
| 18 | 20110819__DOE__spl__18 | 7 | 2 | 0 | 100 | 50 | 4.2 | 40 |
| 19 | 20110819__DOE__spl__19 | 8 | 2 | 100 | 0 | 0 | 4.2 | 40 |
| 20 | 20110819__DOE__spl__20 | 8 | 2 | 0 | 100 | 0 | 4.2 | 40 |
| 21 | 20110819__DOE__spl__21 | 8 | 2 | 0 | 100 | 50 | 0 | 40 |
| 22 | 20110819__DOE__spl__22 | 8 | 2 | 100 | 0 | 0 | 4.2 | 0 |
| 23 | 20110819__DOE__spl__23 | 7 | 2 | 0 | 100 | 0 | 4.2 | 40 |
| 24 | 20110819__DOE__spl__24 | 7 | 2 | 100 | 0 | 50 | 0 | 40 |
| 25 | 20110819__DOE__spl__25 | 7 | 2 | 0 | 100 | 50 | 0 | 0 |
| 26 | 20110819__DOE__spl__26 | 7 | 2 | 0 | 100 | 0 | 0 | 0 |
| 27 | 20110819__DOE__spl__27 | 8 | 2 | 100 | 0 | 50 | 4.2 | 0 |
| 28 | 20110819__DOE__spl__28 | 8 | 2 | 100 | 0 | 0 | 0 | 40 |
| 29 | 20110819__DOE__spl__29 | 8 | 2 | 100 | 0 | 50 | 4.2 | 40 |
| 30 | 20110819__DOE__spl__30 | 7 | 2 | 100 | 0 | 0 | 0 | 0 |
| 31 | 20110819__DOE__spl__31 | 7.5 | 2 | 50 | 50 | 0 | 0 | 0 |
| 32 | 20110819__DOE__spl__32 | 8 | 2 | 0 | 100 | 0 | 0 | 0 |
| 33 | 20110819__DOE__spl__33 | 7 | 2 | 100 | 0 | 50 | 4.2 | 40 |
| 34 | 20110819__DOE__spl__34 | 7 | 2 | 100 | 0 | 0 | 4.2 | 40 |

TABLE 2-continued

Pipetting scheme of DOE

| Sample | | | Volume [µl] | | | | | | | |
|---|---|---|---|---|---|---|---|---|---|---|
| No. | Name | pH | NIV | Buffer | Alum 4230 | Alum 4074 | PS Frag. Stock | Extractables Stock | CH2O | Total |
| 1 | 20110819_DOE_spl_1 | 7 | 2500 | 1812 | 250 | 0 | 125 | 313 | 0 | 5000 |
| 2 | 20110819_DOE_spl_2 | 7 | 2500 | 1937 | 0 | 250 | 0 | 313 | 0 | 5000 |
| 3 | 20110819_DOE_spl_3 | 7 | 2500 | 2228 | 0 | 250 | 0 | 0 | 22 | 5000 |
| 4 | 20110819_DOE_spl_4 | 8 | 2500 | 1812 | 0 | 250 | 125 | 313 | 0 | 5000 |
| 5 | 20110819_DOE_spl_5 | 7.5 | 2500 | 2125 | 125 | 125 | 125 | 0 | 0 | 5000 |
| 6 | 20110819_DOE_spl_6 | 7 | 2500 | 2103 | 0 | 250 | 125 | 0 | 22 | 5000 |
| 7 | 20110819_DOE_spl_7 | 7 | 2500 | 2125 | 250 | 0 | 125 | 0 | 0 | 5000 |
| 8 | 20110819_DOE_spl_8 | 8 | 2500 | 2125 | 0 | 250 | 125 | 0 | 0 | 5000 |
| 9 | 20110819_DOE_spl_9 | 8 | 2500 | 2250 | 250 | 0 | 0 | 0 | 0 | 5000 |
| 10 | 20110819_DOE_spl_10 | 8 | 2500 | 2125 | 250 | 0 | 125 | 0 | 0 | 5000 |
| 11 | 20110819_DOE_spl_11 | 8 | 2500 | 1790 | 0 | 250 | 125 | 313 | 22 | 5000 |
| 12 | 20110819_DOE_spl_12 | 7 | 2500 | 1937 | 250 | 0 | 0 | 313 | 0 | 5000 |
| 13 | 20110819_DOE_spl_13 | 8 | 2500 | 2228 | 0 | 250 | 0 | 0 | 22 | 5000 |
| 14 | 20110819_DOE_spl_14 | 7 | 2500 | 2228 | 250 | 0 | 0 | 0 | 22 | 5000 |
| 15 | 20110819_DOE_spl_15 | 8 | 2500 | 1937 | 0 | 250 | 0 | 313 | 0 | 5000 |
| 16 | 20110819_DOE_spl_16 | 8 | 2500 | 2103 | 250 | 0 | 125 | 0 | 22 | 5000 |
| 17 | 20110819_DOE_spl_17 | 7 | 2500 | 1812 | 0 | 250 | 125 | 313 | 0 | 5000 |
| 18 | 20110819_DOE_spl_18 | 7 | 2500 | 1790 | 0 | 250 | 125 | 313 | 22 | 5000 |
| 19 | 20110819_DOE_spl_19 | 8 | 2500 | 1915 | 250 | 0 | 0 | 313 | 22 | 5000 |
| 20 | 20110819_DOE_spl_20 | 8 | 2500 | 1915 | 0 | 250 | 0 | 313 | 22 | 5000 |
| 21 | 20110819_DOE_spl_21 | 8 | 2500 | 2103 | 0 | 250 | 125 | 0 | 22 | 5000 |
| 22 | 20110819_DOE_spl_22 | 8 | 2500 | 1937 | 250 | 0 | 0 | 313 | 0 | 5000 |
| 23 | 20110819_DOE_spl_23 | 7 | 2500 | 1915 | 0 | 250 | 0 | 313 | 22 | 5000 |
| 24 | 20110819_DOE_spl_24 | 7 | 2500 | 2103 | 250 | 0 | 125 | 0 | 22 | 5000 |
| 25 | 20110819_DOE_spl_25 | 7 | 2500 | 2125 | 0 | 250 | 125 | 0 | 0 | 5000 |
| 26 | 20110819_DOE_spl_26 | 7 | 2500 | 2250 | 0 | 250 | 0 | 0 | 0 | 5000 |
| 27 | 20110819_DOE_spl_27 | 8 | 2500 | 1812 | 250 | 0 | 125 | 313 | 0 | 5000 |
| 28 | 20110819_DOE_spl_28 | 8 | 2500 | 2228 | 250 | 0 | 0 | 0 | 22 | 5000 |
| 29 | 20110819_DOE_spl_29 | 8 | 2500 | 1790 | 250 | 0 | 125 | 313 | 22 | 5000 |
| 30 | 20110819_DOE_spl_30 | 7 | 2500 | 2250 | 250 | 0 | 0 | 0 | 0 | 5000 |
| 31 | 20110819_DOE_spl_31 | 7.5 | 2500 | 2250 | 125 | 125 | 0 | 0 | 0 | 5000 |
| 32 | 20110819_DOE_spl_32 | 8 | 2500 | 2250 | 0 | 250 | 0 | 0 | 0 | 5000 |
| 33 | 20110819_DOE_spl_33 | 7 | 2500 | 1790 | 250 | 0 | 125 | 313 | 22 | 5000 |
| 34 | 20110819_DOE_spl_34 | 7 | 2500 | 1915 | 250 | 0 | 0 | 313 | 22 | 5000 |
| | | sum: | 85000 | 69014 | 4250 | 4250 | 2125 | 5015 | 346 | 170000 |

TABLE 3

Comparison of leachables from stopper extract and JEV09L37 SN. All peaks with an area of >0.1 mAU · min are included in this table.

| Retention time (min) | Stopper extract concentrate | Stopper extract concentrate 1:16 diluted in formulation | FVL L37 SN | Relative concentration compared to FVL (%) |
|---|---|---|---|---|
| | Peak area (mAU · min) | | | |
| 12.40 | 0.79 | 0.05 | 0.10 | 47 |
| 13.14 | 1.91 | 0.12 | n.d. | additional peak compared to FVL |
| 13.48 | 0.81 | 0.05 | n.d. | additional peak compared to FVL |
| 13.74 | 0.43 | 0.03 | n.d. | additional peak compared to FVL |
| 14.10 | 0.75 | 0.05 | n.d. | additional peak compared to FVL |
| 14.41 | 0.49 | 0.03 | 0.25 | 12 |
| 16.12 | 29.64 | 1.85 | 0.45 | 414 |
| 16.71 | 2.75 | 0.17 | n.d. | additional peak compared to FVL |
| 17.15 | 14.68 | 0.92 | 0.11 | 815 |
| 18.68 | 0.90 | 0.06 | 0.57 | 10 |
| 20.08 | 0.70 | 0.04 | 0.25 | 18 |
| 20.75 | 0.42 | 0.03 | n.d. | additional peak compared to FVL |
| 21.27 | 0.54 | 0.03 | n.d. | additional peak compared to FVL |
| 22.13 | 2.84 | 0.18 | 0.15 | 122 |
| 22.74 | 0.55 | 0.03 | 0.17 | 20 |
| 23.74 | 1.74 | 0.11 | 0.27 | 41 |
| 24.88 | 0.98 | 0.06 | 0.12 | 51 |
| 27.63 | 0.84 | 0.05 | 0.16 | 32 |
| 29.46 | 0.72 | 0.04 | n.d. | additional peak compared to FVL |
| 31.40 | 0.39 | 0.02 | n.d. | additional peak compared to FVL |
| 35.23 | 4.70 | 0.29 | 0.41 | 72 |
| SUM | 67.59 | 4.2 | 3.0 | 140 |

TABLE 4

DOE results obtained after 4 and 8 weeks at 22° C. Antigen was desorbed from Alum and analysed by ELISA (monoclonal and polyclonal). *(x-fold increase compared to FVL)

| | | | | | | 4 weeks at 22° C. | | | 8 weeks at 22° C. | | |
|---|---|---|---|---|---|---|---|---|---|---|---|
| Sample | pH | Alum 4230 (%) | Spiked PS Frag. (μg/mL) | Spiked leachables* | Spiked Formalin (ppm) | Mono. ELISA (AU/mL) | Poly. ELISA (AU/mL) | Ratio | Mono. ELISA (AU/mL) | Poly. ELISA (AU/mL) | Ratio |
| 1 | 7 | 100 | 50 | 1.4 | 0 | 9.725 | 12.814 | 0.76 | 6.342 | 3.649 | 0.575 |
| 2 | 7 | 0 | 0 | 1.4 | 0 | 15.254 | 16.331 | 0.93 | 9.865 | 8.039 | 0.815 |
| 3 | 7 | 0 | 0 | 0 | 40 | 12.457 | 12.614 | 0.99 | 9.037 | 8.176 | 0.905 |
| 4 | 8 | 0 | 50 | 1.4 | 0 | 13.513 | 12.971 | 1.04 | 10.328 | 9.533 | 0.923 |
| 5 | 7.5 | 50 | 50 | 0 | 0 | 13.592 | 14.924 | 0.91 | 10.358 | 8.032 | 0.775 |
| 6 | 7 | 0 | 50 | 0 | 40 | 12.942 | 13.878 | 0.93 | 10.008 | 9.896 | 0.989 |
| 7 | 7 | 100 | 50 | 0 | 0 | 9.649 | 12.608 | 0.77 | 6.089 | 4.092 | 0.672 |
| 8 | 8 | 0 | 50 | 0 | 0 | 11.184 | 11.902 | 0.94 | 9.113 | 9.048 | 0.993 |
| 9 | 8 | 100 | 0 | 0 | 0 | 11.436 | 12.883 | 0.89 | 8.858 | 7.409 | 0.836 |
| 10 | 8 | 100 | 50 | 0 | 0 | 13.361 | 15.516 | 0.86 | 10.525 | 8.158 | 0.775 |
| 11 | 8 | 0 | 50 | 1.4 | 40 | 13.209 | 13.608 | 0.97 | 9.349 | 9.201 | 0.984 |
| 12 | 7 | 100 | 0 | 1.4 | 0 | 8.4 | 11.913 | 0.71 | 5.001 | 2.951 | 0.590 |
| 13 | 8 | 0 | 0 | 0 | 40 | 10.294 | 10.483 | 0.98 | 8.019 | 8.284 | 1.033 |
| 14 | 7 | 100 | 0 | 0 | 40 | 9.972 | 12.015 | 0.83 | 7.435 | 5.802 | 0.780 |
| 15 | 8 | 0 | 0 | 1.4 | 0 | 14.096 | 15.618 | 0.9 | 10.192 | 9.531 | 0.935 |
| 16 | 8 | 100 | 50 | 0 | 40 | 9.78 | 13.514 | 0.72 | 11.011 | 8.947 | 0.813 |
| 17 | 7 | 0 | 50 | 1.4 | 0 | 11.213 | 14.285 | 0.78 | 10.246 | 8.377 | 0.818 |
| 18 | 7 | 0 | 50 | 1.4 | 40 | 11.183 | 11.499 | 0.97 | 10.539 | 9.217 | 0.875 |
| 19 | 8 | 100 | 0 | 1.4 | 40 | 10.536 | 10.935 | 0.96 | 10.151 | 8.341 | 0.822 |
| 20 | 8 | 0 | 0 | 1.4 | 40 | 10.026 | 9.654 | 1.04 | 11.306 | 9.281 | 0.821 |
| 21 | 8 | 0 | 50 | 0 | 40 | 10.149 | 9.986 | 1.02 | 11.213 | 9.205 | 0.821 |
| 22 | 8 | 100 | 0 | 1.4 | 0 | 10.051 | 12.193 | 0.82 | 10.918 | 6.841 | 0.627 |
| 23 | 7 | 0 | 0 | 1.4 | 40 | 10.024 | 10.74 | 0.93 | 10.711 | 7.963 | 0.743 |
| 24 | 7 | 100 | 50 | 0 | 40 | 9.535 | 10.254 | 0.93 | 10.642 | 6.991 | 0.657 |
| 25 | 7 | 0 | 50 | 0 | 0 | 11.143 | 11.765 | 0.95 | 13.054 | 8.684 | 0.665 |
| 26 | 7 | 0 | 0 | 0 | 0 | 11.431 | 11.796 | 0.97 | 13.753 | 10.391 | 0.756 |
| 27 | 8 | 100 | 50 | 1.4 | 0 | 10.09 | 11.953 | 0.84 | 11.506 | 7.334 | 0.637 |
| 28 | 8 | 100 | 0 | 0 | 40 | 10.137 | 11.223 | 0.9 | 11 | 8.131 | 0.739 |
| 29 | 8 | 100 | 50 | 1.4 | 40 | 9.605 | 10.535 | 0.91 | 10.848 | 7.939 | 0.732 |
| 30 | 7 | 100 | 0 | 0 | 0 | 6.485 | 8.379 | 0.77 | 7.957 | 3.523 | 0.443 |
| 31 | 7.5 | 50 | 0 | 0 | 0 | 11.081 | 12.229 | 0.91 | 12.377 | 9.535 | 0.770 |
| 32 | 8 | 0 | 0 | 0 | 0 | 11.421 | 12.002 | 0.95 | 11.36 | 9.859 | 0.868 |
| 33 | 7 | 100 | 50 | 1.4 | 40 | 9.03 | 10.583 | 0.85 | 9.753 | 6.571 | 0.674 |
| 34 | 7 | 100 | 0 | 1.4 | 40 | 9.05 | 10.927 | 0.83 | 11.715 | 6.872 | 0.587 |

TABLE 5

Analysis of Variance for ratio Monoclonal/Polyclonal ELISA after storage 4 weeks at 22° C.
Analysis of Variance for Ratio 4 weeks

| Source | Sum of Squares | Df | Mean Square | F-Ratio | P-Value |
|---|---|---|---|---|---|
| A: pH | 0.02205 | 1 | 0.02205 | 5.48 | 0.0326 |
| B: Alum | 0.117612 | 1 | 0.117612 | 29.20 | 0.0001 |
| C: PS Fragments | 0.0008 | 1 | 0.0008 | 0.20 | 0.6618 |
| D: Extractables | 0.0008 | 1 | 0.0008 | 0.20 | 0.6618 |
| E: Formaline | 0.0242 | 1 | 0.0242 | 6.01 | 0.0261 |
| AB | 0.0001125 | 1 | 0.0001125 | 0.03 | 0.8694 |
| AC | 0.00045 | 1 | 0.00045 | 0.11 | 0.7425 |
| AD | 0.01125 | 1 | 0.01125 | 2.79 | 0.1141 |
| AE | 0.00405 | 1 | 0.00405 | 1.01 | 0.3309 |
| BC | 0.0000125 | 1 | 0.0000125 | 0.00 | 0.9563 |
| BD | 0.0010125 | 1 | 0.0010125 | 0.25 | 0.6229 |
| BE | 0.0006125 | 1 | 0.0006125 | 0.15 | 0.7017 |
| CD | 0.0008 | 1 | 0.0008 | 0.20 | 0.6618 |
| CE | 0.0008 | 1 | 0.0008 | 0.20 | 0.6618 |
| DE | 0.0072 | 1 | 0.0072 | 1.79 | 0.1999 |
| Total error | 0.0644375 | 16 | 0.00402734 | | |
| Total (corr.) | 0.2562 | 31 | | | |

R-squared = 74.8488 percent
R-squared (adjusted for d.f.) = 51.2695 percent
Standard Error of Est. = 0.0634614
Mean absolute error = 0.0352734
Durbin-Watson statistic = 1.47556

TABLE 6

Analysis of Variance for ratio Monoclonal/Polyclonal ELISA after storage at 22° C. for 8 weeks.
Analysis of Variance for Ratio 8 weeks

| Source | Sum of Squares | Df | Mean Square | F-Ratio | P-Value |
|---|---|---|---|---|---|
| A: pH | 0.102378 | 1 | 0.102378 | 11.19 | 0.0041 |
| B: Alum | 0.275653 | 1 | 0.275653 | 30.13 | 0.0000 |
| C: PS Fragments | 0.00300312 | 1 | 0.00300312 | 0.33 | 0.5747 |
| D: Extractables | 0.0108781 | 1 | 0.0108781 | 1.19 | 0.2917 |
| E: Formaline | 0.0318781 | 1 | 0.0318781 | 3.48 | 0.0804 |
| AB | 0.00137813 | 1 | 0.00137813 | 0.15 | 0.7031 |
| AC | 0.00382812 | 1 | 0.00382812 | 0.42 | 0.5269 |
| AD | 0.00137813 | 1 | 0.00137813 | 0.15 | 0.7031 |
| AE | 0.0166531 | 1 | 0.0166531 | 1.82 | 0.1961 |
| BC | 0.000253125 | 1 | 0.000253125 | 0.03 | 0.8700 |
| BD | 0.00382813 | 1 | 0.00382813 | 0.42 | 0.5269 |
| BE | 0.00195313 | 1 | 0.00195313 | 0.21 | 0.6503 |
| CD | 0.00195313 | 1 | 0.00195313 | 0.21 | 0.6503 |
| CE | 0.000153125 | 1 | 0.000153125 | 0.02 | 0.8987 |
| DE | 0.00525313 | 1 | 0.00525313 | 0.57 | 0.4596 |
| Total error | 0.1464 | 16 | 0.00915 | | |
| Total (corr.) | 0.606822 | 31 | | | |

R-squared = 75.8743 percent
R-squared (adjusted for d.f.) = 53.2565 percent
Standard Error of Est. = 0.0956556
Mean absolute error = 0.0571484
Durbin-Watson statistic = 0.888586

TABLE 7

| Regression analysis for "Ratio 8 weeks" including pH, Alum and Formaldehyde. Regression coeffs. for Ratio 8 weeks | |
|---|---|
| constant = | 0.0228125 |
| A: pH = | 0.113125 |
| B: Alum = | −0.00185625 |
| E: Formaline = | 0.0315625 |

TABLE 8

Estimation of results "Ratio 8 weeks" generated using the fitted model.
Estimation Results for Ratio 8 weeks

| Row | Observed Value | Fitted Value | Lower 95.0% CL for Mean | Upper 95.0% CL for Mean |
|---|---|---|---|---|
| 1 | 0.58 | 0.5975 | 0.536766 | 0.658234 |
| 2 | 0.81 | 0.783125 | 0.722391 | 0.843859 |
| 3 | 0.9 | 0.84625 | 0.785516 | 0.906984 |
| 4 | 0.92 | 0.89625 | 0.835516 | 0.956984 |
| 6 | 0.99 | 0.84625 | 0.785516 | 0.906984 |
| 7 | 0.67 | 0.5975 | 0.536766 | 0.658234 |
| 8 | 0.99 | 0.89625 | 0.835516 | 0.956984 |
| 9 | 0.84 | 0.710625 | 0.649891 | 0.771359 |
| 10 | 0.78 | 0.710625 | 0.649891 | 0.771359 |
| 11 | 0.98 | 0.959375 | 0.898641 | 1.02011 |
| 12 | 0.59 | 0.5975 | 0.536766 | 0.658234 |
| 13 | 1.03 | 0.959375 | 0.898641 | 1.02011 |
| 14 | 0.78 | 0.660625 | 0.599891 | 0.721359 |
| 15 | 0.94 | 0.89625 | 0.835516 | 0.956984 |
| 16 | 0.81 | 0.77375 | 0.713016 | 0.834484 |
| 17 | 0.82 | 0.783125 | 0.722391 | 0.843859 |
| 18 | 0.88 | 0.84625 | 0.785516 | 0.906984 |
| 19 | 0.82 | 0.77375 | 0.713016 | 0.834484 |
| 20 | 0.82 | 0.959375 | 0.898641 | 1.02011 |
| 21 | 0.82 | 0.959375 | 0.898641 | 1.02011 |
| 22 | 0.63 | 0.710625 | 0.649891 | 0.771359 |
| 23 | 0.74 | 0.84625 | 0.785516 | 0.906984 |
| 24 | 0.66 | 0.660625 | 0.599891 | 0.721359 |
| 25 | 0.67 | 0.783125 | 0.722391 | 0.843859 |
| 26 | 0.76 | 0.783125 | 0.722391 | 0.843859 |
| 27 | 0.64 | 0.710625 | 0.649891 | 0.771359 |
| 28 | 0.74 | 0.77375 | 0.713016 | 0.834484 |
| 29 | 0.73 | 0.77375 | 0.713016 | 0.834484 |
| 30 | 0.44 | 0.5975 | 0.536766 | 0.658234 |
| 32 | 0.87 | 0.89625 | 0.835516 | 0.956984 |
| 33 | 0.67 | 0.660625 | 0.599891 | 0.721359 |
| 34 | 0.59 | 0.660625 | 0.599891 | 0.721359 |

TABLE 9

Plan for experiment 20110913(NIV)

Pipetting plan

| | | Stock Sol [mM] | |
|---|---|---|---|
| Total Volume: | 2000 µl | Ni(II)SO4 | 1 |
| NIV material: | 11A74 | Cu(II)Cl2 | 1 |
| | | Cr(III)Cl | 1 |

| Sample | | | µg/L | | | |
|---|---|---|---|---|---|---|
| | | | | | | fragmented |
| No. | Name | pH | Ni(II)SO4 | Cu(II)Cl2 | Cr(III) | PS |
| 1 | NIV_unspiked_pH7_22° C. | 7 | | | | |
| 2 | NIV_Ni(II)_100_pH7_22° C. | 7 | 100 | | | |
| 3 | NIV_Ni(II)_500_pH7_22° C. | 7 | 500 | | | |
| 4 | NIV_Ni(II)_1000_pH7_22° C. | 7 | 1000 | | | |
| 5 | NIV_Cu(II)_100_pH7_22° C. | 7 | | 100 | | |
| 6 | NIV_Cu(II)_500_pH7_22° C. | 7 | | 500 | | |
| 7 | NIV_Cu(II)_1000_pH7_22° C. | 7 | | 1000 | | |
| 8 | NIV_CR(III)_100_pH7_22° C. | 7 | | | 100 | |
| 9 | NIV_CR(III)_500_pH7_22° C. | 7 | | | 500 | |
| 10 | NIV_CR(III)_1000_pH7_22° C. | 7 | | | 1000 | |
| 11 | NIV_PS spike_pH7_22° C. | 7 | | | | 50 |
| 12 | NIV_Ni(II)_100_PSspike_pH7_22° C. | 7 | 100 | | | 50 |
| 13 | NIV_Ni(II)_500_PSspike_pH7_22° C. | 7 | 500 | | | 50 |
| 14 | NIV_Ni(II)_1000_PSspike_pH7_22° C. | 7 | 1000 | | | 50 |
| 15 | NIV_Cu(II)_100_PSspike_pH7_22° C. | 7 | | 100 | | 50 |
| 16 | NIV_Cu(II)_500_PSspike_pH7_22° C. | 7 | | 500 | | 50 |
| 17 | NIV_Cu(II)_1000_PSspike_pH7_22° C. | 7 | | 1000 | | 50 |
| 18 | NIV_CR(III)_100_PSspike_pH7_22° C. | 7 | | | 100 | 50 |
| 19 | NIV_CR(III)_500_PSspike_pH7_22° C. | 7 | | | 500 | 50 |
| 20 | NIV_CR(III)_1000_PSspike_pH7_22° C. | 7 | | | 1000 | 50 |
| 21 | NIV_unspiked_pH8_22° C. | 8 | | | | |
| 22 | NIV_Ni(II)_100_pH8_22° C. | 8 | 100 | | | |
| 23 | NIV_Ni(II)_500_pH8_22° C. | 8 | 500 | | | |
| 24 | NIV_Ni(II)_1000_pH8_22° C. | 8 | 1000 | | | |
| 25 | NIV_Cu(II)_100_pH8_22° C. | 8 | | 100 | | |
| 26 | NIV_Cu(II)_500_pH8_22° C. | 8 | | 500 | | |
| 27 | NIV_Cu(II)_1000_pH8_22° C. | 8 | | 1000 | | |
| 28 | NIV_CR(III)_100_pH8_22° C. | 8 | | | 100 | |

TABLE 9-continued

Plan for experiment 20110913(NIV)

| | | | | | | |
|---|---|---|---|---|---|---|
| 29 | NIV_CR(III)_500_pH8_22° C. | 8 | | | 500 | |
| 30 | NIV_CR(III)_1000_pH8_22° C. | 8 | | | 1000 | |
| 31 | NIV_PS spike_pH8_22° C. | 8 | | | | 50 |
| 32 | NIV_Ni(II)_100_PSspike_pH8_22° C. | 8 | 100 | | | 50 |
| 33 | NIV_Ni(II)_500_PSspike_pH8_22° C. | 8 | 500 | | | 50 |
| 34 | NIV_Ni(II)_1000_PSspike_pH8_22° C. | 8 | 1000 | | | 50 |
| 35 | NIV_Cu(II)_100_PSspike_pH8_22° C. | 8 | | 100 | | 50 |
| 36 | NIV_Cu(II)_500_PSspike_pH8_22° C. | 8 | | 500 | | 50 |
| 37 | NIV_Cu(II)_1000_PSspike_pH8_22° C. | 8 | | 1000 | | 50 |
| 38 | NIV_CR(III)_100_PSspike_pH8_22° C. | 8 | | | 100 | 50 |
| 39 | NIV_CR(III)_500_PSspike_pH8_22° C. | 8 | | | 500 | 50 |
| 40 | NIV_CR(III)_1000_PSspike_pH8_22° C. | 8 | | | 1000 | 50 |

| | MW [g/Mol] | other additives: | |
|---|---|---|---|
| Ni | 58.7 | Stock Sol: | |
| Cu | 63.6 | frag PS | 2 mg/mL |
| Cr | 52.0 | | |

| Sample | | | Volume [µl] | | | | | | |
|---|---|---|---|---|---|---|---|---|---|
| | | | | | | | | fragmented | |
| No. | Name | pH | NIV | PBS | Ni(II)SO4 | Cu(II)Cl2 | Cr(III) | PS | Total |
| 1 | NIV_unspiked_pH7_22° C. | 7 | 1800 | 200 | 0 | 0 | 0 | 0 | 2000 |
| 2 | NIV_Ni(II)_100_pH7_22° C. | 7 | 1800 | 197 | 3 | 0 | 0 | 0 | 2000 |
| 3 | NIV_Ni(II)_500_pH7_22° C. | 7 | 1800 | 183 | 17 | 0 | 0 | 0 | 2000 |
| 4 | NIV_Ni(II)_1000_pH7_22° C. | 7 | 1800 | 166 | 34 | 0 | 0 | 0 | 2000 |
| 5 | NIV_Cu(II)_100_pH7_22° C. | 7 | 1800 | 197 | 0 | 3 | 0 | 0 | 2000 |
| 6 | NIV_Cu(II)_500_pH7_22° C. | 7 | 1800 | 184 | 0 | 16 | 0 | 0 | 2000 |
| 7 | NIV_Cu(II)_1000_pH7_22° C. | 7 | 1800 | 169 | 0 | 31 | 0 | 0 | 2000 |
| 8 | NIV_CR(III)_100_pH7_22° C. | 7 | 1800 | 196 | 0 | 0 | 4 | 0 | 2000 |
| 9 | NIV_CR(III)_500_pH7_22° C. | 7 | 1800 | 181 | 0 | 0 | 19 | 0 | 2000 |
| 10 | NIV_CR(III)_1000_pH7_22° C. | 7 | 1800 | 162 | 0 | 0 | 38 | 0 | 2000 |
| 11 | NIV_PS spike_pH7_22° C. | 7 | 1800 | 150 | 0 | 0 | 0 | 50 | 2000 |
| 12 | NIV_Ni(II)_100_PSspike_pH7_22° C. | 7 | 1800 | 147 | 3 | 0 | 0 | 50 | 2000 |
| 13 | NIV_Ni(II)_500_PSspike_pH7_22° C. | 7 | 1800 | 133 | 17 | 0 | 0 | 50 | 2000 |
| 14 | NIV_Ni(II)_1000_PSspike_pH7_22° C. | 7 | 1800 | 116 | 34 | 0 | 0 | 50 | 2000 |
| 15 | NIV_Cu(II)_100_PSspike_pH7_22° C. | 7 | 1800 | 147 | 0 | 3 | 0 | 50 | 2000 |
| 16 | NIV_Cu(II)_500_PSspike_pH7_22° C. | 7 | 1800 | 134 | 0 | 16 | 0 | 50 | 2000 |
| 17 | NIV_Cu(II)_1000_PSspike_pH7_22° C. | 7 | 1800 | 119 | 0 | 31 | 0 | 50 | 2000 |
| 18 | NIV_CR(III)_100_PSspike_pH7_22° C. | 7 | 1800 | 146 | 0 | 0 | 4 | 50 | 2000 |
| 19 | NIV_CR(III)_500_PSspike_pH7_22° C. | 7 | 1800 | 131 | 0 | 0 | 19 | 50 | 2000 |
| 20 | NIV_CR(III)_1000_PSspike_pH7_22° C. | 7 | 1800 | 112 | 0 | 0 | 38 | 50 | 2000 |
| 21 | NIV_unspiked_pH8_22° C. | 8 | 1800 | 200 | 0 | 0 | 0 | 0 | 2000 |
| 22 | NIV_Ni(II)_100_pH8_22° C. | 8 | 1800 | 197 | 3 | 0 | 0 | 0 | 2000 |
| 23 | NIV_Ni(II)_500_pH8_22° C. | 8 | 1800 | 183 | 17 | 0 | 0 | 0 | 2000 |
| 24 | NIV_Ni(II)_1000_pH8_22° C. | 8 | 1800 | 166 | 34 | 0 | 0 | 0 | 2000 |
| 25 | NIV_Cu(II)_100_pH8_22° C. | 8 | 1800 | 197 | 0 | 3 | 0 | 0 | 2000 |
| 26 | NIV_Cu(II)_500_pH8_22° C. | 8 | 1800 | 184 | 0 | 16 | 0 | 0 | 2000 |
| 27 | NIV_Cu(II)_1000_pH8_22° C. | 8 | 1800 | 169 | 0 | 31 | 0 | 0 | 2000 |
| 28 | NIV_CR(III)_100_pH8_22° C. | 8 | 1800 | 196 | 0 | 0 | 4 | 0 | 2000 |
| 29 | NIV_CR(III)_500_pH8_22° C. | 8 | 1800 | 181 | 0 | 0 | 19 | 0 | 2000 |
| 30 | NIV_CR(III)_1000_pH8_22° C. | 8 | 1800 | 162 | 0 | 0 | 38 | 0 | 2000 |
| 31 | NIV_PS spike_pH8_22° C. | 8 | 1800 | 150 | 0 | 0 | 0 | 50 | 2000 |
| 32 | NIV_Ni(II)_100_PSspike_pH8_22° C. | 8 | 1800 | 147 | 3 | 0 | 0 | 50 | 2000 |
| 33 | NIV_Ni(II)_500_PSspike_pH8_22° C. | 8 | 1800 | 133 | 17 | 0 | 0 | 50 | 2000 |
| 34 | NIV_Ni(II)_1000_PSspike_pH8_22° C. | 8 | 1800 | 116 | 34 | 0 | 0 | 50 | 2000 |
| 35 | NIV_Cu(II)_100_PSspike_pH8_22° C. | 8 | 1800 | 147 | 0 | 3 | 0 | 50 | 2000 |
| 36 | NIV_Cu(II)_500_PSspike_pH8_22° C. | 8 | 1800 | 134 | 0 | 16 | 0 | 50 | 2000 |
| 37 | NIV_Cu(II)_1000_PSspike_pH8_22° C. | 8 | 1800 | 119 | 0 | 31 | 0 | 50 | 2000 |
| 38 | NIV_CR(III)_100_PSspike_pH8_22° C. | 8 | 1800 | 146 | 0 | 0 | 4 | 50 | 2000 |
| 39 | NIV_CR(III)_500_PSspike_pH8_22° C. | 8 | 1800 | 131 | 0 | 0 | 19 | 50 | 2000 |
| 40 | NIV_CR(III)_1000_PSspike_pH8_22° C. | 8 | 1800 | 112 | 0 | 0 | 38 | 50 | 2000 |

TABLE 10

Plan for experiment 20110913(DP)

Pipetting plan

| | | | |
|---|---|---|---|
| | | Stock Sol [mM] | |
| Total Volume: | 10000 µl | Ni(II)SO4 | 1 |
| | | Cu(II)Cl2 | 1 |
| DP: | 11D87 bulk | Cr(III)Cl3 | 1 |

| Sample | | | µg/L | | | |
|---|---|---|---|---|---|---|
| No. | Name | pH | Ni(II)SO4 | Cu(II)Cl2 | Cr(III) | fragmented PS |
| 1 | DP_unspiked_pH7 | 7 | | | | |
| 2 | DP_Ni(II)_100_pH7 | 7 | 100 | | | |
| 3 | DP_Ni(II)_500_pH7 | 7 | 500 | | | |
| 4 | DP_Ni(II)_1000_pH7 | 7 | 1000 | | | |
| 5 | DP_Cu(II)_100_pH7 | 7 | | 100 | | |
| 6 | DP_Cu(II)_500_pH7 | 7 | | 500 | | |
| 7 | DP_Cu(II)_1000_pH7 | 7 | | 1000 | | |
| 8 | DP_Cr(III)_100_pH7 | 7 | | | 100 | |
| 9 | DP_Cr(III)_500_pH7 | 7 | | | 500 | |
| 10 | DP_Cr(III)_1000_pH7 | 7 | | | 1000 | |
| 11 | DP_unspiked_pH8 | 8 | | | | |
| 12 | DP_Ni(II)_100_pH8 | 8 | 100 | | | |
| 13 | DP_Ni(II)_500_pH8 | 8 | 500 | | | |
| 14 | DP_Ni(II)_1000_pH8 | 8 | 1000 | | | |
| 15 | DP_Cu(II)_100_pH8 | 8 | | 100 | | |
| 16 | DP_Cu(II)_500_pH8 | 8 | | 500 | | |
| 17 | DP_Cu(II)_1000_pH8 | 8 | | 1000 | | |
| 18 | DP_Cr(III)_100_pH8 | 8 | | | 100 | |
| 19 | DP_Cr(III)_500_pH8 | 8 | | | 500 | |
| 20 | DP_Cr(III)_1000_pH8 | 8 | | | 1000 | |

| MW [g/Mol] | | other additives: | |
|---|---|---|---|
| Ni | 58.7 | Stock Sol: | |
| Cu | 63.6 | frag PS | 2 mg/mL |
| Cr | 52.0 | | |

| Sample | | | Volume [µl] | | | | | | |
|---|---|---|---|---|---|---|---|---|---|
| No. | Name | pH | DP | Buffer | Ni(II)SO4 | Cu(II)Cl2 | Cr(III) | fragmented PS | Total |
| 1 | DP_unspiked_pH7 | 7 | 9500 | 500 | 0 | 0 | 0 | 0 | 10000 |
| 2 | DP_Ni(II)_100_pH7 | 7 | 9500 | 483 | 17 | 0 | 0 | 0 | 10000 |
| 3 | DP_Ni(II)_500_pH7 | 7 | 9500 | 415 | 85 | 0 | 0 | 0 | 10000 |
| 4 | DP_Ni(II)_1000_pH7 | 7 | 9500 | 330 | 170 | 0 | 0 | 0 | 10000 |
| 5 | DP_Cu(II)_100_pH7 | 7 | 9500 | 484 | 0 | 16 | 0 | 0 | 10000 |
| 6 | DP_Cu(II)_500_pH7 | 7 | 9500 | 421 | 0 | 79 | 0 | 0 | 10000 |
| 7 | DP_Cu(II)_1000_pH7 | 7 | 9500 | 343 | 0 | 157 | 0 | 0 | 10000 |
| 8 | DP_Cr(III)_100_pH7 | 7 | 9500 | 481 | 0 | 0 | 19 | 0 | 10000 |
| 9 | DP_Cr(III)_500_pH7 | 7 | 9500 | 404 | 0 | 0 | 96 | 0 | 10000 |
| 10 | DP_Cr(III)_1000_pH7 | 7 | 9500 | 308 | 0 | 0 | 192 | 0 | 10000 |
| 11 | DP_unspiked_pH8 | 8 | 9500 | 500 | 0 | 0 | 0 | 0 | 10000 |
| 12 | DP_Ni(II)_100_pH8 | 8 | 9500 | 483 | 17 | 0 | 0 | 0 | 10000 |
| 13 | DP_Ni(II)_500_pH8 | 8 | 9500 | 415 | 85 | 0 | 0 | 0 | 10000 |
| 14 | DP_Ni(II)_1000_pH8 | 8 | 9500 | 330 | 170 | 0 | 0 | 0 | 10000 |
| 15 | DP_Cu(II)_100_pH8 | 8 | 9500 | 484 | 0 | 16 | 0 | 0 | 10000 |
| 16 | DP_Cu(II)_500_pH8 | 8 | 9500 | 421 | 0 | 79 | 0 | 0 | 10000 |
| 17 | DP_Cu(II)_1000_pH8 | 8 | 9500 | 343 | 0 | 157 | 0 | 0 | 10000 |
| 18 | DP_Cr(III)_100_pH8 | 8 | 9500 | 481 | 0 | 0 | 19 | 0 | 10000 |
| 19 | DP_Cr(III)_500_pH8 | 8 | 9500 | 404 | 0 | 0 | 96 | 0 | 10000 |
| 20 | DP_Cr(III)_1000_pH8 | 8 | 9500 | 308 | 0 | 0 | 192 | 0 | 10000 |

TABLE 11

Plan for experiment 20110812-Metal Ion Spiked DP

Pipetting plan

| | | Stock Sol [mM] | | MW [g/Mol] | | FVL ng/mL | µM |
|---|---|---|---|---|---|---|---|
| Total Volume: | 30000 µl | Fe(II)Cl3 | 1 | Fe | 55.9 | 282 | 5.049 |
| DP: | 11D87 bulk | Fe(III)Cl3 | 1 | Fe | 55.9 | 282 | 5.045 |
| | | Ni(II)SO4 | 1 | Ni | 58.7 | 41 | 0.698 |

TABLE 11-continued

Plan for experiment 20110812-Metal Ion Spiked DP

| | | | | | |
|---|---|---|---|---|---|
| Co(II)Cl2 | 1 | Co | 58.9 | 0.33 | 0.006 |
| Cu(II)Cl2 | 1 | Cu | 63.6 | 3 | 0.047 |
| Zn(II)SO4 | 1 | Zn | 65.4 | | |
| Cr(III)Cl3 | 1 | Cr | 52.0 | | |

| Sample | | | µg/L | | | | | | |
|---|---|---|---|---|---|---|---|---|---|
| No. | Name | pH | DP dil | Fe(II)Cl3 | Fe(III)Cl3 | Ni(II)SO4 | Co(II)Cl2 | Cu(II)Cl2 | Zn(II)SO4 |
| 1 | DP_Fe(II)_pH7 | 7 | 1 | 500 | | | | | |
| 2 | DP_Fe(III)_pH7 | 7 | 1 | | 500 | | | | |
| 3 | DP_Ni(II)_pH7 | 7 | 1 | | | 500 | | | |
| 4 | DP_Co(II)_pH7 | 7 | 1 | | | | 500 | | |
| 5 | DP_Cu(II)_pH7 | 7 | 1 | | | | | 500 | |
| 6 | DP_Zn_pH7 | 7 | 1 | | | | | | 500 |
| 7 | DP_metalmix_pH7 | 7 | 1 | 500 | 500 | 500 | 500 | 500 | 500 |
| 8 | DP_unspiked_pH7 | 7 | 1 | | | | | | |
| 9 | DP_Fe(II)_pH7.4 | 7.4 | 1 | 500 | | | | | |
| 10 | DP_Fe(III)_pH7.4 | 7.4 | 1 | | 500 | | | | |
| 11 | DP_Ni(II)_pH7.4 | 7.4 | 1 | | | 500 | | | |
| 12 | DP_Co(II)_pH7.4 | 7.4 | 1 | | | | 500 | | |
| 13 | DP_Cu(II)_pH7.4 | 7.4 | 1 | | | | | 500 | |
| 14 | DP_Zn_pH7.4 | 7.4 | 1 | | | | | | 500 |
| 15 | DP_metalmix_pH7.4 | 7.4 | 1 | 500 | 500 | 500 | 500 | 500 | 500 |
| 16 | DP_unspiked_pH7.4 | 7.4 | 1 | | | | | | |
| 17 | DP_Fe(II)_pH7.8 | 7.8 | 1 | 500 | | | | | |
| 18 | DP_Fe(III)_pH7.8 | 7.8 | 1 | | 500 | | | | |
| 19 | DP_Ni(II)_pH7.8 | 7.8 | 1 | | | 500 | | | |
| 20 | DP_Co(II)_pH7.8 | 7.8 | 1 | | | | 500 | | |
| 21 | DP_Cu(II)_pH7.8 | 7.8 | 1 | | | | | 500 | |
| 22 | DP_Zn_pH7.8 | 7.8 | 1 | | | | | | 500 |
| 23 | DP_metalmix_pH7.8 | 7.8 | 1 | 500 | 500 | 500 | 500 | 500 | 500 |
| 24 | DP_unspiked_pH7.8 | 7.8 | 1 | | | | | | |

| Sample | | | µg/L | |
|---|---|---|---|---|
| No. | Name | pH | DP dil | Cr(III) |
| 25 | DP_CR(III)_pH7 | 7 | 1 | 500 |
| 26 | DP_Cr(III)_pH7.4 | 7.4 | 1 | 500 |
| 27 | DP_Cr(III)_pH7.8 | 7.8 | 1 | 500 |

| Sample | | | Volume [µl] | | | | | | | | |
|---|---|---|---|---|---|---|---|---|---|---|---|
| No. | Name | pH | NIV dil | Buffer | Fe(II)Cl3 | Fe(III)Cl3 | Ni(II)SO4 | Co(II)Cl2 | Cu(II)Cl2 | Zn(II)SO4 | Total |
| 1 | DP_Fe(II)_pH7 | 7 | 27750 | 1981 | 269 | 0 | 0 | 0 | 0 | 0 | 30000 |
| 2 | DP_Fe(III)_pH7 | 7 | 27750 | 1982 | 0 | 268 | 0 | 0 | 0 | 0 | 30000 |
| 3 | DP_Ni(II)_pH7 | 7 | 27750 | 1981 | 0 | 0 | 269 | 0 | 0 | 0 | 30000 |
| 4 | DP_Co(II)_pH7 | 7 | 27750 | 1994 | 0 | 0 | 0 | 256 | 0 | 0 | 30000 |
| 5 | DP_Cu(II)_pH7 | 7 | 27750 | 1995 | 0 | 0 | 0 | 0 | 255 | 0 | 30000 |
| 6 | DP_Zn_pH7 | 7 | 27750 | 2014 | 0 | 0 | 0 | 0 | 0 | 236 | 30000 |
| 7 | DP_metalmix_pH7 | 7 | 27750 | 698 | 269 | 268 | 269 | 256 | 255 | 236 | 30000 |
| 8 | DP_unspiked_pH7 | 7 | 27750 | 2250 | 0 | 0 | 0 | 0 | 0 | 0 | 30000 |
| 9 | DP_Fe(II)_pH7.4 | 7.4 | 27750 | 1981 | 269 | 0 | 0 | 0 | 0 | 0 | 30000 |
| 10 | DP_Fe(III)_pH7.4 | 7.4 | 27750 | 1982 | 0 | 268 | 0 | 0 | 0 | 0 | 30000 |
| 11 | DP_Ni(II)_pH7.4 | 7.4 | 27750 | 1981 | 0 | 0 | 269 | 0 | 0 | 0 | 30000 |
| 12 | DP_Co(II)_pH7.4 | 7.4 | 27750 | 1994 | 0 | 0 | 0 | 256 | 0 | 0 | 30000 |
| 13 | DP_Cu(II)_pH7.4 | 7.4 | 27750 | 1995 | 0 | 0 | 0 | 0 | 255 | 0 | 30000 |
| 14 | DP_Zn_pH7.4 | 7.4 | 27750 | 2014 | 0 | 0 | 0 | 0 | 0 | 236 | 30000 |
| 15 | DP_metalmix_pH7.4 | 7.4 | 27750 | 698 | 269 | 268 | 269 | 256 | 255 | 236 | 30000 |
| 16 | DP_unspiked_pH7.4 | 7.4 | 27750 | 2250 | 0 | 0 | 0 | 0 | 0 | 0 | 30000 |
| 17 | DP_Fe(II)_pH7.8 | 7.8 | 27750 | 1981 | 269 | 0 | 0 | 0 | 0 | 0 | 30000 |
| 18 | DP_Fe(III)_pH7.8 | 7.8 | 27750 | 1982 | 0 | 268 | 0 | 0 | 0 | 0 | 30000 |
| 19 | DP_Ni(II)_pH7.8 | 7.8 | 27750 | 1981 | 0 | 0 | 269 | 0 | 0 | 0 | 30000 |
| 20 | DP_Co(II)_pH7.8 | 7.8 | 27750 | 1994 | 0 | 0 | 0 | 256 | 0 | 0 | 30000 |
| 21 | DP_Cu(II)_pH7.8 | 7.8 | 27750 | 1995 | 0 | 0 | 0 | 0 | 255 | 0 | 30000 |
| 22 | DP_Zn_pH7.8 | 7.8 | 27750 | 2014 | 0 | 0 | 0 | 0 | 0 | 236 | 30000 |
| 23 | DP_metalmix_pH7.8 | 7.8 | 27750 | 698 | 269 | 268 | 269 | 256 | 255 | 236 | 30000 |
| 24 | DP_unspiked_pH7.8 | 7.8 | 27750 | 2250 | 0 | 0 | 0 | 0 | 0 | 0 | 30000 |

TABLE 11-continued

| Plan for experiment 20110812-Metal Ion Spiked DP | | | |
|---|---|---|---|
| Sample | | | Volume [μl] |
| No. | Name | pH | Cr(III)Cl3 |
| 8 | DP_CR(III)_pH7 | 7 | 48 |
| 16 | DP_Cr(III)_pH7.4 | 7.4 | 48 |
| 24 | DP_Cr(III)_pH7.8 | 7.8 | 48 |

TABLE 12

Antigen recovery determined by SEC-HPLC of exp. 20110913(NIV). For pH 7 and pH 8 the recoveries are based on non-spiked NIV control samples #1 and #21, respectively. Samples were stored at 22° C. for 3 weeks. Samples marked with "n.a" were not analyzed due to sample prioritization

| | Results | |
|---|---|---|
| Sample | Area mAU*s | Recovery (%) |
| 1 NIV_unspiked_pH 7_22° C. | 4.054 | 100.0 |
| 2 NIV_Ni(II)_100_pH 7_22° C. | 3.972 | 98.0 |
| 3 NIV_Ni(II)_500_pH 7_22° C. | 4.454 | 109.9 |
| 4 NIV_Ni(II)_1000_pH 7_22° C. | 4.185 | 103.2 |
| 5 NIV_Cu(II)_100_pH 7_22° C. | 3.913 | 96.5 |
| 6 NIV_Cu(II)_500_pH 7_22° C. | 3.733 | 92.1 |
| 7 NIV_Cu(II)_1000_pH 7_22° C. | 3.115 | 76.8 |
| 8 NIV_CR(III)_100_pH 7_22° C. | 3.957 | 97.6 |
| 9 NIV_CR(III)_500_pH 7_22° C. | 4.000 | 98.7 |
| 10 NIV_CR(III)_1000_pH 7_22° C. | 3.611 | 89.1 |
| 11 NIV_PS spike_pH 7_22° C. | 4.068 | 100.3 |
| 12 NIV_Ni(II)_100_PSspike_pH 7_22° C. | 3.884 | 95.8 |
| 13 NIV_Ni(II)_500_PSspike_pH 7_22° C. | 3.688 | 91.0 |
| 14 NIV_Ni(II)_1000_PSspike_pH 7_22° C. | 3.971 | 98.0 |
| 15 NIV_Cu(II)_100_PSspike_pH 7_22° C. | 3.568 | 88.0 |
| 16 NIV_Cu(II)_500_PSspike_pH 7_22° C. | 3.325 | 82.0 |
| 17 NIV_Cu(II)_1000_PSspike_pH 7_22° C. | 3.486 | 86.0 |
| 18 NIV_CR(III)_100_PSspike_pH 7_22° C. | 3.747 | 92.4 |
| 19 NIV_CR(III)_500_PSspike_pH 7_22° C. | 3.904 | 96.3 |
| 20 NIV_CR(III)_1000_PSspike_pH 7_22° C. | 3.685 | 90.9 |

TABLE 12-continued

Antigen recovery determined by SEC-HPLC of exp. 20110913(NIV). For pH 7 and pH 8 the recoveries are based on non-spiked NIV control samples #1 and #21, respectively. Samples were stored at 22° C. for 3 weeks. Samples marked with "n.a" were not analyzed due to sample prioritization

| | Results | |
|---|---|---|
| Sample | Area mAU*s | Recovery (%) |
| 21 NIV_unspiked_pH 8_22° C. | 4.213 | 100.0 |
| 22 NIV_Ni(II)_100_pH 8_22° C. | 4.181 | 99.2 |
| 23 NIV_Ni(II)_500_pH 8_22° C. | 4.150 | 98.5 |
| 24 NIV_Ni(II)_1000_pH 8_22° C. | 3.772 | 89.5 |
| 25 NIV_Cu(II)_100_pH 8_22° C. | 4.146 | 98.4 |
| 26 NIV_Cu(II)_500_pH 8_22° C. | 4.212 | 100.0 |
| 27 NIV_Cu(II)_1000_pH 8_22° C. | 4.152 | 98.6 |
| 28 NIV_CR(III)_100_pH 8_22° C. | 4.213 | 100.0 |
| 29 NIV_CR(III)_500_pH 8_22° C. | 3.997 | 94.9 |
| 30 NIV_CR(III)_1000_pH 8_22° C. | 4.231 | 100.4 |
| 31 NIV_PS spike_pH 8_22° C. | 4.150 | 98.5 |
| 32 NIV_Ni(II)_100_PSspike_pH 8_22° C. | 3.623 | 86.0 |
| 33 NIV_Ni(II)_500_PSspike_pH 8_22° C. | 3.725 | 88.4 |
| 34 NIV_Ni(II)_1000_PSspike_pH 8_22° C. | 4.079 | 96.8 |
| 35 NIV_Cu(II)_100_PSspike_pH 8_22° C. | 3.473 | 82.4 |
| 36 NIV_Cu(II)_500_PSspike_pH 8_22° C. | 3.180 | 75.5 |
| 37 NIV_Cu(II)_1000_PSspike_pH 8_22° C. | 4.056 | 96.3 |
| 38 NIV_CR(III)_100_PSspike_pH 8_22° C. | 3.042 | 72.2 |
| 39 NIV_CR(III)_500_PSspike_pH 8_22° C. | 4.113 | 97.6 |
| 40 NIV_CR(III)_1000_PSspike_pH 8_22° C. | n.a. | n.a. |

TABLE 13

ELISA results of exp. 20110913(NIV) obtained after 3 weeks at pH 8 (sample 21-40) and 7 weeks at pH 7(sample 1-20) at 22° C. Samples marked with "n.a" were not analyzed due to sample prioritization.

| 20110913_metal spiked_NIV_22° C. 7 weeks at pH 7 | | | | |
|---|---|---|---|---|
| No. | Name | poly | mono | ratio |
| 1 | NIV_unspiked_pH7_22° C. CONTROL | 20.699 | 17.512 | 0.846 |
| 2 | NIV_Ni(II)_100_pH7_22° C. | 17.243 | 14.787 | 0.858 |
| 3 | NIV_Ni(II)_500_pH7_22° C. | 18.877 | 16.215 | 0.859 |
| 4 | NIV_Ni(II)_1000_pH7_22° C. | 16.9 | 14.522 | 0.859 |
| 5 | NIV_Cu(II)_100_pH7_22° C. | 16.718 | 13.278 | 0.794 |
| 6 | NIV_Cu(II)_500_pH7_22° C. | 14.664 | 5.459 | 0.372 |
| 7 | NIV_Cu(II)_1000_pH7_22° C. | 7.112 | 0.421 | 0.059 |
| 8 | NIV_CR(III)_100_pH7_22° C. | 19.207 | 16.602 | 0.864 |
| 9 | NIV_CR(III)_500_pH7_22° C. | 20.313 | 17.84 | 0.878 |
| 10 | NIV_CR(III)_1000_pH7_22° C. | 16.762 | 13.128 | 0.783 |
| 11 | NIV_PS spike_pH7_22° C. CONTROL | 19.907 | 16.994 | 0.854 |
| 12 | NIV_Ni(II)_100_PSspike_pH7_22° C. | 19.546 | 16.534 | 0.846 |
| 13 | NIV_Ni(II)_500_PSspike_pH7_22° C. | 18.337 | 15.2 | 0.829 |
| 14 | NIV_Ni(II)_1000_PSspike_pH7_22° C. | 20.759 | 16.934 | 0.816 |
| 15 | NIV_Cu(II)_100_PSsPike_pH7_22° C. | 18.249 | 13.348 | 0.731 |
| 16 | NIV_Cu(II)_500_PSspike_pH7_22° C. | 19.201 | 7.733 | 0.403 |
| 17 | NIV_Cu(II)_1000_PSspike_pH7_22° C. | 8.515 | 0.711 | 0.083 |

TABLE 13-continued

ELISA results of exp. 20110913(NIV) obtained after 3 weeks at pH 8 (sample 21-40) and 7 weeks at pH 7(sample 1-20) at 22° C. Samples marked with "n.a" were not analyzed due to sample prioritization.

| | | | | |
|---|---|---|---|---|
| 18 | NIV_CR(III)_100_PSspike_pH7_22° C. | 18.377 | 16.521 | 0.899 |
| 19 | NIV_CR(III)_500_PSspike_pH7_22° C. | 19.678 | 17.119 | 0.870 |
| 20 | NIV_CR(III)_1000_PSspike_pH7_22° C. | 20.505 | 18.219 | 0.889 |

20110913_metal spiked_NIV_22° C. 3 weeks at pH 8

| | | 1st analysis | | | 2nd analysis | | |
|---|---|---|---|---|---|---|---|
| No | | poly | mono | ratio | poly | mono | ratio |
| 21 | NIV_unspiked_pH8_22° C. CONTROL | 22.729 | 20.679 | 0.910 | 24.687 | 24.806 | 1.005 |
| 22 | NIV_Ni(II)_100_pH8_22° C. | 23.732 | 23.572 | 0.993 | 24.179 | 22.148 | 0.916 |
| 23 | NIV_Ni(II)_500_pH8_22° C. | 20.086 | 19.793 | 0.985 | 22.411 | 22.207 | 0.991 |
| 24 | NIV_Ni(II)_1000_pH8_22° C. | 16.553 | 15.402 | 0.930 | 23.841 | 21.645 | 0.908 |
| 25 | NIV_Cu(II)_100_pH8_22° C. | 18.736 | 18.175 | 0.970 | 28.024 | 24.714 | 0.882 |
| 26 | NIV_Cu(II)_500_pH8_22° C. | 21.173 | 19.109 | 0.903 | 25.774 | 23.983 | 0.931 |
| 27 | NIV_Cu(II)_1000_pH8_22° C. | 19.709 | 16.406 | 0.832 | 24.799 | 21.580 | 0.870 |
| 28 | NIV_CR(III)_100_pH8_22° C. | 22.464 | 20.687 | 0.921 | 22.782 | 21.156 | 0.929 |
| 29 | NIV_CR(III)_500_pH8_22° C. | 20.527 | 20.247 | 0.986 | 23.040 | 21.649 | 0.940 |
| 30 | NIV_CR(III)_1000_pH8_22° C. | 20.838 | 19.094 | 0.916 | 25.676 | 24.047 | 0.937 |
| 31 | NIV_PS spike_pH8_22° C. CONTROL | 19.051 | 20.112 | 1.056 | 25.413 | 25.991 | 1.023 |
| 32 | NIV_Ni(II)_100_PSspike_pH8_22° C. | 18.729 | 19.250 | 1.028 | n.a. | n.a. | n.a. |
| 33 | NIV_Ni(II)_500_PSspike_pH8_22° C. | 20.923 | 20.516 | 0.981 | n.a. | n.a. | n.a. |
| 34 | NIV_Ni(II)_1000_PSspike_pH8_22° C. | 21.734 | 19.794 | 0.911 | 25.164 | 24.899 | 0.989 |
| 35 | NIV_Cu(II)_100_PSspike_pH8_22° C. | 21.526 | 19.852 | 0.922 | n.a. | n.a. | n.a. |
| 36 | NIV_Cu(II)_500_PSspike_pH8_22° C. | 21.914 | 19.449 | 0.888 | n.a. | n.a. | n.a. |
| 37 | NIV_Cu(II)_1000_PSspike_pH8_22° C. | 18.646 | 16.259 | 0.872 | 25.371 | 24.275 | 0.957 |
| 38 | NIV_CR(III)_100_PSspike_pH8_22° C. | 20.292 | 18.667 | 0.920 | n.a. | n.a. | n.a. |
| 39 | NIV_CR(III)_500_PSspike_pH8_22° C. | 22.835 | 21.558 | 0.944 | 25.561 | 24.480 | 0.958 |
| 40 | NIV_CR(III)_1000_PSspike_pH8_22° C. | 27.862 | 25.291 | 0.908 | n.a. | n.a. | n.a. |

TABLE 14

Antigen recoveries after 5 weeks at 22° C. of desorbed JEV obtained by SEC-HPLC. Recoveries were based on non-spiked DP control samples stored at either pH 7 or pH 8

| No | Sample | JEV area mAU · min | recovery |
|---|---|---|---|
| 1 | DP_unspiked_pH 7 22° C. | 3.710 | 100% |
| 2 | DP_Ni(II)_100_pH 7 22° C. | 3.656 | 99% |
| 3 | DP_Ni(II)_500_pH 7 22° C. | 3.705 | 100% |
| 4 | DP_Ni(II)_1000_pH 7 22° C. | 3.444 | 93% |
| 5 | DP_Cu(II)_100_pH 7 22° C. | 3.565 | 96% |
| 6 | DP_Cu(II)_500_pH 7 22° C. | 3.313 | 89% |
| 7 | DP_Cu(II)_1000_pH 7 22° C. | 3.367 | 91% |
| 8 | DP_Cr(III)_100_pH 7 22° C. | 3.562 | 96% |
| 9 | DP_Cr(III)_500_pH 7 22° C. | 3.422 | 92% |
| 10 | DP_Cr(III)_1000_pH 7 22° C. | 3.148 | 85% |
| 11 | DP_unspiked_pH 8 22° C. | 4.297 | 100% |
| 12 | DP_Ni(II)_100_pH 8 22° C. | 4.029 | 94% |
| 13 | DP_Ni(II)_500_pH 8 22° C. | 4.306 | 100% |
| 14 | DP_Ni(II)_1000_pH 8 22° C. | 4.065 | 95% |
| 15 | DP_Cu(II)_100_pH 8 22° C. | 3.751 | 87% |
| 16 | DP_Cu(II)_500_pH 8 22° C. | 3.698 | 86% |
| 17 | DP_Cu(II)_1000_pH 8 22° C. | 3.511 | 82% |
| 18 | DP_Cr(III)_100_pH 8 22° C. | 3.805 | 89% |
| 19 | DP_Cr(III)_500_pH 8 22° C. | 3.843 | 89% |
| 20 | DP_Cr(III)_1000_pH 8 22° C. | 4.212 | 98% |

TABLE 15

ELISA results of desorbed JEV antigen after 5 weeks at 22° C.

| No. | Name | pH | Poly. ELISA | Mono. ELISA | Ratio | % Ratio compared to non-spiked Control |
|---|---|---|---|---|---|---|
| 1 | DP_unspiked_pH7 | 7 | 14.203 | 13.13 | 0.924 | 100 |
| 2 | DP_Ni(II)_100_pH7 | 7 | 13.089 | 12.623 | 0.964 | 104 |
| 3 | DP_Ni(II)_500_pH7 | 7 | 12.640 | 12.572 | 0.995 | 108 |
| 4 | DP_Ni(II)_1000_pH7 | 7 | 15.051 | 11.757 | 0.781 | 84 |
| 5 | DP_Cu(II)_100_pH7 | 7 | 13.420 | 10.792 | 0.804 | 87 |
| 6 | DP_Cu(II)_500_pH7 | 7 | 13.247 | 10.079 | 0.761 | 82 |
| 7 | DP_Cu(II)_1000_pH7 | 7 | 12.981 | 9.654 | 0.744 | 80 |
| 8 | DP_Cr(III)_100_pH7 | 7 | 16.936 | 11.886 | 0.702 | 76 |
| 9 | DP_Cr(III)_500_pH7 | 7 | 13.991 | 11.219 | 0.802 | 87 |
| 10 | DP_Cr(III)_1000_pH7 | 7 | 13.061 | 10.438 | 0.799 | 86 |
| 11 | DP_unspiked_pH8 | 8 | 12.647 | 11.287 | 0.892 | 100 |
| 12 | DP_Ni(II)_100_pH8 | 8 | 12.308 | 10.689 | 0.868 | 97 |
| 13 | DP_Ni(II)_500_pH8 | 8 | 14.300 | 12.623 | 0.883 | 99 |
| 14 | DP_Ni(II)_1000_pH8 | 8 | 12.082 | 10.930 | 0.905 | 101 |
| 15 | DP_Cu(II)_100_pH8 | 8 | 11.041 | 9.937 | 0.900 | 101 |
| 16 | DP_Cu(II)_500_pH8 | 8 | 9.869 | 9.176 | 0.930 | 104 |
| 17 | DP_Cu(II)_1000_pH8 | 8 | 9.379 | 8.802 | 0.938 | 105 |
| 18 | DP_Cr(III)_100_pH8 | 8 | 10.164 | 9.545 | 0.939 | 105 |
| 19 | DP_Cr(III)_500_pH8 | 8 | 11.241 | 10.057 | 0.895 | 100 |
| 20 | DP_Cr(III)_1000_pH8 | 8 | 12.400 | 11.183 | 0.902 | 101 |

TABLE 16

ELISA results of desorbed JEV antigen after 4 weeks and 7 weeks stored at 22° C. Samples marked with "n.a" were not analyzed due to sample prioritization

| No | | pH | 4 weeks @ 22° C. poly | mono | ratio | 7 weeks @ 22° C. poly | mono | ratio m/p |
|---|---|---|---|---|---|---|---|---|
| 1 | DP Fe(II) pH 7 | 7 | 14.285 | 11.213 | 0.785 | 14.181 | 11.378 | 0.802 |
| 2 | DP Fe(III) pH 7 | 7 | 14.879 | 11.552 | 0.776 | 14.323 | 11.765 | 0.821 |
| 3 | DP Ni(II) pH 7 | 7 | 16.572 | 11.862 | 0.716 | 14.231 | 11.666 | 0.820 |
| 4 | DP Co(II) pH 7 | 7 | 12.81 | 12.629 | 0.986 | 14.246 | 11.244 | 0.789 |
| 5 | DP Cu(II) pH 7 | 7 | 12.474 | 9.747 | 0.781 | 11.464 | 7.654 | 0.668 |
| 6 | DP Zn(II) pH 7 | 7 | 13.131 | 11.186 | 0.852 | 15.122 | 11.514 | 0.761 |
| 25 | DP Cr(III) pH 7 | 7 | 12.144 | 11.598 | 0.955 | 13.543 | 10.73 | 0.792 |
| 7 | DP metalmix pH 7 | 7 | 11.078 | 8.366 | 0.755 | 8.617 | 5.392 | 0.626 |
| 8 | DP unspiked pH 7 | 7 | 16.159 | 13.224 | 0.818 | 14.158 | 11.559 | 0.816 |
| 9 | DP Fe(II) pH 7.4 | 7.4 | 15.096 | 12.649 | 0.838 | 14.417 | 11.239 | 0.780 |
| 10 | DP Fe(III) pH 7.4 | 7.4 | 13.509 | 12.029 | 0.890 | 16.948 | 12.344 | 0.728 |
| 11 | DP Ni(II) pH 7.4 | 7.4 | 13.036 | 11.306 | 0.867 | 13.293 | 12.571 | 0.946 |
| 12 | DP Co(II) pH 7.4 | 7.4 | 13.715 | 11.714 | 0.854 | 13.079 | 11.96 | 0.914 |
| 13 | DP Cu(II) pH 7.4 | 7.4 | 14.235 | 11.748 | 0.825 | 10.843 | 9.276 | 0.855 |
| 14 | DP Zn(II) pH 7.4 | 7.4 | 13.815 | 12.882 | 0.932 | 13.28 | 12.619 | 0.950 |
| 26 | DP Cr(III) pH 7.4 | 7.4 | 12.324 | 11.659 | 0.946 | 13.312 | 10.804 | 0.812 |
| 15 | DP_metalmix_pH7.4 | 7.4 | | n.a. | | 9.74 | 6.551 | 0.673 |
| 16 | DP unspiked pH 7.4 | 7.4 | 13.951 | 13.225 | 0.948 | 11.97 | 12.672 | 1.059 |
| 17 | DP Fe(II) pH 7.8 | 7.8 | 14.356 | 13.102 | 0.913 | 12.625 | 13.304 | 1.054 |
| 18 | DP Fe(III) pH 7.8 | 7.8 | 13.554 | 12.388 | 0.914 | 13.003 | 10.811 | 0.831 |
| 19 | DP Ni(II) pH 7.8 | 7.8 | 13.949 | 12.496 | 0.896 | 13.106 | 11.757 | 0.897 |
| 20 | DP Co(II) pH 7.8 | 7.8 | 12.826 | 11.931 | 0.930 | 13.333 | 11.059 | 0.829 |
| 21 | DP Cu(II) pH 7.8 | 7.8 | 12.593 | 11.268 | 0.895 | 12.538 | 9.872 | 0.787 |
| 22 | DPZn(II) pH 7.8 | 7.8 | 15.217 | 14.204 | 0.933 | 15.55 | 13.217 | 0.850 |
| 27 | DP Cr(III) pH 7.8 | 7.8 | 12.977 | 13.228 | 1.019 | 14.642 | 11.975 | 0.818 |
| 23 | DP metalmix pH 7.8 | 7.8 | 11.196 | 9.811 | 0.876 | 10.771 | 7.539 | 0.700 |
| 24 | DP unspiked pH 7.8 | 7.8 | 11.906 | 11.819 | 0.993 | 12.472 | 11.034 | 0.885 |

TABLE 17

ANOVA for stability samples stored at 22° C. for 7 weeks. Analysis of Variance for Ratio - Type III Sums of Squares

| Source | Sum of Squares | Df | Mean Square | F-Ratio | P-Value |
|---|---|---|---|---|---|
| MAIN EFFECTS | | | | | |
| A: Metal Type | 0.139643 | 8 | 0.0174554 | 3.00 | 0.0293 |
| B: pH | 0.0462028 | 2 | 0.0231014 | 3.97 | 0.0398 |
| RESIDUAL | 0.0931046 | 16 | 0.00581904 | | |
| TOTAL (CORRECTED) | 0.27895 | 26 | | | |

All F-ratios are based on the residual mean square error.

TABLE 18

Multiple range test for ratio by metal ion type.
1 = Fe(II); 2 = Fe(III); 3 = Ni(II); 4 = Co(II); 5 = Cu(II); 6 = Zn(II); 7 = Cr(III); 8 = Mix[1-6]; 9 = non-spiked control
Multiple Range Tests for Ratio by Metal Type Method: 95.0 percent LSD

| Metal Type | Count | LS Mean | Homogeneous Groups |
|---|---|---|---|
| 8 | 3 | 0.666087 | X |
| 5 | 3 | 0.770168 | XX |
| 2 | 3 | 0.793725 | XXX |
| 7 | 3 | 0.807248 | XX |
| 4 | 3 | 0.844388 | XX |
| 6 | 3 | 0.853867 | XX |
| 1 | 3 | 0.878563 | XX |
| 3 | 3 | 0.887505 | XX |

TABLE 18-continued

Multiple range test for ratio by metal ion type.
1 = Fe(II); 2 = Fe(III); 3 = Ni(II); 4 = Co(II); 5 = Cu(II); 6 = Zn(II); 7 = Cr(III); 8 = Mix[1-6]; 9 = non-spiked control
Multiple Range Tests for Ratio by Metal Type

| 9 | 3 | 0.919926 | X |
|---|---|---|---|

| Contrast | Difference | +/−Limits |
|---|---|---|
| 1 − 2 | 0.084838 | 0.132037 |
| 1 − 3 | −0.0089421 | 0.132037 |
| 1 − 4 | 0.0341754 | 0.132037 |
| 1 − 5 | 0.108395 | 0.132037 |
| 1 − 6 | 0.0246961 | 0.132037 |
| 1 − 7 | 0.0713155 | 0.132037 |
| 1 − 8 | *0.212476 | 0.132037 |
| 1 − 9 | −0.0413627 | 0.132037 |
| 2 − 3 | −0.0937801 | 0.132037 |
| 2 − 4 | −0.0506626 | 0.132037 |
| 2 − 5 | 0.0235569 | 0.132037 |
| 2 − 6 | −0.0601419 | 0.132037 |
| 2 − 7 | −0.0135225 | 0.132037 |
| 2 − 8 | 0.127638 | 0.132037 |
| 2 − 9 | −0.126201 | 0.132037 |
| 3 − 4 | 0.0431175 | 0.132037 |
| 3 − 5 | 0.117337 | 0.132037 |
| 3 − 6 | 0.0336382 | 0.132037 |
| 3 − 7 | 0.0802576 | 0.132037 |
| 3 − 8 | *0.221418 | 0.132037 |
| 3 − 9 | −0.0324206 | 0.132037 |
| 4 − 5 | 0.0742195 | 0.132037 |
| 4 − 6 | −0.00947935 | 0.132037 |
| 4 − 7 | 0.0371401 | 0.132037 |
| 4 − 8 | *0.1783 | 0.132037 |
| 4 − 9 | −0.0755381 | 0.132037 |
| 5 − 6 | −0.0836988 | 0.132037 |
| 5 − 7 | −0.0370794 | 0.132037 |

TABLE 18-continued

Multiple range test for ratio by metal ion type.
1 = Fe(II); 2 = Fe(III); 3 = Ni(II); 4 = Co(II); 5 = Cu(II);
6 = Zn(II); 7 = Cr(III); 8 = Mix[1-6]; 9 = non-spiked control
Multiple Range Tests for Ratio by Metal Type

| | | |
|---|---|---|
| 5 - 8 | 0.104081 | 0.132037 |
| 5 - 9 | *−0.149758 | 0.132037 |
| 6 - 7 | 0.0466195 | 0.132037 |
| 6 - 8 | *0.18778 | 0.132037 |
| 6 - 9 | −0.0660588 | 0.132037 |
| 7 - 8 | *0.14116 | 0.132037 |
| 7 - 9 | −0.112678 | 0.132037 |
| 8 - 9 | *−0.253838 | 0.132037 |

*denotes a statistically significant difference.

TABLE 19

ICP-MS results of residual metal ion impurities present in various Alum (2%) lots

| Alum (2%) Lot | Residual metal content (ng/mL) Cr | Fe | Ni | Cu | V | Co |
|---|---|---|---|---|---|---|
| 4074 | 19.8 | 266 | 14.8 | <25 | <5 | <5 |
| 4470 | 1637 | 1179 | 17.5 | <25 | <5 | <5 |
| 4563 | 1874 | 2485 | 8.9 | <25 | <5 | <5 |
| 4621 | 1333 | 1183 | 7.6 | <25 | <5 | <5 |
| 3877 | 48.2 | 183 | 12.2 | <25 | <5 | <5 |
| 4230 (nonGI**, GI***) | 1139 | 5640 | 816 | 64 | 12.6 | 7 |
| Mix* 4074/4230 | 579.4 | 2953 | 415.4 | <44.5 | <6 | <6 |

*Calculated content of residual metals based on Alum lot 4230 and 4074
**nonGI: non gamma irradiated
***GI: gamma irradiated

TABLE 21

Results of PSD analysis of ALHYDROGEL ® (2%) stock solution in water.

| No | Sample Name | d (0.1) | d (0.5) | d (0.9) | Obscuration (%) |
|---|---|---|---|---|---|
| 1 | Non-irradiated AlOH RQCS0890 Lot 4230 | 0.70 | 2.13 | 46.53 | 1.51 |
| 2 | GI AlOH RQCS1200 Lot 4230 | 0.71 | 4.14 | 69.64 | 1.98 |
| 3 | GI AlOH RQCS1342 Lot 4740 | 0.78 | 2.23 | 53.44 | 2.11 |
| 4 | GI AlOH RQCS0448 Lot 4074 | 0.73 | 4.49 | 78.58 | 1.96 |

d (0.1): 10% of all measured particles have a diameter below this value
d (0.5): 50% of all measured particles have a diameter below this value
d (0.9): 90% of all measured particles have a diameter below this value
Obscuration: amount of laser light reduction by sample; corresponds to concentration of sample in measurement chamber

TABLE 22

Results of ALHYDROGEL ® titration curves for determination of POZ. Samples were analyzed in PBS (1:20 dilution).

| Sample ID | PZC (pH) |
|---|---|
| Non-irradiated AlOH RQCS0890 Lot 4230 | 4.58 |
| GI AlOH RQCS1200 Lot 4230 | 4.62 |
| GI AlOH RQCS1342 Lot 4740 | 4.49 |
| GI AlOH RQCS0448 Lot 4074 | 4.48 |

TABLE 20

Summary of metal ion content and analysis of DP samples formulated with various Alum lots. Samples were analysed in duplicate by ELISA and the ratio of monoclonal/polyclonal ELISA is reported. Formulations were stored at 22° C. for 6 weeks.

| # | Alum Lot (2% Stock solution) | Monoclonal $1^{st}$ analysis | Polyclonal $1^{st}$ analysis | Monoclonal $2^{nd}$ analysis | Polyclonal $2^{nd}$ analysis | Ratio $1^{st}$ analysis | Ratio $2^{nd}$ analysis | Mean ratio (Mono/poly) | Range* Ratio |
|---|---|---|---|---|---|---|---|---|---|
| 1 | 4470 | 23.584 | 26.397 | 21.666 | 22.948 | 0.893 | 0.944 | 0.918 | 0.025 |
| 2 | 4563 | 23.027 | 23.397 | 19.051 | 18.862 | 0.984 | 1.010 | 0.997 | 0.013 |
| 3 | 4621 | 22.758 | 24.056 | 19.041 | 19.196 | 0.946 | 0.991 | 0.968 | 0.023 |
| 4 | 3877 | 23.5 | 23.85 | 21.186 | 21.24 | 0.985 | 0.997 | 0.991 | 0.006 |
| 5 | 4230 (non-gamma irradiated) | 21.85 | 25.155 | 20.682 | 23.792 | 0.868 | 0.869 | 0.869 | 0.000 |
| 6 | 4230 (gamma irradiated) | 20.509 | 22.904 | 18.002 | 23.512 | 0.895 | 0.765 | 0.830 | 0.065 |
| 7 | 4074 | 23.022 | 24.047 | 16.695 | 19.866 | 0.957 | 0.840 | 0.898 | 0.058 |
| 8 | Mixture (50%/50%) of 4074 and 4230 | 20.833 | 22.954 | 22.473 | 21.217 | 0.908 | 1.059 | 0.983 | 0.076 |

*Range is the absolute difference between $1^{st}$ and $2^{nd}$ analysis.

TABLE 23

Summary of metal ion analysis for various Aluminum hydroxide stock solutions; Note: A 2% stock solution equals 10 mg/mL of Al

| ALHYDROGEL ® (2% solution) | Al | Fe | Ni | Cu | Co | Cr | Ag | Cd | W | Pb | V | Rb | Mo |
|---|---|---|---|---|---|---|---|---|---|---|---|---|---|
| | μg/mL | | | | | | ng/mL | | | | | | |
| Lot 4074 (RQCS0013) | 9130 | 266 | 15 | <25 | <5 | 20 | <5 | <5 | <25 | 19 | <5 | <5 | <5 |
| Lot 4230 (RQCS 0890) | 9570 | 5640 | 816 | 64 | 7 | 1139 | <5 | <5 | <25 | 24 | 13 | <5 | 11 |
| Lot 4470 (RQCS1254) | 9560 | 1179 | 18 | <25 | <5 | 1637 | <5 | <5 | <25 | 20 | <5 | <5 | 22 |
| Lot 4414 (RQCS1220) | 10272 | 2790 | 36 | <25 | <5 | 1710 | <5 | <5 | 35 | <25 | <7 | n.a. | n.a. |
| Lot 4539 | n.a. | 943 | 119 | <25 | <5 | 276 | <5 | <5 | <25 | 27 | <5 | <5 | <5 |
| Lot 3877 | 10766 | 183 | 12 | <25 | <5 | 48 | <5 | <5 | <25 | 10 | <5 | <5 | <5 |
| Lot 4187 | 14100 | 3617 | 172 | <25 | <5 | 2333 | <5 | <5 | <25 | 18 | <5 | <5 | <5 |
| Lot 4287 | 9800 | 2047 | 296 | <25 | <5 | 620 | <5 | <5 | <25 | 30 | 10 | <5 | <5 |
| Lot 4563 | 9360 | 2485 | 9 | <25 | <5 | 1874 | <5 | <5 | <25 | 8 | <5 | <5 | <5 |
| Lot 4621 | 9760 | 1183 | 8 | <25 | <5 | 1333 | <5 | <5 | <25 | 8 | <5 | <5 | <5 |
| Lot 4580 (7xwashed) | 10497 | 2610 | 27 | <25 | <5 | 1470 | <5 | <5 | <25 | <25 | <5 | n.a. | n.a. |
| Lot 4596 (7xwashed) | 10776 | 3530 | 27 | <25 | <5 | 1710 | <5 | <5 | <25 | <25 | <5 | n.a. | n.a. |
| Lot 4577 (7xwashed) | 10720 | 3060 | 24 | <25 | <5 | 1650 | <5 | <5 | <25 | <25 | <5 | n.a. | n.a. |
| average | 10359 | 2272 | 121 | n.a.** | <5 | 1217 | <5 | <5 | n.a.** | 18* | 11* | <5 | 16* |
| stdev | 1312 | 1538 | 225 | | | 745 | | | | 8 | 2 | | 8 |
| min | 9130 | 183 | 8 | <25 | <5 | 20 | <5 | <5 | <25 | 8 | 10 | <5 | <5 |
| max | 14100 | 5640 | 816 | 64 | 7 | 2333 | <5 | <5 | 35 | 30 | 13 | <5 | 22 |
| RSD (%) | 13 | 68 | 186 | | | 61 | | | | 44 | 14 | | 47 |

*results below LOQ were not used for average calculation;
**no average calculation possible due to results below LOQ

TABLE 24

Analysis of supernatant and Aluminum hydroxide (Lot 4230) gel fraction for contaminating metal ions shows metal ions are located in the gel, not the supernatant

| Sample | Fe | Ni | Cu | Co | Cr | Ag | Cd | W | Pb | V |
|---|---|---|---|---|---|---|---|---|---|---|
| | | | | | ng/mL | | | | | |
| Lot 4230 Supernatant | 82 | 12 | <25 | <5 | 7 | <5 | <5 | <25 | 70 | <5 |
| Lot 4230 Sediment | 6200 | 920 | <25 | <5 | 1200 | <5 | <5 | <25 | 45 | 13 |
| % supernatant compared to sediment | 1.3 | 1.3 | n.a. | n.a. | 0.6 | n.a. | n.a. | n.a. | 155.6 | n.a. |

Preferred Aspects

Aspect 1. A method for preparing an aqueous composition comprising aluminium and a protein said method comprising combining an aluminium-salt, said protein and water to produce said aqueous composition and determining the level of a heavy metal in the aqueous composition and/or the aluminium-salt.

Aspect 2. A method for preparing an aqueous composition comprising aluminium and a protein said method comprising preparing or selecting an aluminium-salt that is able to provide an aqueous composition having less than 350 ppb heavy metal based on the weight of the aqueous composition and combining said aluminium salt, said protein and water to produce said aqueous composition.

Aspect 3. A method according to aspect 1-2, further comprising buffering said aqueous composition at a pH of between 6.5 and 8.5, preferably at a pH between 7.5 and 8.5.

Aspect 4. A method according to aspect 1-3, further comprising packaging aliquots of said aqueous composition having less than 350 ppb heavy metal based on the weight of the aqueous composition in separate air-tight storage containers.

Aspect 5. A method for preparing a clinical grade aluminium-salt precipitate for incorporation into a medicament and/or vaccine, said method comprising preparing an aqueous solution of aluminium ions and precipitating said aluminium-ions from said solution, and determining the level of a heavy metal in the solution and/or the aluminium-salt precipitate.

Aspect 6. A method according to aspect 5, wherein the precipitate is selected that is able to provide an aqueous composition comprising less than 350 ppb heavy metal based on the weight of the aqueous composition.

Aspect 7. An aqueous composition comprising a protein and an aluminium-salt, said composition comprising less than 350 ppb heavy metal based on the weight of the aqueous composition.

Aspect 8. An aqueous composition according to aspect 7, which has been stored at temperatures higher than 20° C. for at least 1 month.

Aspect 9. An aqueous composition according to aspect 7 having a shelf-life of at least 20 month.

Aspect 10. An aqueous composition according to aspect 7-9, wherein said heavy metal is selected from Cu, Ni, W, Co, Os, Ru, Cd, Ag, Fe, V, Cr, Pb, Rb and Mo.

Aspect 11. An aqueous composition according to aspect 7-10, wherein said heavy metal is selected from Cu, Ni, W, Co, Os, Ru, Cd, Ag, Fe, V.

Aspect 12. An aqueous composition according to aspect 7-11, wherein said heavy metal is selected from Cu or Ni.

Aspect 13. An aqueous composition according to aspect 7-12, wherein said heavy metal is present in ionic form.

Aspect 14. An aqueous composition according to aspect 7-13, wherein the aluminium-salt is aluminiumhydroxide (Al(OH)3) or aluminiumphosphate (AlPO4).

Aspect 15. An aqueous composition according to aspect 7-14, further comprising a reactive compound.

Aspect 16. An aqueous composition according to aspect 15, wherein the reactive compound is selected from the group consisting of a redox active compound, a radical building compound, a stabilizing compound and a combination of any thereof.

Aspect 17. An aqueous composition according to aspect 15-16, wherein the reactive compound is selected from the group consisting of formaldehyde, ethanol, chloroform, trichloroethylene, acetone, TRITON™ X-100 (Polyethylene glycol tert-octylphenyl ether), deoxycholate, diethylpyrocarbonate, sulphite, $Na_2SO_2O_5$, beta-proprio-lacton, polysorbate such as TWEEN® 20 (Polysorbate 20) or TWEEN® 80 (Polysorbate 80), $O_2$, phenol, PLURONIC (poloxamer) type copolymers, and a combination of any thereof.

Aspect 18. An aqueous composition according to aspect 7-17, comprising between 5 μg/ml and 50 mg/ml aluminium.

Aspect 19. An aqueous composition according to aspect 7-18, comprising between 50 μg/ml and 5 mg/ml aluminium.

Aspect 20. An aqueous composition according to aspect 7-19, comprising between 5 ppb and 250 ppb Fe based on the weight of the aqueous composition.

Aspect 21. An aqueous composition according to aspect 7-20, comprising less than 3 ppb Cu based on the weight of the aqueous composition.

Aspect 22. An aqueous composition according to aspect 7-21, comprising less than 40 ppb Ni based on the weight of the aqueous composition.

Aspect 23. An aqueous composition according to aspect 7-22, wherein said protein is a therapeutic and/or a vaccine.

Aspect 24. An aqueous composition according to aspect 7-23, wherein said protein is a viral or bacterial protein.

Aspect 25. An aqueous composition according to aspect 7-24, wherein said viral protein is a protein of the Japanese encephalitis virus or a protein of the *Pseudomonas aeruginosa* bacterium.

Aspect 26. An aqueous composition according to aspect 7-25, wherein said protein is protein within a formaldehyde inactivated virus particles.

Aspect 27. An aqueous composition according to aspect 7-26, further comprising sulphite.

Aspect 28. An aqueous composition according to aspect 7-27, obtained by a method according to aspect 1-6.

Aspect 29. A vaccine comprising an aqueous composition according to aspect 7-28.

Aspect 30. An aluminium hydroxide concentrate that a) comprises 10 mg/ml of said aluminium hydroxide and b) less than 7 microgram heavy metal, for use in the manufacture of a medicine, preferably for use in the manufacture of a vaccine.

Aspect 31. An aluminium hydroxide concentrate that comprises 10 less than 7 microgram heavy metal, for use in the manufacture of a medicine, preferably for use in the manufacture of a vaccine.

Aspect 32. An aluminium salt concentrate that comprises less than 7 ppm heavy metal based on the weight of the concentrate, for use in the manufacture of a medicine, preferably for use in the manufacture of a vaccine.

Aspect 33. An aluminium salt concentrate that comprises less than 700 ppm heavy metal based on the weight of the aluminium salt, for use in the manufacture of a medicine, preferably for use in the manufacture of a vaccine.

Aspect 34. An aluminium hydroxide concentrate that comprises less than 700 ppm heavy metal based on the weight of the aluminium hydroxide, for use in the manufacture of a medicine, preferably for use in the manufacture of a vaccine.

Aspect 35. A method for preparing an aqueous composition comprising aluminium, a reactive compound and a protein said method comprising

- preparing or selecting an aluminium-salt that is able to provide an aqueous composition having less than 350 ppb heavy metal based on the weight of the aqueous composition and
- combining said aluminium salt, said protein, reactive compound and water to produce said aqueous composition.

Aspect 36. The method for preparing an aqueous composition according to aspect 35, wherein said heavy metal is selected from Cu, Ni, W, Co, Os, Ru, Cd, Ag, Fe, V, Cr, Pb, Rb and Mo.

Aspect 37. The method for preparing an aqueous composition according to aspect 35-36, wherein said heavy metal is selected from Cu, Ni, W, Co, Os, Ru, Cd, Ag, Fe, V.

Aspect 38. The method for preparing an aqueous composition according to aspect 35-37, wherein said heavy metal is selected from Cu or Ni.

Aspect 39. The method for preparing an aqueous composition according to aspect 35-38, wherein said heavy metal is present in ionic form.

Aspect 40. The method for preparing an aqueous composition according to aspect 35-39, wherein the aluminium-salt is aluminiumhydroxide (Al(OH)3) or aluminiumphosphate (AlPO4).

Aspect 41. The method for preparing an aqueous composition according to aspect 35-40, wherein the reactive compound is selected from the group consisting of a redox active compound, a radical building compound, a stabilizing compound and a combination of any thereof.

Aspect 42. The method for preparing an aqueous composition according to aspect 35-41, wherein the reactive compound is selected from the group consisting of formaldehyde, ethanol, chloroform, trichloroethylene, acetone, TRITON™ X-100 (Polyethylene glycol tert-octylphenyl ether), deoxycholate, diethylpyrocarbonate, sulphite, $Na_2S_2O_5$, beta-proprio-lacton, polysorbate such as TWEEN® 20 (Polysorbate 20) or TWEEN® 80 (Polysorbate 80), $O_2$, phenol, PLURONIC (poloxamer) type copolymers, and a combination of any thereof.

Aspect 43. The method for preparing an aqueous composition according to aspect 35-42, comprising between 5 μg/ml and 50 mg/ml aluminium.

Aspect 44. The method for preparing an aqueous composition according to aspect 35-43, comprising between 50 μg/ml and 5 mg/ml aluminium.

Aspect 45. The method for preparing an aqueous composition according to aspect 35-44, comprising between 5 ppb and 250 ppb Fe based on the weight of the aqueous composition.

Aspect 46. The method for preparing an aqueous composition according to aspect 35-45, comprising less than 3 ppb Cu based on the weight of the aqueous composition.

Aspect 47. The method for preparing an aqueous composition according to aspect 35-46, comprising less than 40 ppb Ni based on the weight of the aqueous composition.

Aspect 48. A method for preparing an aqueous composition according to aspect 35-47, further comprising buffering said aqueous composition at a pH of between 6.5 and 8.5, preferably 7.5 and 8.5.

Aspect 49. A method for preparing an aqueous composition according to aspect 35-48, further comprising packaging aliquots of said aqueous composition in separate air-tight storage containers.

Aspect 50. A method for prevention and/or treatment of a subject in need thereof that comprises the administration of an aqueous composition comprising an effective dose of an antigen, an aluminium compound, a reactive compound and less than 350 ppb heavy metal based on the weight of the aqueous composition.

Aspect 51. A method for prevention and/or treatment of a subject in need thereof that comprises the administration of an effective dose of a composition according to aspect 7-29.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

EQUIVALENTS

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety for the purposes cited herein.

What is claimed is:

1. An aqueous composition comprising a protein and an aluminum-salt, wherein the aluminum-salt is selected to provide an aqueous composition comprising less than 3 ppb Cu based on the weight of the aqueous composition, and wherein said protein is protein within formaldehyde inactivated virus particles.

2. The aqueous composition according to claim 1, which has been stored at temperatures higher than 20° C. for at least 1 month.

3. The aqueous composition according to claim 1, comprising less than 350 ppb heavy metal, wherein said heavy metal is selected from Ni, W, Co, Os, Ru, Cd, Ag, Fe, V, Cr, Pb, Rb and Mo.

4. The aqueous composition according to claim 1, comprising less than 350 ppb heavy metal, wherein said heavy metal is selected from Ni, W, Co, Os, Ru, Cd, Ag, Fe, and V.

5. The aqueous composition according to claim 1, comprising less than 350 ppb heavy metal, wherein said heavy metal is Ni.

6. The aqueous composition according to claim 1, comprising less than 350 ppb heavy metal, wherein said heavy metal is present in ionic form.

7. The aqueous composition according to claim 1, wherein the aluminum-salt is aluminum hydroxide ($Al(OH)_3$) or aluminum phosphate ($AlPO_4$).

8. The aqueous composition according to claim 1, wherein the aluminum-salt is aluminum hydroxide ($Al(OH)_3$).

9. The aqueous composition according to claim 1, further comprising a reactive compound selected from the group consisting of a redox active compound, a radical building compound, a stabilizing compound and a combination of any thereof.

10. The aqueous composition according to claim 1, further comprising a reactive compound selected from the group consisting of formaldehyde, ethanol, chloroform, trichloroethylene, acetone, polyethylene glycol tert-octylphenyl ether, deoxycholate, diethylpyrocarbonate, sulphite, $Na_2S_2O_5$, beta-proprio-lacton, polysorbate optionally Polysorbate 20 or Polysorbate 80, $O_2$, phenol, pluronic type copolymers, and a combination of any thereof.

11. The aqueous composition according to claim 1, comprising between 5 μg/ml and 50 mg/ml aluminum.

12. The aqueous composition according to claim 1, comprising between 50 μg/ml and 5 mg/ml aluminum.

13. The aqueous composition according to claim 1, comprising between 5 ppb and 250 ppb Fe based on the weight of the aqueous composition.

14. The aqueous composition according to claim 1, comprising less than 40 ppb Ni based on the weight of the aqueous composition.

15. The aqueous composition according to claim 1, wherein said protein is a therapeutic and/or a vaccine.

16. The aqueous composition according to claim 1, further comprising sulphite.

17. A vaccine comprising the aqueous composition according to claim 1.

18. The aqueous composition according to claim 1, wherein said composition comprises less than 2.5 ppb Cu based on the weight of the aqueous composition.

* * * * *